United States Patent
Carter et al.

(10) Patent No.: US 12,059,413 B2
(45) Date of Patent: Aug. 13, 2024

(54) METHODS OF INHIBITING VIRUSES USING COMPOSITIONS TARGETING TSG101-UBIQUITIN INTERACTION

(71) Applicants: The Research Foundation for the State University of New York, Albany, NY (US); THE UNITED STATES OF AMERICA, as represented by the Secretary, Department of Health and Human Services, Bethesda, MD (US)

(72) Inventors: Carol Carter, Huntington, NY (US); Lorna Erlich, Shoreham, NY (US); Nico Tjandra, Bethesda, MD (US); Madeleine Davison, Washington, DC (US)

(73) Assignees: THE RESEARCH FOUNDATION FOR THE STATE UNIVERSITY OF NEW YORK, Albany, NY (US); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 52 days.

(21) Appl. No.: 16/342,695

(22) PCT Filed: Oct. 30, 2017

(86) PCT No.: PCT/US2017/059111
§ 371 (c)(1),
(2) Date: Apr. 17, 2019

(87) PCT Pub. No.: WO2018/085208
PCT Pub. Date: May 11, 2018

(65) Prior Publication Data
US 2020/0038388 A1   Feb. 6, 2020

Related U.S. Application Data

(60) Provisional application No. 62/563,495, filed on Sep. 26, 2017, provisional application No. 62/555,947, (Continued)

(51) Int. Cl.
*A61K 31/4439* (2006.01)
*G01N 33/569* (2006.01)

(52) U.S. Cl.
CPC ... *A61K 31/4439* (2013.01); *G01N 33/56988* (2013.01)

(58) Field of Classification Search
CPC ......... A61K 31/4439; G01N 33/56988; G01N 33/56983; Y02A 50/30; A61P 31/12
See application file for complete search history.

(56) References Cited

U.S. PATENT DOCUMENTS

| 5,744,343 A | 4/1998 | Draetta |
| 7,202,329 B2 | 4/2007 | Wettstein |

(Continued)

FOREIGN PATENT DOCUMENTS

| EP | 1392733 A2 | 3/2004 |
| EP | 1546363 A2 | 6/2005 |

(Continued)

OTHER PUBLICATIONS

Prakash, Rabeprazole, Drugs, 1998, 55(2), pp. 261-267. (Year: 1998).*

(Continued)

*Primary Examiner* — Savitha M Rao
*Assistant Examiner* — Andrew P Lee
(74) *Attorney, Agent, or Firm* — Gary J. Gershik

(57) ABSTRACT

The present invention provides a method of inhibiting release of a virus from a cell, comprising contacting the cell with a compound that binds an ubiquitin E2 variant (UEV)

(Continued)

domain of a cellular polypeptide, or fragment thereof, with an affinity sufficient to inhibit or disrupt the binding of the cellular polypeptide, or fragment thereof, to ubiquitin.

20 Claims, 53 Drawing Sheets

Related U.S. Application Data filed on Sep. 8, 2017, provisional application No. 62/550,253, filed on Aug. 25, 2017, provisional application No. 62/416,241, filed on Nov. 2, 2016.

(56) References Cited

U.S. PATENT DOCUMENTS

| | | |
|---|---|---|
| 7,235,244 B2 | 6/2007 | Howley et al. |
| 7,335,468 B2 | 2/2008 | Zavitz et al. |
| 7,566,455 B1 | 7/2009 | Beer-Romero |
| 7,572,828 B2 | 8/2009 | Shoemaker et al. |
| 7,625,917 B2 | 12/2009 | Turpin et al. |
| 7,659,277 B2 | 2/2010 | Alroy |
| 7,714,108 B2 | 5/2010 | Li |
| 7,750,134 B2 | 7/2010 | Godzik |
| 7,776,577 B2 | 8/2010 | Kapeller-Libermann |
| 7,943,146 B2 | 5/2011 | Hobden et al. |
| 8,021,833 B2 | 9/2011 | Yu |
| 8,173,657 B2 | 5/2012 | Sutton et al. |
| 8,178,494 B2 | 5/2012 | Hays et al. |
| 8,283,355 B2 | 10/2012 | Nakache et al. |
| 8,404,747 B2 | 3/2013 | Kazantsev et al. |
| 8,476,009 B2 | 7/2013 | Li |
| 8,518,968 B2 | 8/2013 | Wiestner et al. |
| 8,618,042 B2 | 12/2013 | Cuervo et al. |
| 9,175,045 B2 | 11/2015 | Nash et al. |
| 9,464,115 B2 | 10/2016 | Walensky et al. |
| 9,492,554 B2 | 11/2016 | Arya et al. |
| 10,022,422 B2 | 7/2018 | Nash et al. |
| 10,071,164 B2 | 9/2018 | Crew et al. |
| 10,239,888 B2 | 3/2019 | Bradner et al. |
| 10,266,565 B2 | 4/2019 | Burke, Jr. et al. |
| 10,428,060 B2 | 10/2019 | Glenn et al. |
| 10,588,902 B2 | 3/2020 | Smith |
| 10,702,526 B2 | 7/2020 | Webster et al. |
| 10,765,687 B2 | 9/2020 | Leis |
| 10,806,737 B2 | 10/2020 | Crew et al. |
| 10,864,248 B2 | 12/2020 | Madden |
| 10,954,287 B2 | 3/2021 | Josephson et al. |
| 11,028,088 B2 | 6/2021 | Crews et al. |
| 11,065,231 B2 | 7/2021 | Crew et al. |
| 11,191,741 B2 | 12/2021 | Crew et al. |
| 11,220,515 B2 | 1/2022 | Crews et al. |
| 11,338,013 B2 | 5/2022 | Francois |
| 11,407,789 B2 | 8/2022 | Francois et al. |
| 11,492,590 B2 | 11/2022 | Swee et al. |
| 11,666,562 B2 | 6/2023 | Leis et al. |
| 2002/0004236 A1 | 1/2002 | Meyers |
| 2002/0019002 A1 | 2/2002 | Griffiths |
| 2002/0039773 A1 | 4/2002 | Kapeller-Libermann |
| 2003/0166504 A1 | 9/2003 | Morham |
| 2003/0195138 A1 | 10/2003 | Hitoshi |
| 2004/0109861 A1 | 6/2004 | Zavitz |
| 2004/0180353 A1 | 9/2004 | Booher |
| 2004/0223972 A1 | 11/2004 | Li |
| 2004/0224408 A1 | 11/2004 | Girard |
| 2005/0013826 A1 | 1/2005 | Shneider |
| 2005/0130896 A1 | 6/2005 | Wooten |
| 2005/0152888 A1 | 7/2005 | Church |
| 2005/0158759 A1 | 7/2005 | Kapeller-Libermann |
| 2005/0203036 A1 | 9/2005 | Colgan |
| 2006/0003413 A1 | 1/2006 | Kapeller-Libermann |
| 2006/0286630 A1 | 12/2006 | Taglicht |
| 2006/0287364 A1 | 12/2006 | Brilman |
| 2007/0060537 A1 | 3/2007 | Reis |
| 2007/0128673 A1 | 6/2007 | Hitoshi |
| 2007/0254329 A1 | 11/2007 | Rubin |
| 2009/0035853 A1 | 2/2009 | Zavitz |
| 2009/0136479 A1 | 5/2009 | Pitha-Rowe |
| 2009/0220470 A1 | 9/2009 | Rodriguez Medina |
| 2010/0047255 A1 | 2/2010 | Harper |
| 2011/0035817 A1 | 2/2011 | Wallach |
| 2011/0076248 A1 | 3/2011 | Hobden |
| 2011/0183917 A1 | 7/2011 | Lu |
| 2012/0164658 A1 | 6/2012 | Lalonde |
| 2013/0330738 A1 | 12/2013 | Klinken |
| 2014/0179637 A1 | 6/2014 | Leis |
| 2017/0137824 A1 | 5/2017 | Banerjee |
| 2020/0038388 A1 | 2/2020 | Carter |
| 2021/0308114 A1 | 10/2021 | Leis |

FOREIGN PATENT DOCUMENTS

| | | |
|---|---|---|
| EP | 1646644 A2 | 4/2006 |
| EP | 1867731 A2 | 12/2007 |
| EP | 1487486 B1 | 1/2009 |
| EP | 1377165 B1 | 7/2009 |
| EP | 2096174 A1 | 9/2009 |
| EP | 1364212 B1 | 2/2011 |
| EP | 2514439 A1 | 10/2012 |
| EP | 2750694 A2 | 7/2014 |
| EP | 2245052 B1 | 5/2017 |
| JP | H09508263 A | 1/1995 |
| JP | 2004512836 A | 4/2004 |
| JP | 2005519636 A | 7/2005 |
| JP | 2013535462 A | 9/2013 |
| WO | WO2000022110 A2 | 4/2000 |
| WO | WO2001023584 A1 | 4/2001 |
| WO | WO2001023585 A1 | 4/2001 |
| WO | WO2001023589 A2 | 4/2001 |
| WO | WO2001036605 A2 | 5/2001 |
| WO | WO2001066763 A9 | 9/2001 |
| WO | WO2002008394 A2 | 1/2002 |
| WO | WO2002063031 A2 | 8/2002 |
| WO | WO2002081730 A2 | 10/2002 |
| WO | WO2002088357 A2 | 11/2002 |
| WO | WO2003015708 A2 | 2/2003 |
| WO | WO2003059262 A2 | 7/2003 |
| WO | WO2003060067 A2 | 7/2003 |
| WO | WO2003078601 A2 | 9/2003 |
| WO | WO2004007536 A2 | 1/2004 |
| WO | WO2004009027 A2 | 1/2004 |
| WO | WO2004009028 A2 | 1/2004 |
| WO | WO2004009032 A2 | 1/2004 |
| WO | WO2004039311 A2 | 5/2004 |
| WO | WO2004058188 A2 | 7/2004 |
| WO | WO2005001485 A2 | 1/2005 |
| WO | WO2005019407 A2 | 3/2005 |
| WO | WO2005038007 A2 | 4/2005 |
| WO | WO2005043119 A2 | 5/2005 |
| WO | WO2006070348 A1 | 7/2006 |
| WO | WO2007088531 A2 | 8/2007 |
| WO | WO2008002319 A2 | 1/2008 |
| WO | WO2008097854 A2 | 8/2008 |
| WO | WO2009020559 A2 | 2/2009 |
| WO | WO2011059801 A1 | 5/2011 |
| WO | WO 2013/052800 A2 | 11/2013 |
| WO | WO2017091866 A1 | 6/2017 |
| WO | WO2019007869 A1 | 1/2019 |
| WO | WO2020150377 A1 | 7/2020 |
| WO | WO2021072075 A1 | 4/2021 |
| WO | WO2021217187 A1 | 10/2021 |

OTHER PUBLICATIONS

Clague, Ubiquitin: Same Molecule, Different Degradation Pathways, Cell, 2010, 143, pp. 682-685. (Year: 2010).*

Klinger, The ubiquitin-proteasome system in HIV replication: potential targets for antiretroviral therapy, 2005, 3(1), pp. 61-79. (Year: 2005).*

Youle, Pre-exposure chemoprophylaxis (PREP) as an HIV prevention strategy, 2003, JIAPAC, 2(3), pp. 102-105 (Year: 2003).*

(56) References Cited

OTHER PUBLICATIONS

Pornillos O. et al., "Structure of the Tsg101 UEV domain in complex with the PTAP motif of the HIV-1 p6 protein." Nat Struct Biol., Nov. 2002.; 9(11); 812-817.
Sasaki T. et al., "The proton pump inhibitor lansoprazole inhibits rhinovirus infection in cultured human tracheal epithelial cells." Eur J Pharmacol., Feb. 21, 2005; 509(2-3) : 201-210.
Skrzydio-Radomaska B. et al., "Dexlansoprazole—a new-generation proton pump inhibitor." Prz Dastroenteril, 2015; 10(4) : 191-196.
Written Opinion of the International Searching Authority issued Feb. 14, 2018 in connection with PCT International Application No. PCT/US2017/059111.
International Search Report issued Feb. 14, 2018 in connection with PCT International Application No. PCT/US2017/059111.
Dupre, S. et al., "Ubiquitin and endocytic internalization in yeast and animal cells". Biochimica et Biophysica Acta, 2004, vol. 1695, pp. 89-111.
Kim, S. et al., "Elucidation of New Binding Interactions with the Human Tsg101 Protein Using Modified HIV-1 Gag-p6 Derived Peptide Ligands". ACS Medicinal Chemistry Letters, 2011, vol. 2, 337-341.
Medina, G. et al., "Tsg101 can replace Nedd4 function in ASV Gag release but not membrane targeting". *Virology*, 2008, vol. 377(1), pp. 30-38.
Pornillos, O. et al., "Structure of the Tsg101 UEV domain in complex with the PTAP motif of the HIV-1 p6 protein". Nature Structural Biology, 2002, vol. 9(11), pp. 812-817.
Shin, J. M. and Kim, N., "Pharmacokinetics and Pharmacodynamics of the Proton Pump Inhibitors", J Neurogastroenterol Motil, 2013, vol. 19(1), pp. 25-35.
Sundquist, W. I. et al., "Ubiquitin Recognition by the Human TSG101 Protein". Molecular Cell, 2004, vol. 13, pp. 783-789.
Ariumi Y, Kuroki M, Maki M, Ikeda M, Dansako H, et al. (2011) The ESCRT System Is Required for Hepatitis C Virus Production. PLOS ONE 6(1): e14517 (Exhibit 1).
Broniarczyk J, Bergant M, Goździcka-Józefiak A, Banks L. Human papillomavirus infection requires the TSG101 component of the ESCRT machinery. Virology. Jul. 2014;460-461:83-90. doi: 10.1016/j.virol.2014.05.005. Epub May 29, 2014. PMID:25010273 (Exhibit 2).
Caduco M, Comin A, Toffoletto M, Munegato D, Sartori E, Celestino M, Salata C, Parolin C, Palù G, Calistri A. Tsg101 interacts with herpes simplex virus 1 VP1/2 and is a substrate of VP1/2 ubiquitin-specific protease domain activity. J Virol. Jan. 2013;87(1):692-6. doi: 10.1128/JVI.01969-12. Epub Oct. 17, 2012. Retraction in: J Virol. Jun. 2013;87(11):6537. PMID: 23077308; PMCID: PMC3536428(Exhibit 3).
York SB, Sun L, Cone AS, Duke LC, Cheerathodi MR, Meckes DG Jr. Zika Virus Hijacks Extracellular Vesicle Tetraspanin Pathways for Cell-to-Cell Transmission. mSphere. Jun. 30, 2021;6(3):e0019221. doi: 10.1128/mSphere.00192-21. Epub ahead of print. PMID: 34190582; PMCID: PMC8265634(Exhibit 4).
Park A, Yun T, Vigant F, Pernet O, Won ST, et al. (2016) Nipah Virus C Protein Recruits Tsg101 to Promote the Efficient Release of Virus in an ESCRT-Dependent Pathway. PLOS Pathogens 12(5): e1005659(Exhibit 5).
Chua HH, Lee HH, Chang SS, Lu CC, Yeh TH, Hsu TY, Cheng TH, Cheng JT, Chen MR, Tsai CH. Role of the TSG101 gene in Epstein-Barr virus late gene transcription. J Virol. Mar. 2007;81(5):2459-71. doi: 10.1128/JVI.02289-06. Epub Dec. 20, 2006. PMID: 17182691; PMCID: PMC1865947(Exhibit 6).
Shtanko O, Watanabe S, Jasenosky LD, Watanabe T, Kawaoka Y. ALIX/AIP1 is required for NP incorporation into Mopeia virus Z-induced virus-like particles. J Virol. Apr. 2011;85(7):3631-41. doi: 10.1128/JVI.01984-10. Epub Jan. 19, 2011. PMID: 21248028; PMCID: PMC3067881(Exhibit 7).
Dolnik O, Kolesnikova L, Stevermann L, Becker S. Tsg101 is recruited by a late domain of the nucleocapsid protein to support budding of Marburg virus-like particles. J Virol. Aug. 2010;84(15):7847-56. doi: 10.1128/JVI.00476-10. Epub May 26, 2010. PMID: 20504928; PMCID: PMC2897605(Exhibit 8).
Luyet PP, Falguières T, Pons V, Pattnaik AK, Gruenberg J. The ESCRT-I subunit TSG101 controls endosome-to-cytosol release of viral RNA. Traffic. Dec. 2008;9(12):2279-90. doi: 10.1111/j.1600-0854.2008.00820.x. Epub Sep. 24, 2008. PMID: 18817529(Exhibit 9).
Tandon R, AuCoin DP, Mocarski ES. Human cytomegalovirus exploits ESCRT machinery in the process of virion maturation. Journal of Virology. Oct. 2009;83(20):10797-10807. DOI: 10.1128/jvi.01093-09. PMID: 19640981; PMCID:PMC2753131 (Exhibit 10).
Sanyal S, Ashour J, Maruyama T, Altenburg AF, Cragnolini JJ, Bilate A, Avalos AM, Kundrat L, García-Sastre A, Ploegh HL. Type I interferon imposes a TSG101/ISG15 checkpoint at the Golgi for glycoprotein trafficking during influenza virus infection. Cell Host Microbe. Nov. 13, 2013;14(5):510-21. doi: 10.1016/j.chom.2013.10.011. PMID:24237697; PMCID: PMC3904747(Exhibit 11).
Chen M, Cortay JC, Logan IR, Sapountzi V, Robson CN, Gerlier D. Inhibition of ubiquitination and stabilization of human ubiquitin E3 ligase PIRH2 by measles virus phosphoprotein. J Virol. Sep. 2005;79(18):11824-36. doi: 10.1128/JVI.79.18.11824-11836.2005. PMID: 16140759; PMCID: PMC1212616(Exhibit 12); and.
Amit I, Yakir L, Katz M, Zwang Y, Marmor MD, Citri A, Shtiegman K, Alroy I, Tuvia S, Reiss Y, Roubini E, Cohen M, Wides R, Bacharach E, Schubert U, Yarden Y. Tal, a Tsg101-specific E3 ubiquitin ligase, regulates receptor endocytosis and retrovirus budding. Genes Dev. Jul. 15, 2004;18(14):1737-52. doi: 10.1101/gad.294904. PMID:15256501; PMCID: PMC478194(Exhibit 13).

* cited by examiner

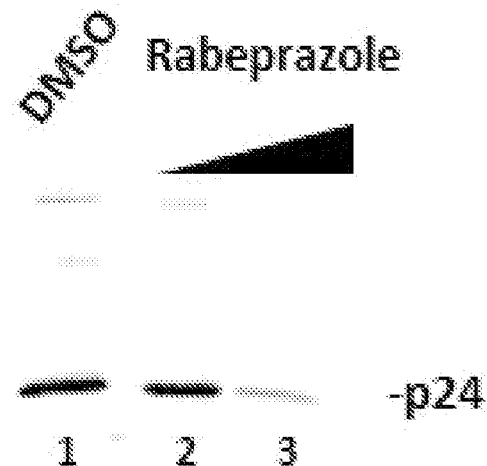
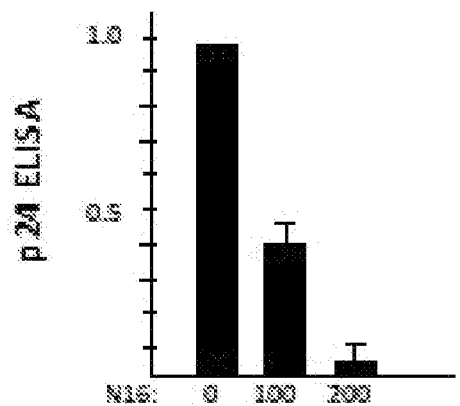
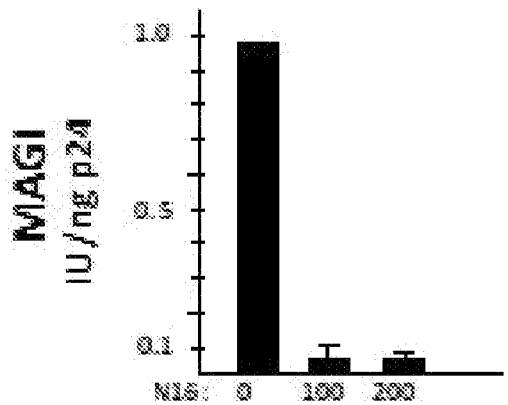
FIG. 3

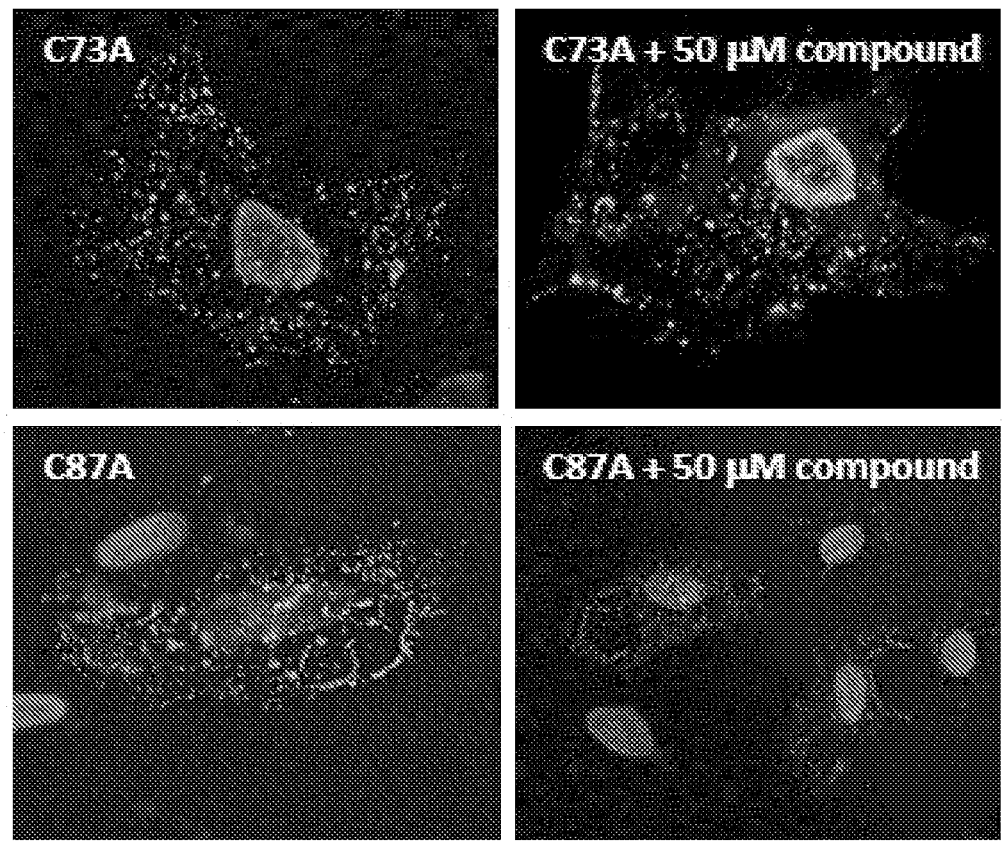
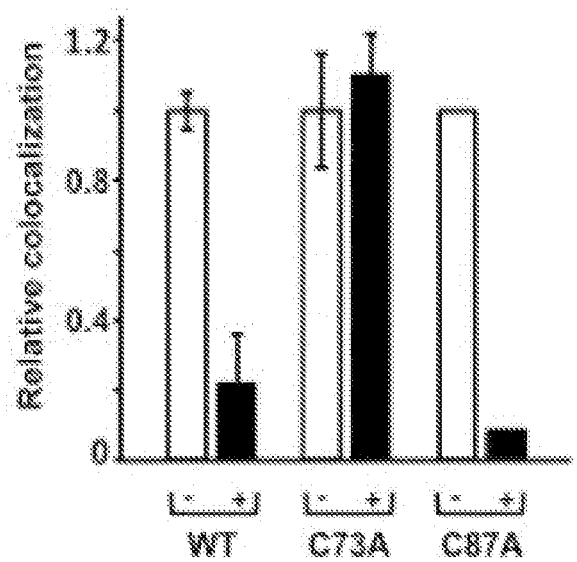
FIG. 5D

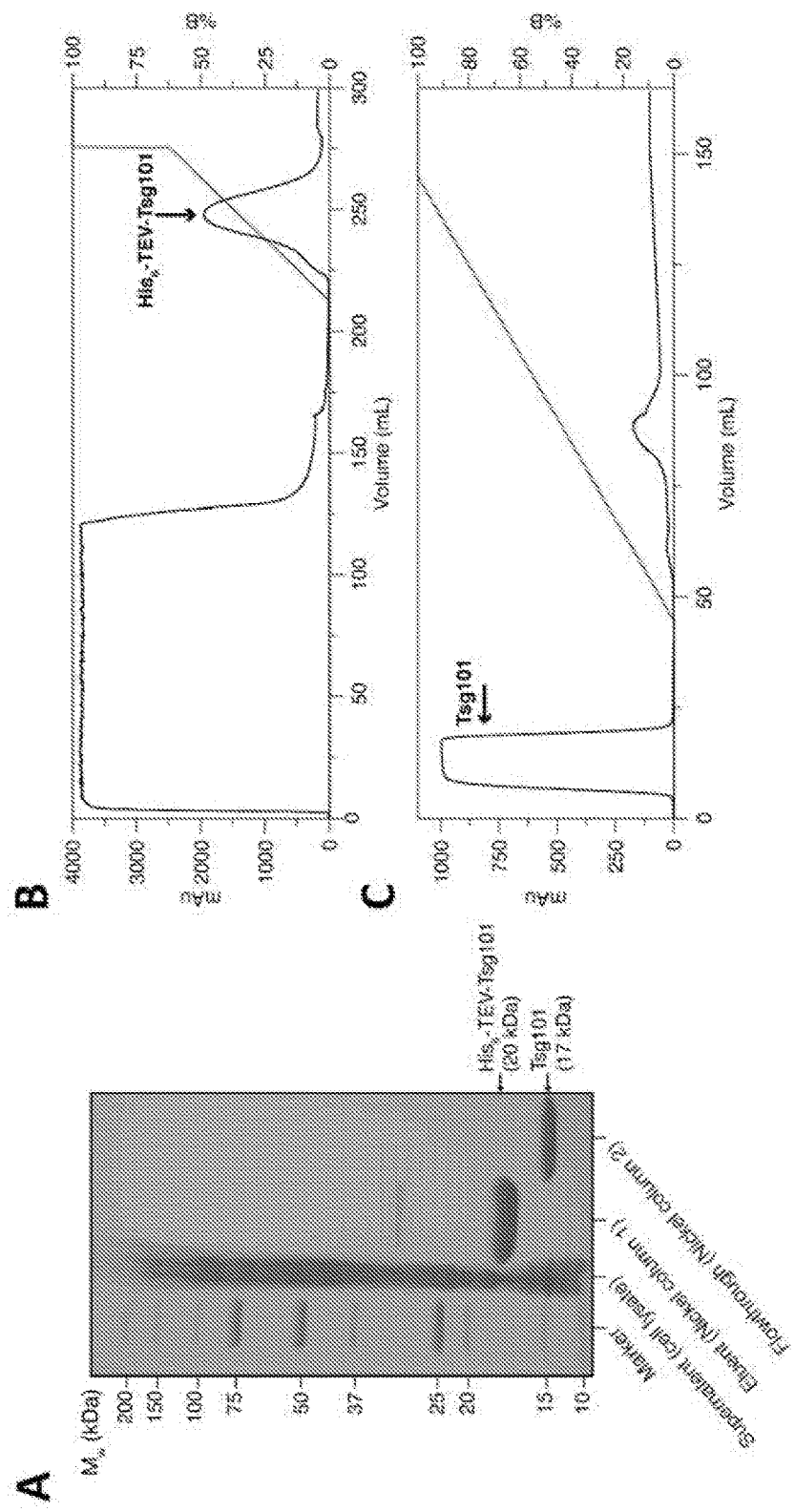
FIG. 14A-C

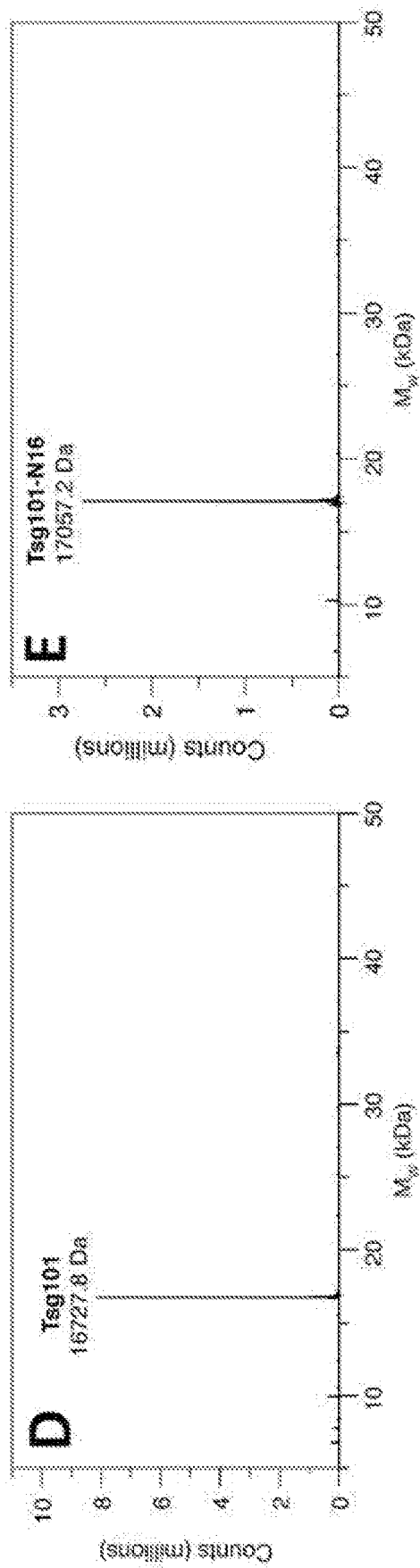
FIG. 14D-E

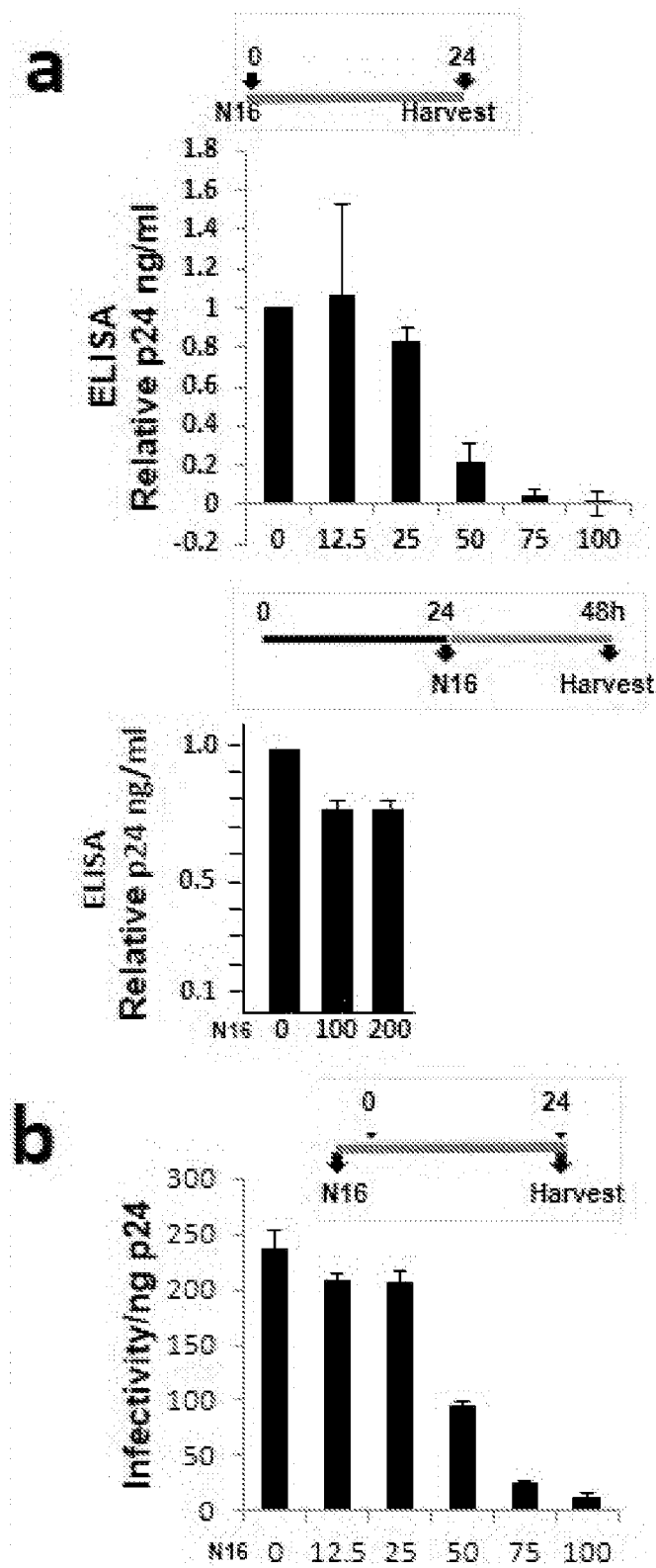
FIG. 15A-B

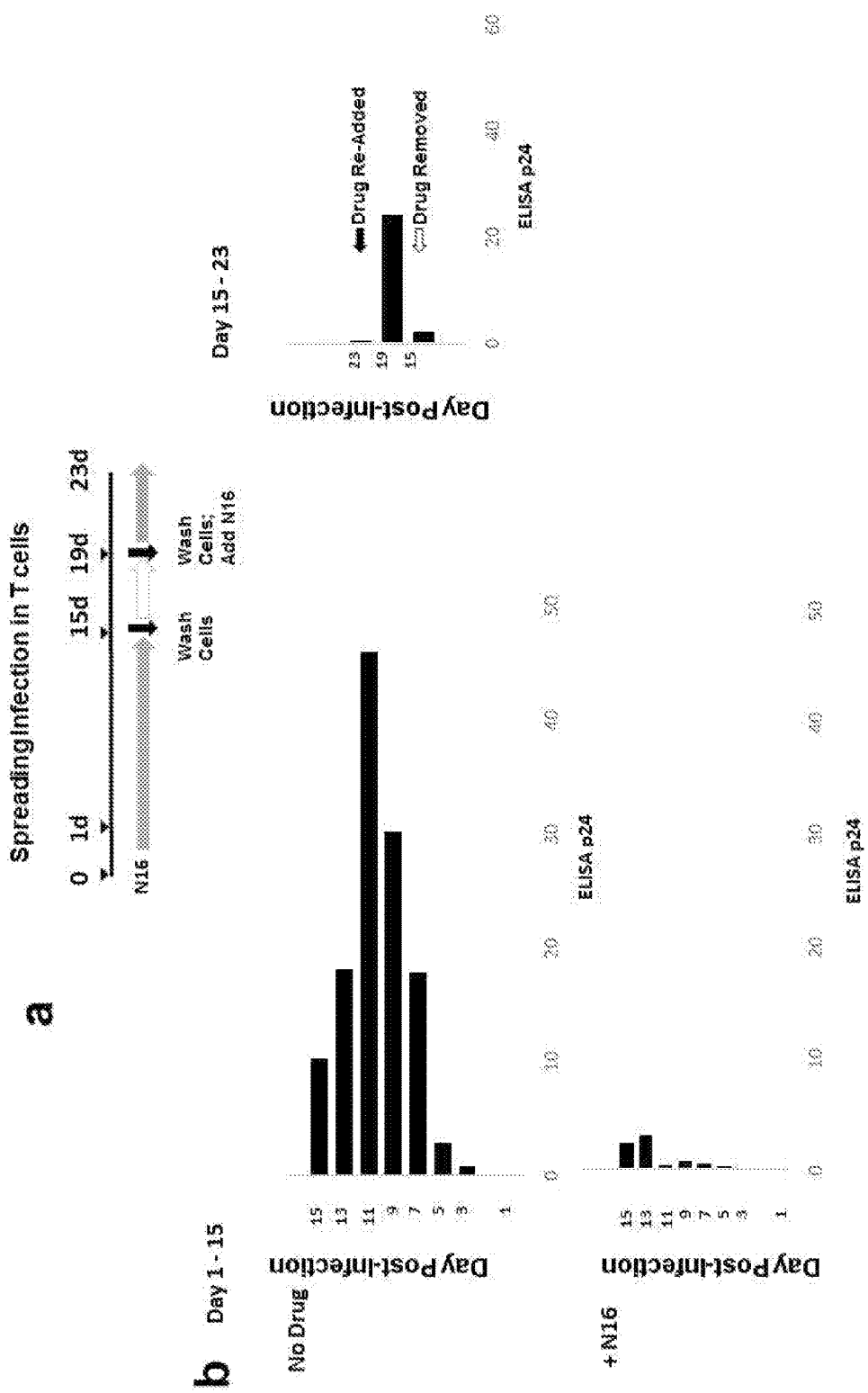
FIG. 16A-B

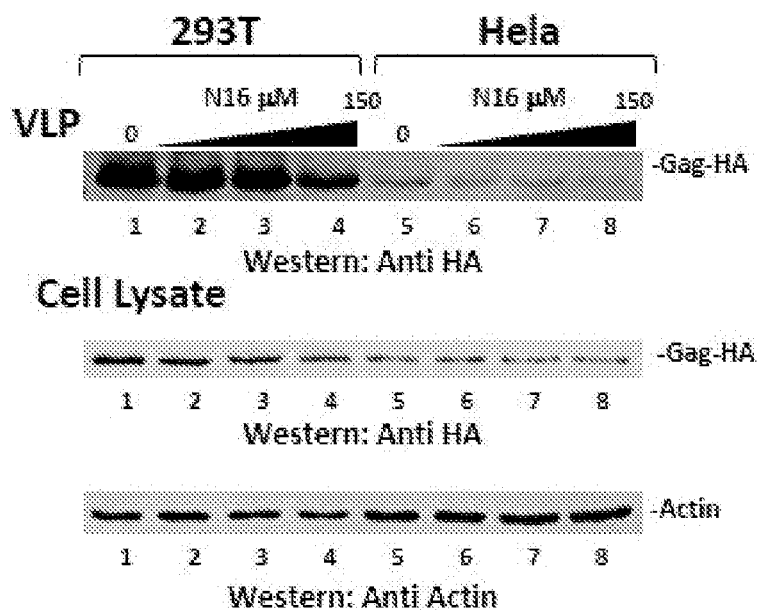
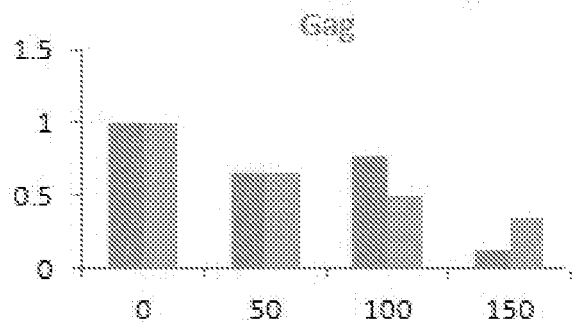
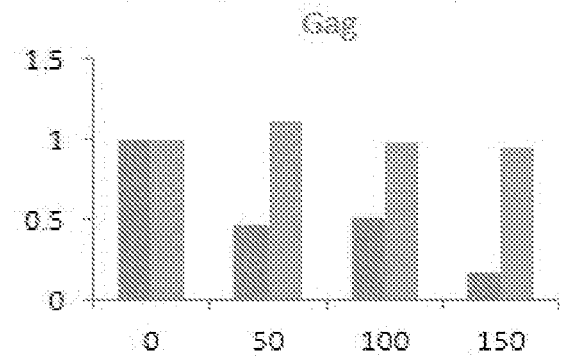
FIG. 17A

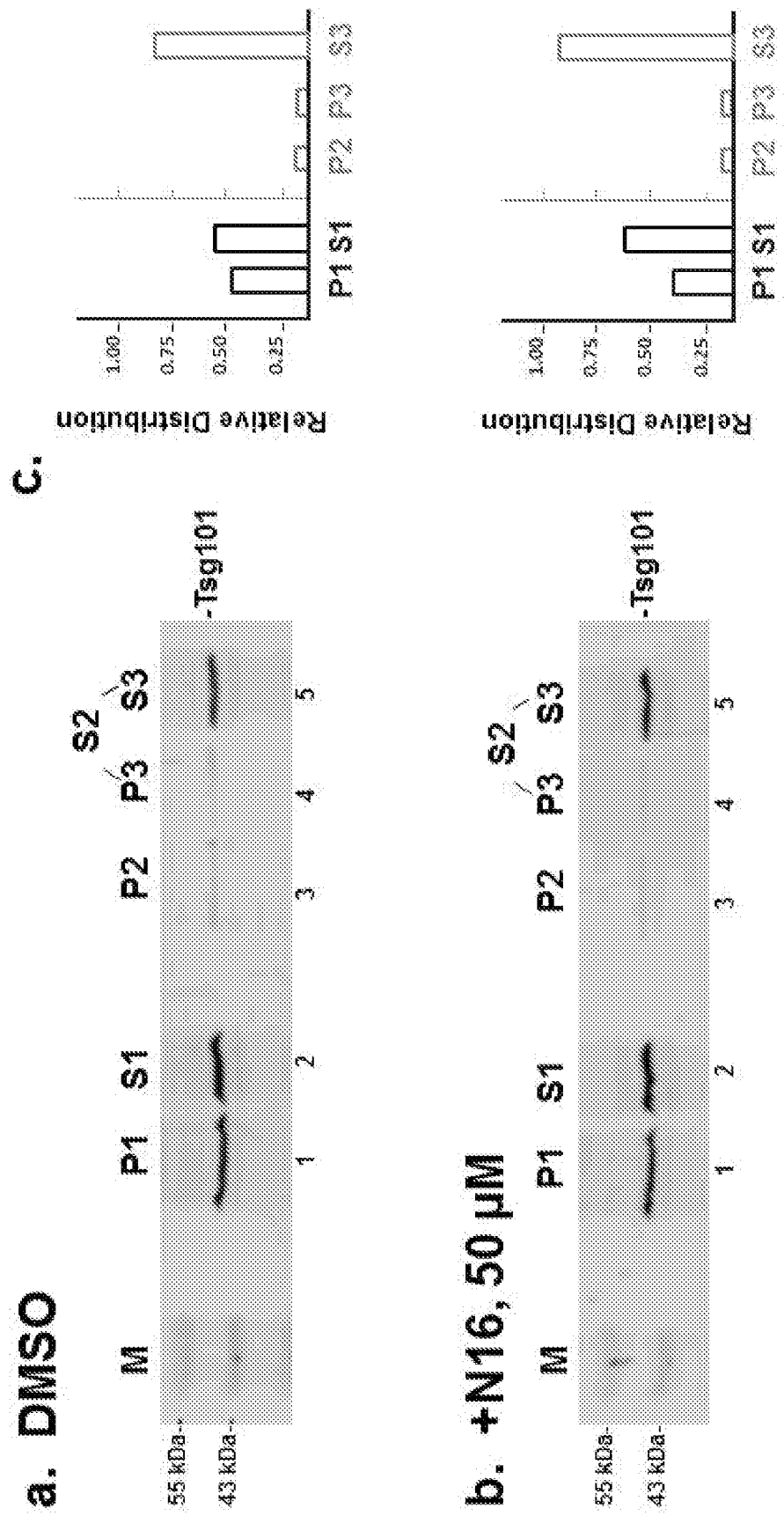
FIG. 18A-C

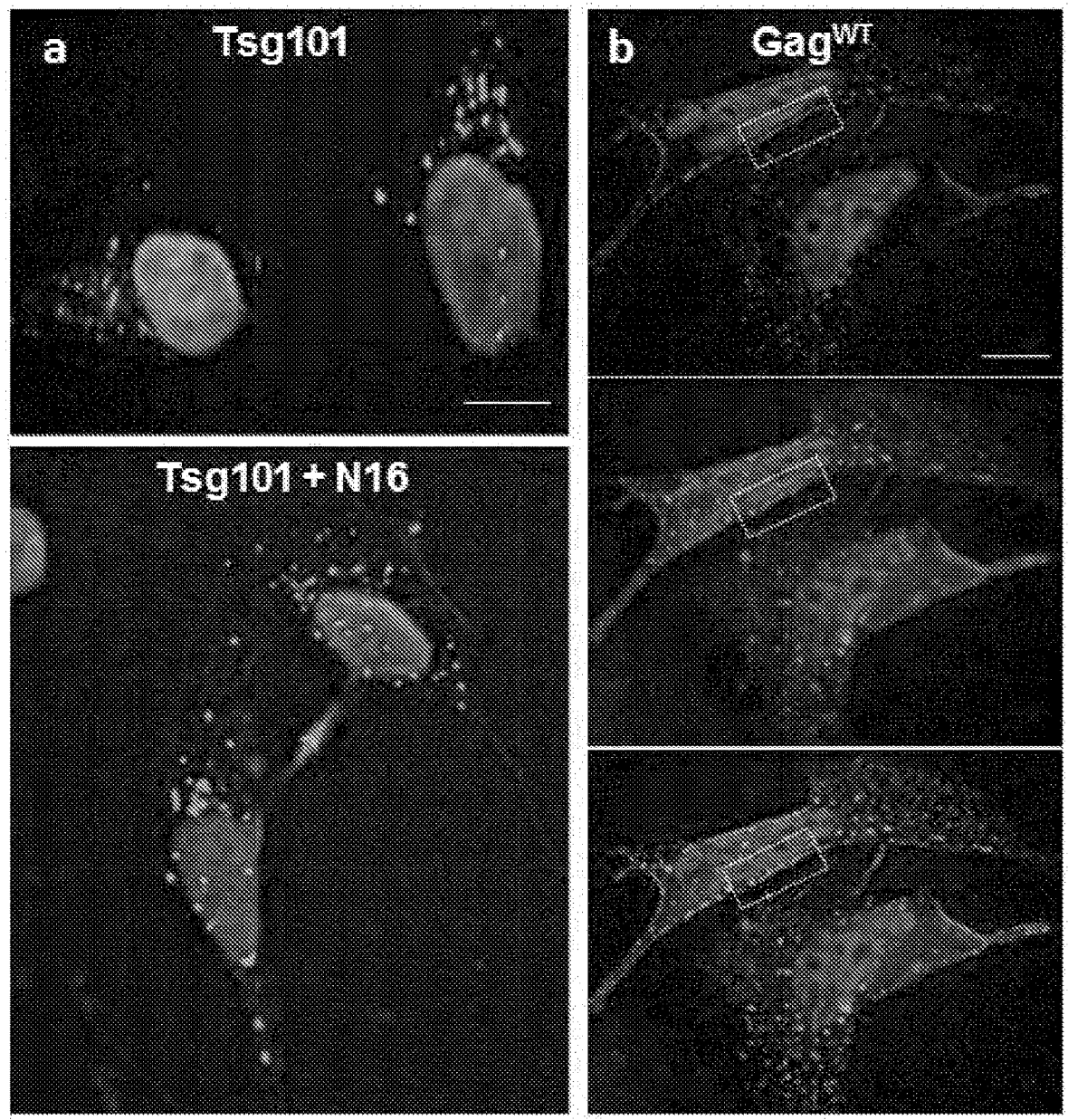
FIG. 19A-B

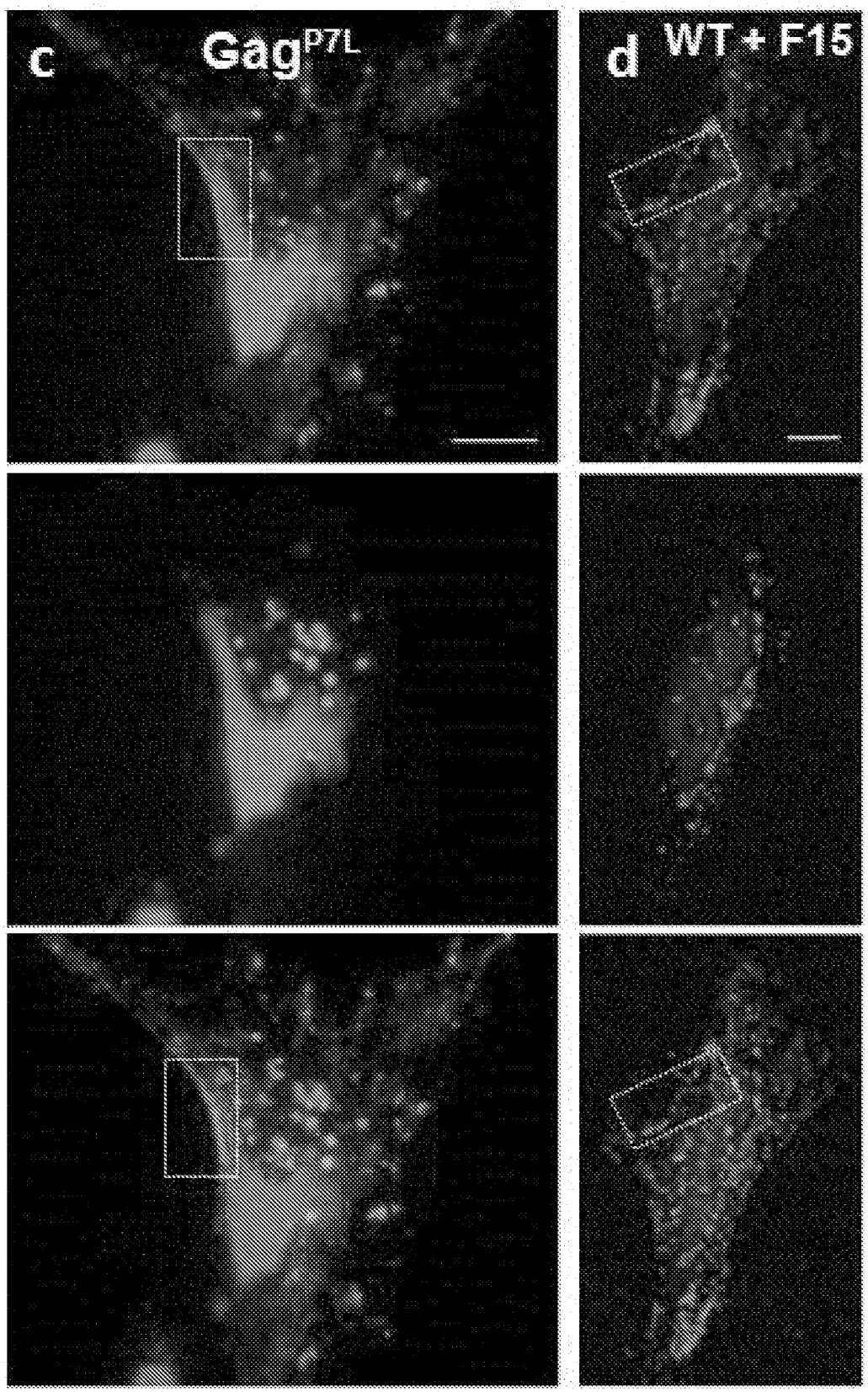
FIG. 19C-D

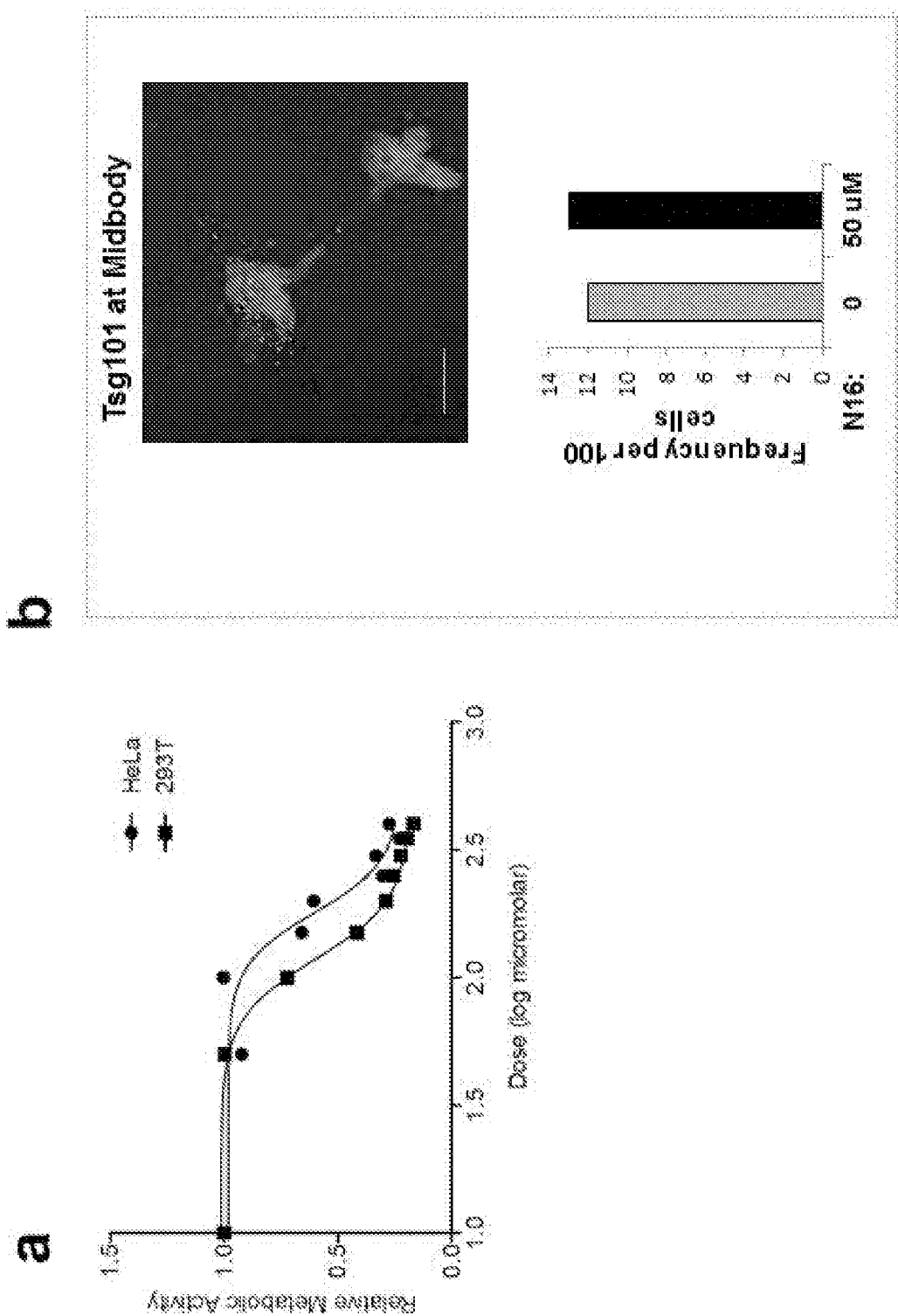
FIG. 20A-B

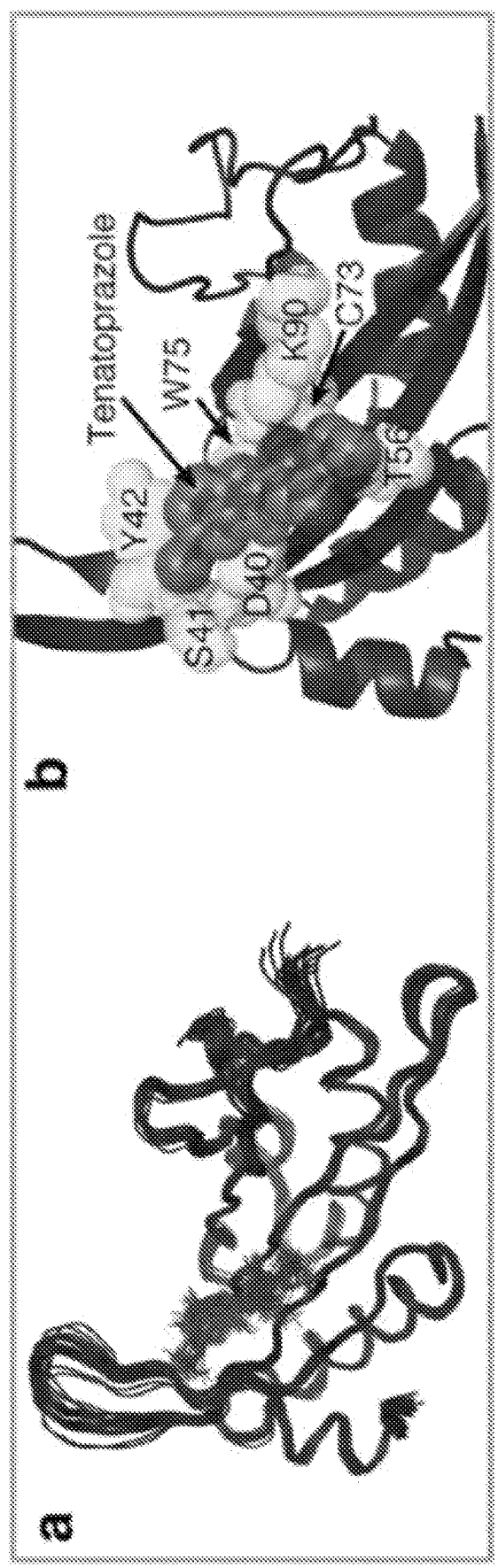
FIG. 22A-B

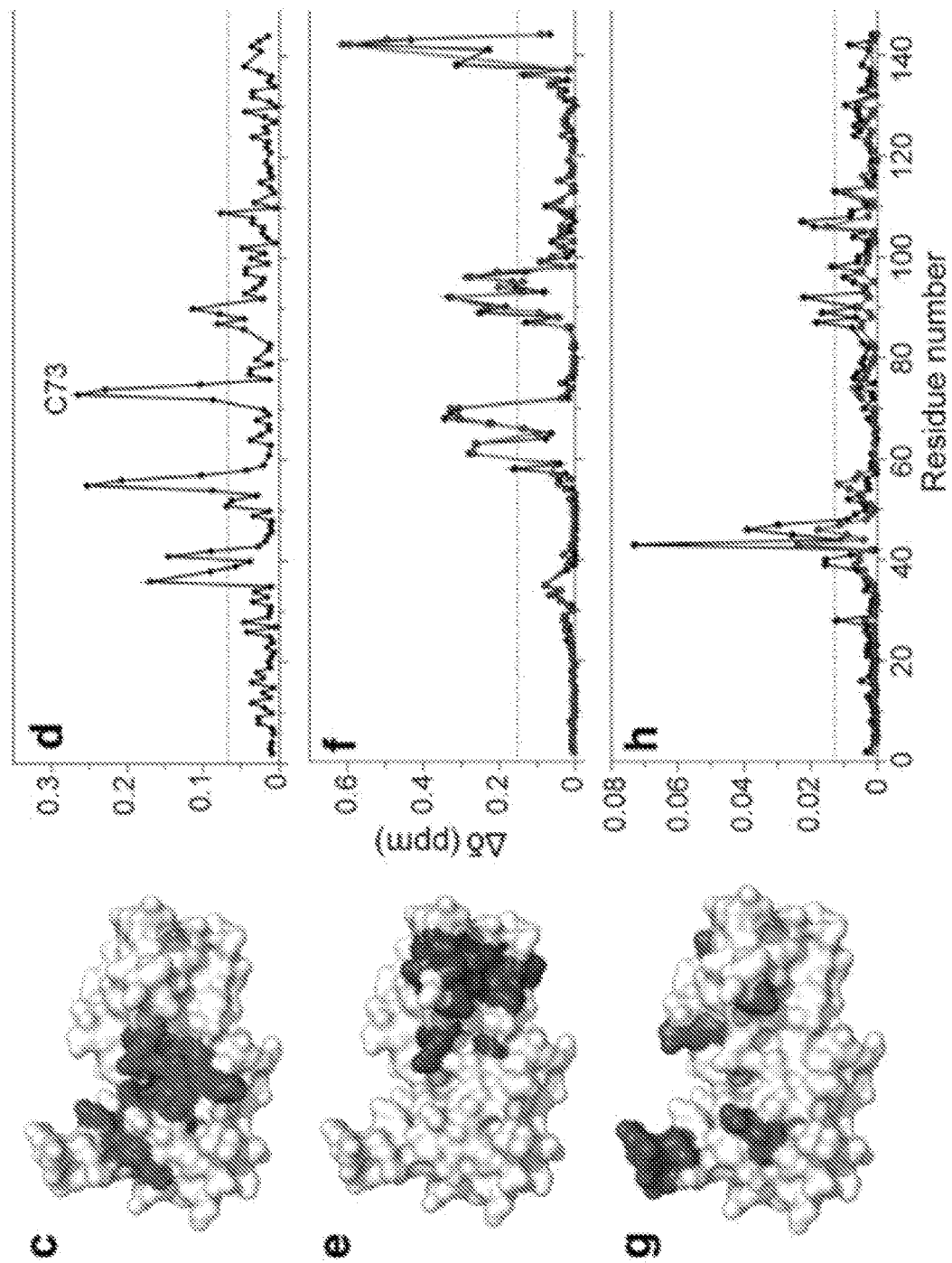
FIG. 22C-H

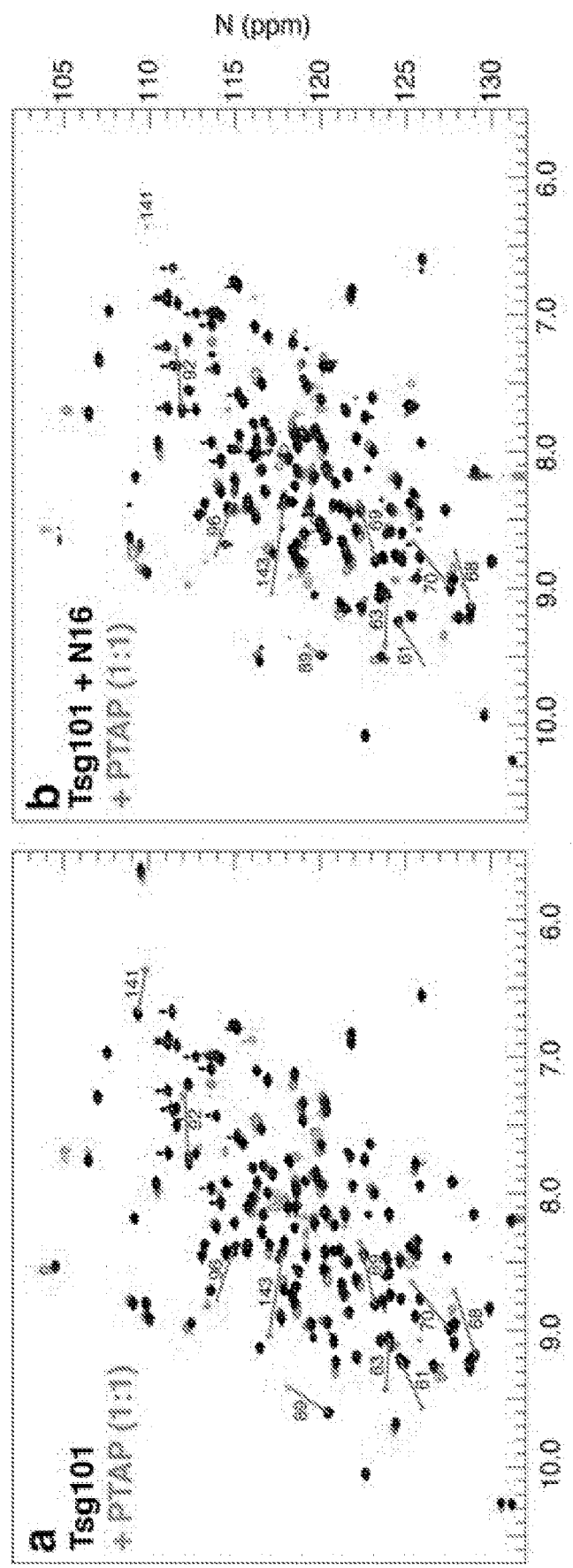
FIG. 24A-B

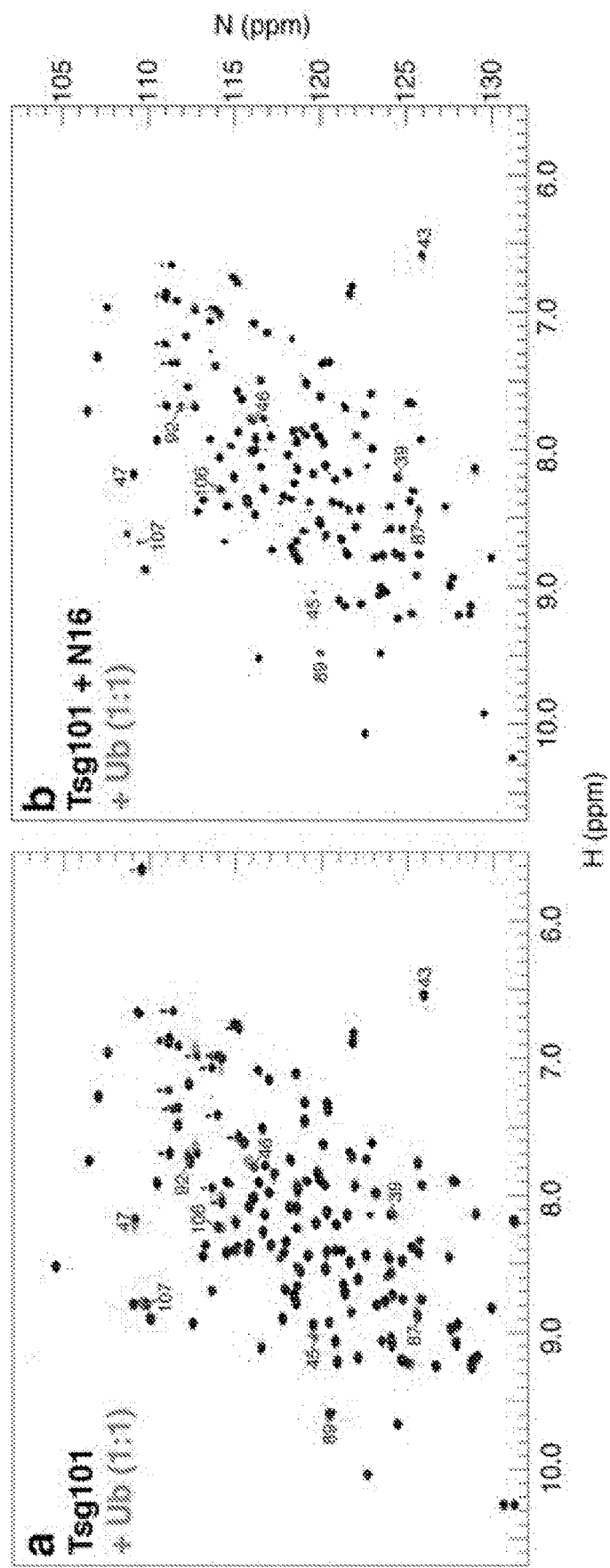
FIG. 25A-B

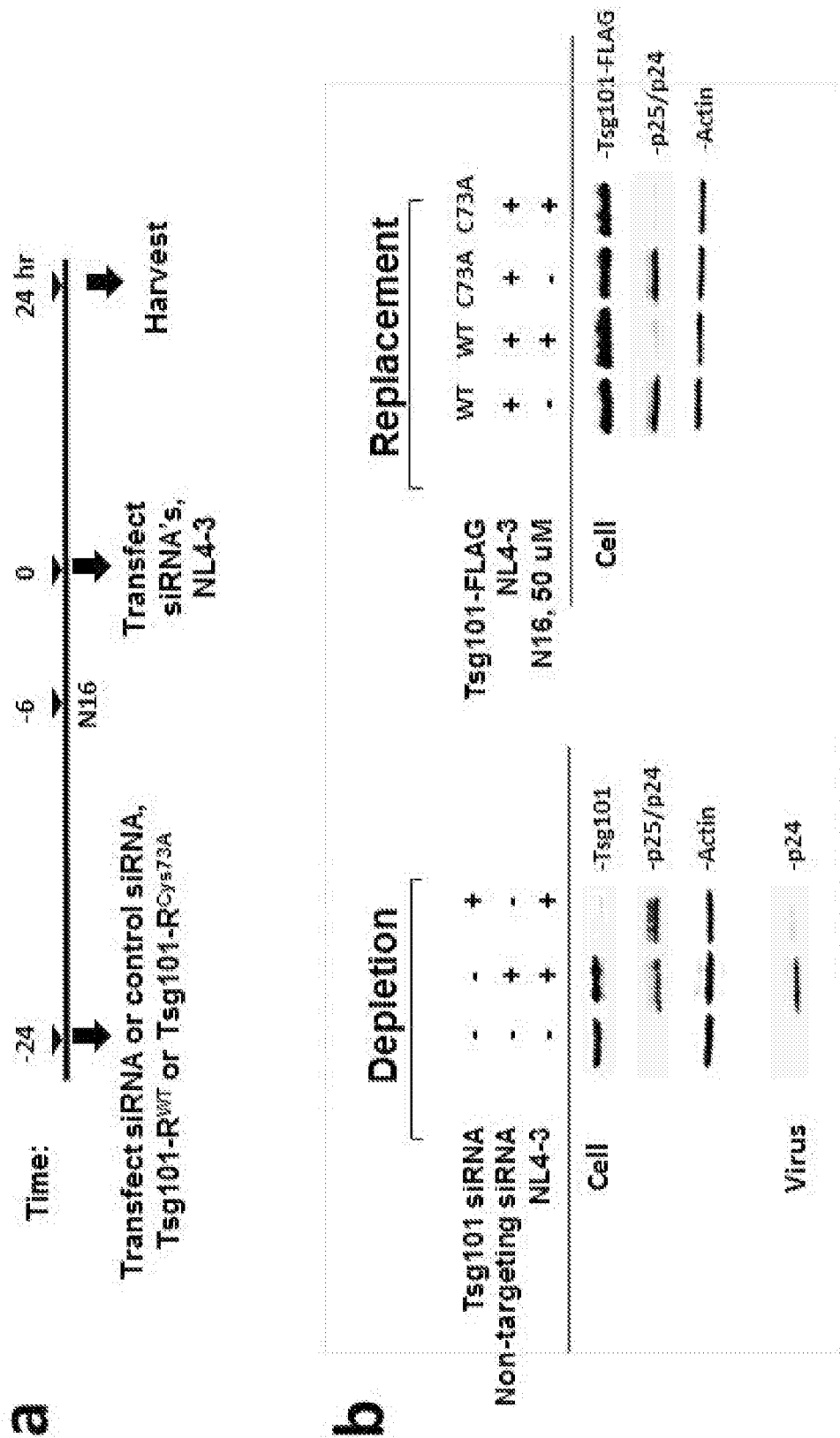
FIG. 28A-B

METHODS OF INHIBITING VIRUSES USING COMPOSITIONS TARGETING TSG101-UBIQUITIN INTERACTION

CROSS-REFERENCE TO RELATED APPLICATIONS

This application is a § 371 national stage of PCT International Application No. PCT/US2017/059111, filed Oct. 30, 2017 and claims the benefit of U.S. Provisional Application No. 62/563,495, filed Sep. 26, 2017, U.S. Provisional Application No. 62/555,947, filed Sep. 8, 2017, U.S. Provisional Application No. 62/550,253, filed Aug. 25, 2017, and U.S. Provisional Application No. 62/416,241, filed Nov. 2, 2016, the contents of each of which are herein incorporated by reference in entirety and for all purposes.

GOVERNMENT SUPPORT

This invention was made with government support under grant number GM111028 awarded by the National Institutes of Health. The government has certain rights in the invention.

Throughout this application, certain publications and patent application publications are referenced. Full citations for the publications may be found immediately preceding the claims. The disclosures of these publications and patent application publications in their entireties are hereby incorporated by reference into this application in order to describe more fully the state of the art to which this invention relates.

BACKGROUND OF THE INVENTION

Polyubiquitylation serves as a signal triggering internalization of cell-surface proteins [Dupre et al (2004), *Ubiquitin and endocytic internalization in yeast and animal cells. Biochim Biophys Acta.* 1695:89-111]. However, these normal signaling events oppose some steps important for pathogen replication, e.g., the process of enveloped virus egress from the plasma membrane of infected cells or budding of some viral intermediates from the nucleus into the cytoplasm. Several viruses, including the human immunodeficiency virus (HIV-1), engage cellular machinery to facilitate exit from the cell periphery but, as this same machinery functions in cell protein internalization, the virus must employ additional measures to prevent its proteins from being treated like cellular cargo.

SUMMARY OF THE INVENTION

The present invention provides a method of inhibiting release of a virus from a cell, comprising contacting the cell with a compound that binds an ubiquitin E2 variant (UEV) domain of a cellular polypeptide, or fragment thereof, with an affinity sufficient to inhibit or disrupt the binding of the cellular polypeptide, or fragment thereof, to ubiquitin.

The present invention also provides a method of treating a patient infected with a virus, comprising administering to the patient a compound which binds to the UEV domain Ub-binding pocket of a cellular polypeptide in an amount effective to inhibit the binding of the cellular polypeptide to ubiquitin.

The present invention also provides a method for identifying a compound that binds a UEV domain Ub-binding pocket of a cellular polypeptide with an affinity sufficient to inhibit or disrupt formation of an associative complex in a cell, comprising the steps of:

a) obtaining a test compound;
b) contacting the test compound with a cellular polypeptide, or fragment thereof, including a UEV domain Ub-binding pocket, in the presence of an ubiquitin-modified polypeptide of the virus, or fragment thereof, that is capable of binding said UEV domain Ub-binding pocket, or an ubiquitin-modified cellular polypeptide for the virus' production other than the cellular polypeptide that includes the UEV domain Ub-binding pocket, or fragment thereof, that is capable of binding said UEV domain Ub-binding pocket;
c) determining whether the test compound inhibits or disrupts the formation of an associative complex comprising the cellular polypeptide, or fragment thereof, including a UEV domain Ub-binding pocket and the ubiquitin-modified polypeptide of the virus, or fragment thereof, that is capable of binding said UEV domain Ub-binding pocket, or the ubiquitin-modified cellular polypeptide for the virus' production other than the cellular polypeptide that includes the UEV domain Ub-binding pocket, or fragment thereof, that is capable of binding said UEV domain Ub-binding pocket, thereby identifying the test compound as a compound that binds a UEV domain Ub-binding pocket of a cellular polypeptide with an affinity sufficient to inhibit or disrupt formation of an associative complex in a cell.

BRIEF DESCRIPTION OF THE DRAWINGS

The above and other objects, features and advantages of certain embodiments of the present invention will be more apparent from the following detailed description taken in conjunction with the accompanying drawings, in which:

FIG. 3. Inhibition of HIV-1 virus production. Cells transfected with the HIV-1 molecular clone, NL4-3, were treated with increasing concentrations of rabeprazole. Virus production was measured from the amount of virus detected in the tissue culture media at the end of a 24-hr treatment period. Top, semi-quantitation by immunoblotting. Virus particles in filtered tissue culture media were isolated by sucrose cushioning and electrophoresis on SDS polyacrylamide gel. Proteins separated on the gel were blotted onto nitrocellulose and the blot probed with anti-p24 antibody revealing the mature p24 protein as the major p24-containing viral protein on the blot. Middle, quantitation analysis by ELISA. Proteins in tissue culture media were denatured and total p24 protein level quantitated using p24-capture ELISA assay. Assay values were normalized to that of the DMSO carrier control. Bottom, quantitation of specific virus infectivity. Tissue culture volumes calculated to contain equivalent amounts of viral particles were used to infect a monolayer of MAGI cells in a single round HIV-I replication assay. Assay values were normalized to that of the DMSO carrier control.

FIG. 5A-D. Covalent binding to Tsg101 residue C73. FIG. 5A, compound activation to reactive sulfenamide (Shin & Kim, J Neurogastroenterol Motil 2013). Compound (i) is converted through acid catalysis to intermediates sulfenic acid (ii) and sulfenamide (iii) with reactivity to Cys residue sulfides to yield a covalently attached compound (iv) in the compound-Tsg101 UEV domain complex. FIG. 5B, loss of inhibitory effect of compound when activation is allowed to takes place prior to addition of compound to cells. Western blot analysis (left panels) of VLP from cells treated with compound and from cells treated with sulfenamide formed by acidification of compound prior to addition to cells. FIG. 5C, NMR evidence for disulfide bond formation with Tsg101 UEV domain residue Cys73. Chemical shift of residues C73, L74, 186 and C87 of Tsg101 UEV domain without (−) and with (+) compound. The Cβ peak for C73 changed from 29.27 to 46.69 ppm upon addition of compound, indicating oxidation (formation of a covalent disulfide bond), whereas the Cβ peak for C87 remained unchanged. FIG. 5D, confocal microscopy evidence for the targeting of Tsg101 UEV domain residue Cys73 by the compound inside the cell. Examination of cells co-expressing GagWT-GFP and Tsg101C73A-Myc (top panels) or GagWT-GFP and Tsg101C87A-Myc (bottom panels) in the absence (top & bottom left panels) and presence (top & bottom right panels) of compound for Gag-Tsg101 co-localization at the cell edge. Bar graph, quantification of co-localization in the absence (−, unfilled bar) and presence (+, filled bar) of treatment. The number of cells exhibiting co-localization under the treatment condition was normalized to the number in the mock-treated control.

FIG. 6A, Rabeprazole (center)—related compounds referred to as prazoles. FIG. 6B, Residues perturbed by bound compound superimposed on ribbon drawing of the Tsg101 UEV domain complexed with the PEPTAPPEE peptide delived from PDB structure 1M4P (Pornillos et al Nat Struct Biol, 2002). UEV residue Cys73 with which the compound forms a disulfide-linked adduct is shown. Residues perturbed by the bound compound are shown in with darker intensity reflecting extent of perturbation. Larger perturbations were near residues found critical for Ub binding (Pomillos et al EMBO J 2002). Although binding of compound did not interfere with PTAP binding (FIG. 4), perturbation extended to contact points for Pro 7 and Pro 10 of the P7TAP10 peptide.

FIGS. 10A, 10B, and 10C compare the antiviral effect of Rabeprazole to prazoles.

FIG. 14A-F. The ubiquitin E2 variant (UEV) domain of Tsg101 was purified by attaching it to an N-terminal His tag with a Tobacco Etch Virus nuclear-inclusion-a endopeptidase (TEV) cleavage site and isolating the tagged protein through two consecutive nickel columns. The first nickel column bound the Tsg101 with the His tag. Following cleavage of the His tag, Tsg101 flowed straight through the second column, removing any impurities from the cell lysate that also bound to the column in step 1, as well as the TEV protease enzyme. A-C describe the purification; D and E describe the addition of the N16 ligand; panel F shows binding of N16 (top) and F15 (bottom) to the purified Tsg101 UEV fragment.

Figure 1:
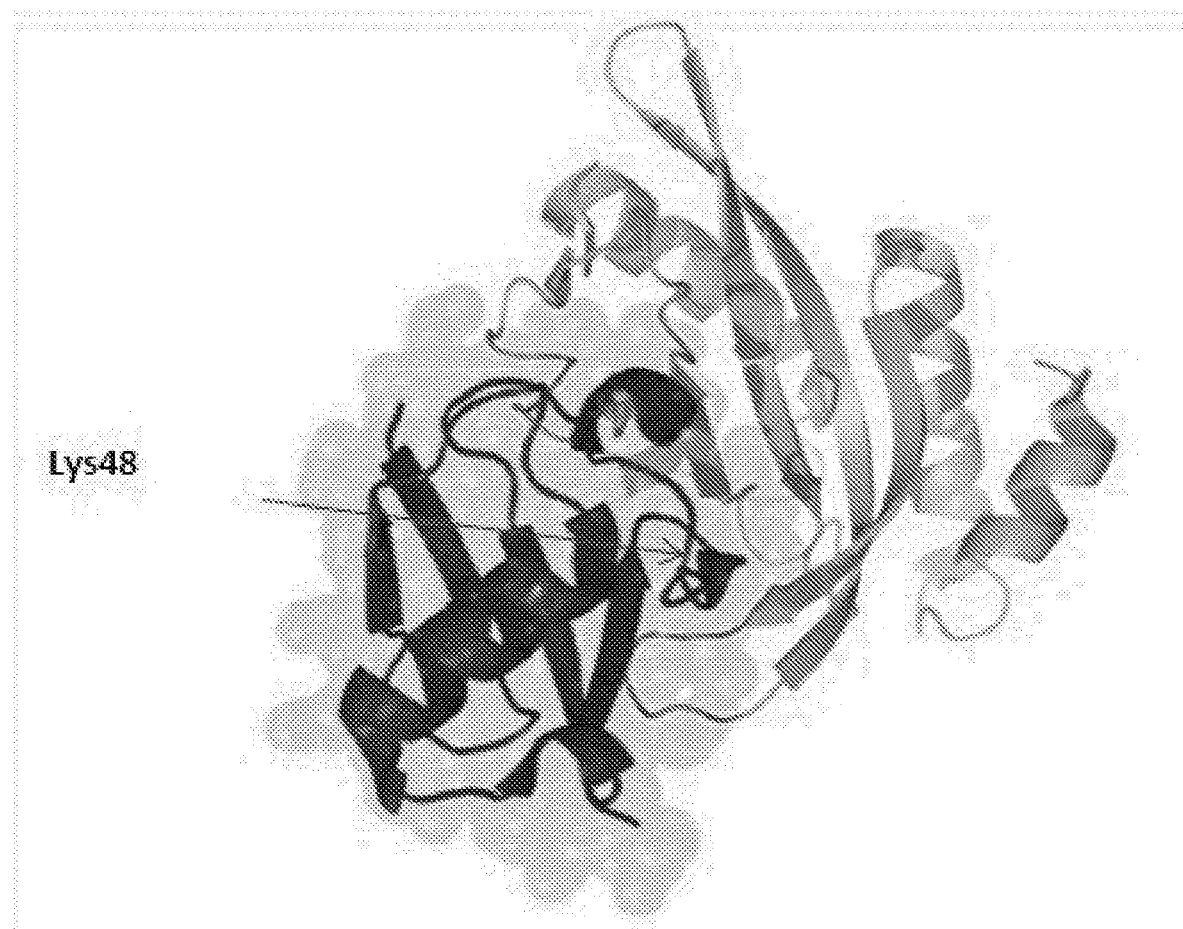
FIG. 1. Tsg101 ubiquitin E2 variant (UEV) domain complexed to ubiquitin. Ribbon drawing of Tsg101 UEV domain (lighter ribbon) with bound ubiquitin moeity (darker ribbon) derived from structural analysis information from Pornillos et al (EMBO J, 2002). Highlighted (arrow) is the buried position of the ubiquitin residue Lys48.

A) SDS-PAGE showing the cell lysate, the bound fractions from nickel column 1 (including His-TEV-Tsg101 and some impurities) and the flow-through from nickel column 2 (pure Tsg101)

B) The FPLC trace for nickel column 1 (histidine gradient)

C) The FPLC trace for nickel column 2 (histidine gradient)

D) LC-MS for free Tsg101 (cleaved)

E) LC-MS for Tsg101-N16 (increased mass indicates N16 binding)

F) Dose-dependence of Tsg101 normalized melting curves for N16 (top) and F15 (bottom). At same concentration, N16 shifts the melting curve to a greater extent to the left than F15. Specifically, at 20 uM, N16 caused a 12 degree Tm shift while F15 gave rise a 5 degree Tm shift. This difference correlated with the potency observed in the cell-based assay. The plot for N16 contains two control compounds, K21 and N20, which have no effect at 40 uM on the Tsg101 melting curve.

FIG. 15A-D. N16 inhibits HIV-1 NL4-3 and Gag VLP production. A) Effect on virus production. Virus particles from N16-treated 293T cells transfected with pNL4-3 as determined by ELISA assay. Top, The compound was added 6 hr prior to DNA transfection and tissue culture media was harvested 24 hr later. Bottom, The compound was added at the indicated concentration 24 hr after DNA transfection and tissue culture media was harvested 24 hr later. Assay values were normalized to that of the DMSO carrier control. B) Effect on virus infectivity. Infectious viral particles per ng p24 as determined by MAGI assay. C) Left, Electron microscopy of particles at cell surface at 24 hr post-N16 addition; Right, Quantitative analysis of budding morphologies. Cells expressing WT- or P7L-NL4-3 were exposed to DMSO carrier or 50 μM N16. Arrows indicate emerging 'Early' buds. D) Effects on Gag VLP production. Top, Western blot analysis. Cells treated at the indicated concentration were transfected with DNA encoding Gag-HA. At the end of the treatment period, tissue culture media was removed for VLP isolation. Cells were suspended in lysis buffer. Blots were probed for Gag-HA and actin. Bottom, Quantitative analysis. Ratio of VLP- or cell-associated Gag to actin normalized to the mock-treated control (0 μM N16). Number of independent trials (n) for A), B), C), and D)=3, 2, 2 and 3, respectively.

FIG. 16A-B. N16 inhibition of HIV-1 transmission in a spreading infection in Jurkat cells. A) Schematic diagram summarizing experimental protocol. Jurkat cells (triplicate samples of 5×105/well) were incubated for 2 hr with HIV-1 NL4-3 in treatment media containing 50 μM N16 or control vehicle (DMSO). At the end of this period, unbound virus was removed by centrifugation and the cells washed once, resuspended in fresh media and returned to the 37° C. incubator. For the next 15 days, tissue culture media was removed daily by centrifugation and saved for virus measurement by p24 capture ELISA and cells were replenished with fresh control or N16 treatment media. B) ELISA readings. In control media (containing DMSO), virus replication peaked at day 11; in the presence of N16, production peaked at 13 days. A comparison of peak values indicated that N16 reduced virus production 15-fold. Cells were monitoring periodically for viability by Trypan Blue assay. To test their ability to produce virus after this sustained exposure, at day 15 the N16-treated cells were washed, fresh media without inhibitor was added and the cells were incubated 4 days longer (to day 19). The supernatant was collected, the cells were washed again and then incubated for another 4 days in media with inhibitor, adding fresh inhibitor daily. The final supernatant was collected on day 23. The virus level surged by 10-fold when N16 was removed indicating that the observed inhibition was not attributed to irreversible cell toxicity. It then plummeted by 50-fold upon re-addition of N16, indicating that the virus was still susceptible. Thus, the cells maintained the ability to produce virus and the virus in the population at 15 days was essentially as susceptible to N16 as the initial virus population used to infect the Jurkat cells. Number of independent trials: n=2.

Figure 17B:
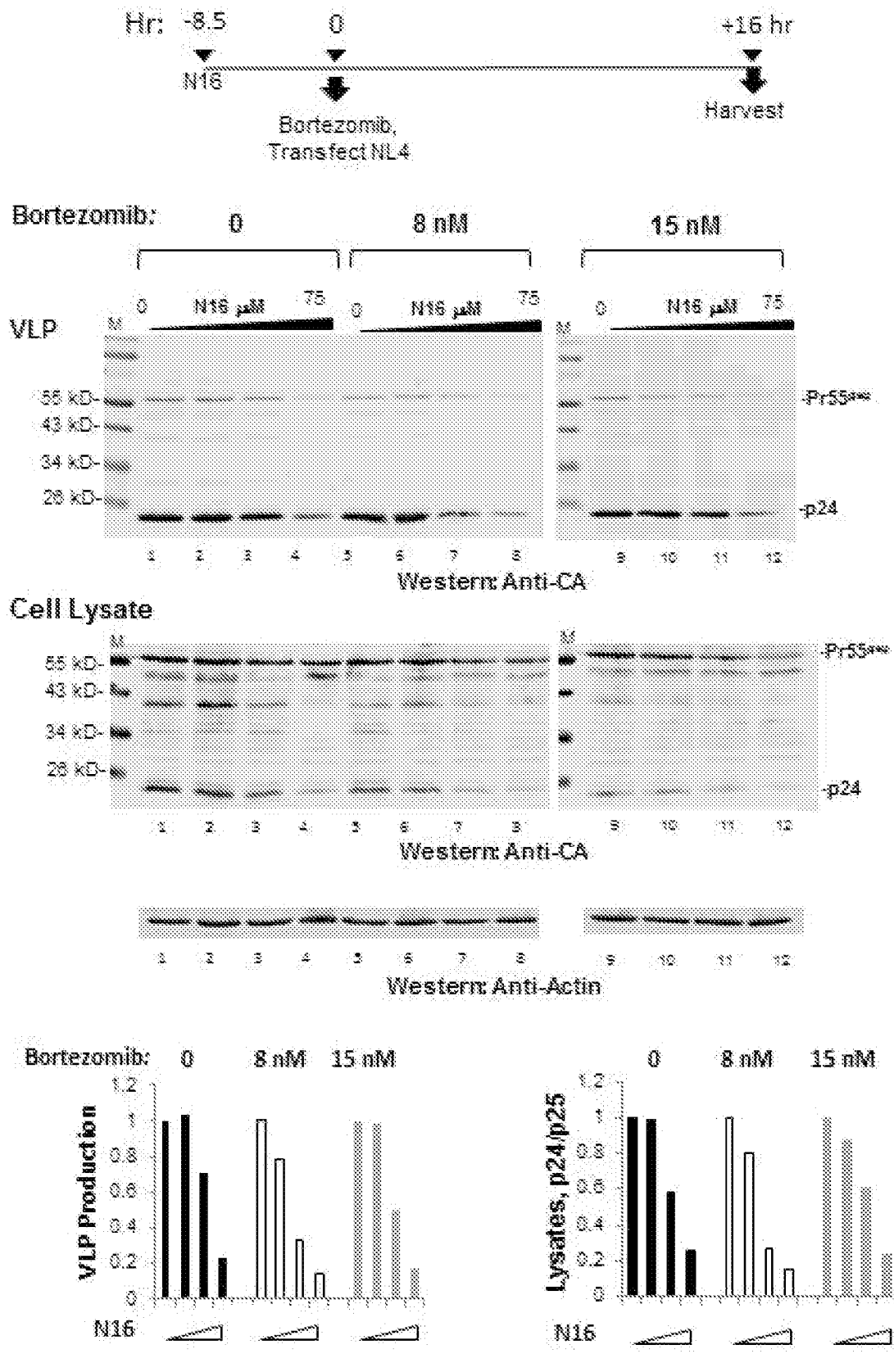
Figure 17C:
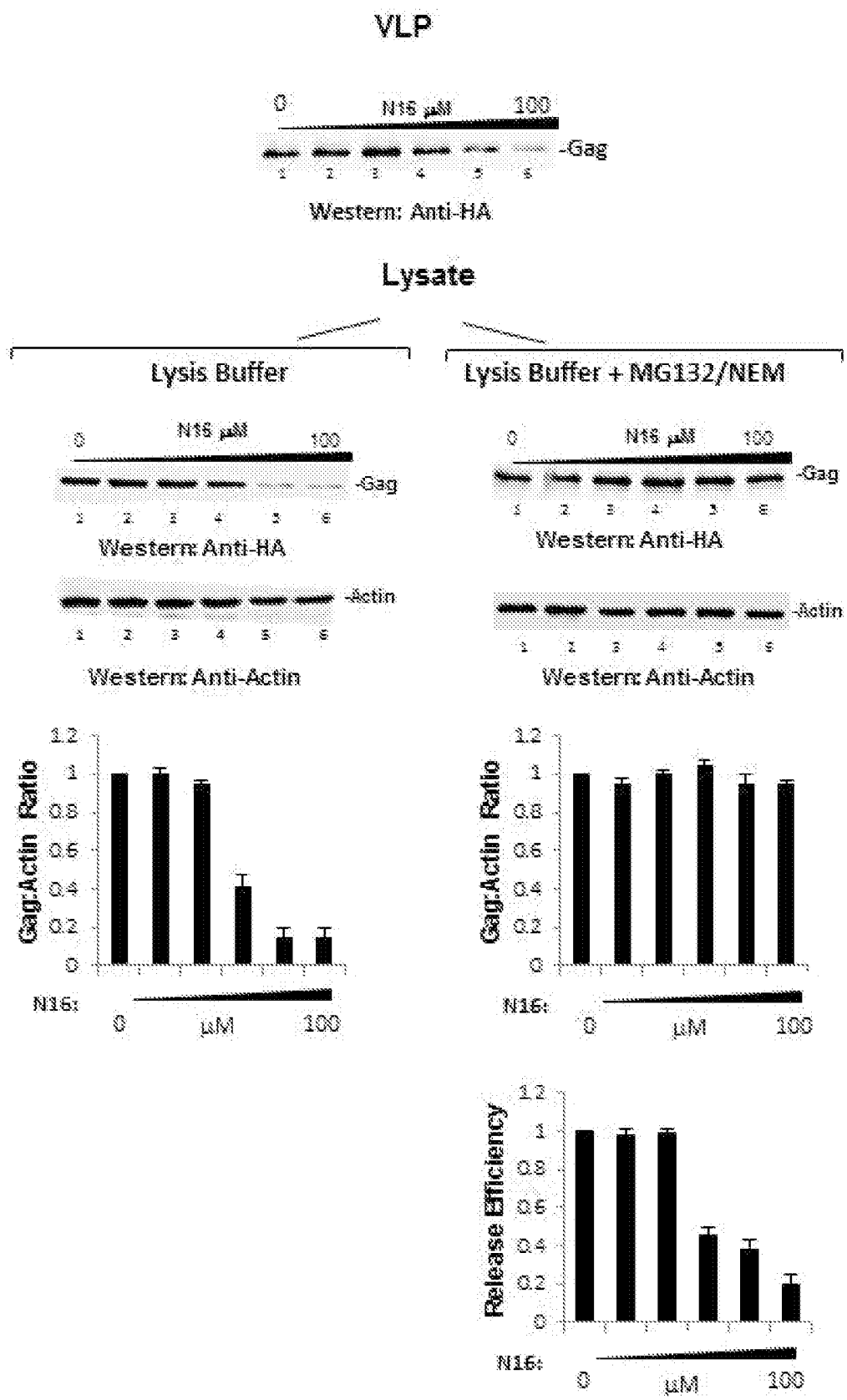

FIG. 17A-C. A) Effect of N16 on Gag VLP production and Gag steady-state in 293T and HieLa cells. Top, Cells treated with 0, 50, 100, and 150 μM N16 were transfected with DNA encoding Gag-HA. At the end of the treatment period, tissue culture media was removed for VLP isolation. Cells were suspended in lysis buffer. Blots were probed for Gag-HA and actin. Bottom, Quantitative analysis. Relative effects of N16 on VLP and SI Gag. B) Effect of 'in cellulo' bortezomib on N16-mediated interference with VLP production and Gag steady-state. Top, Schematic diagram summarizing experimental protocol. Previous studies found proteasome inhibition at ≥5 nM (Gelman et. al.) and an IC50 of about 10 nM at 16 hrs. Our results were similar with an IC50 for bortezomib of 12 to 22 nM at a 95% confidence level (data not shown). Center, Western analysis of isolated virus and cell lysates. Cells were exposed to 0, 25, 50, and 75 uM N16 for 8 to 9 hr prior to transfection with DNA encoding pNL4-3ΔEnv and bortezomib at 0 (lanes 1-4), 8 (lanes 5-8) or 15 (lanes 9-12) nM. Sixteen hr later, the media was removed for VLP isolation and the cells were washed and lysates prepared. The wash and cell lysis buffers contained bortezomib at 10 nM as it is a reversible inhibitor. Bottom, Quantitative analysis. Panel C) Effect of 'ex cellulo' treatment with proteasome inhibitor MG132 and NEM on N16-mediated interference with Gag steady-state. Top, Cells treated at the indicated concentration were transfected with DNA encoding Gag-HA. At the end of the treatment period, tissue culture media was removed for VLP isolation. Center, Cells were either suspended in lysis buffer (Left) or incubated 1 hr further in media containing 25 μM MG132 and 10 μM NEM and then suspended in lysis buffer containing 25 μM MG132 and 10 μM NEM. Blots were probed for Gag-HA and actin. Bottom, Quantitative analysis, Ratio of Gag to actin normalized to the mock-treated control (0 μM N16). VLP release efficiency was determined as the ratio of [Gag signal in VLP]/[Gag signal in VLP+Gag signal in cell lysate prepared with MG132/NEM]. Values were normalized to that of the mock-treated control. A), n=2; B), n=1; C), n=2.

FIG. 18A-C. Localization of endogenous Tsg101+/−N16. Upon reaching the typical confluency used in experiments above, the tissue culture media was removed from 10 cm plates of 293T cells and replaced with media containing either 50 uM N16 or the DMSO vehicle. After a 24 hr treatment period, cells were harvested and suspended in hypotonic buffer, Dounce homogenized and the homogenate subjected to differential centrifugation to obtain subcellular fractions that we have characterized in Goff et al. Homogenates were centrifuged at 1000×g to remove nuclei and cell debris (P1) from a post-nuclear supernate (S1) which was further centrifuged at 27,000×g to pellet endosomes and lysosomes (P2) yielding a supernate (S2) which was further centrifuged at 100,000×g to separate PM-derived microsomes and small vesicles (P3) from non-membrane-bound cytosolic proteins (S3). Pellet fractions were resuspended in RIPA to the original homogenate volume. Fractions obtained from DMSO—A) and N16—B) treated cells were analyzed by Western for endogenous Tsg101. Semi-quantitative analysis C) showed an essentially identical localization for Tsg101 in control- and drug-treated cells. n=2.

FIG. 19A-F. N16 (50 μM) prevents co-localization of Gag and Tsg101 on the plasma membrane. A-E) Fluorescence microscopy images of cells that co-express Tsg101-Myc alone or GagWT-GFP and Tsg101-Myc. Cells grown on coverslips were co-transfected with DNA encoding Tsg101-Myc (A) or Tsg101-Myc and GagWT-GFP (B, D and E) or GagP7L-GFP (C) and treated with F15 (D) or N16 (E). After 24 hr the coverslips were processed for microscopy with Tsg101-Myc detected with anti-Myc antibody and Texas Red secondary antibody as described in Materials & Methods. A) Tsg101-Myc in cells treated with DMSO carrier (top) or N16 (bottom). B-E), Top panels, show signal from Gag-GFP; middle panels, images showing Tsg101-Myc signal; bottom panels, merged images showing signals from Gag-GFP and Tsg101-Myc. Boxes frame a region of the plasma membrane. F) Pearson's coefficient of correlation values determined for the images shown. Error bars indicate the highest values obtained for similar samples. n=6.

Figure 20C:
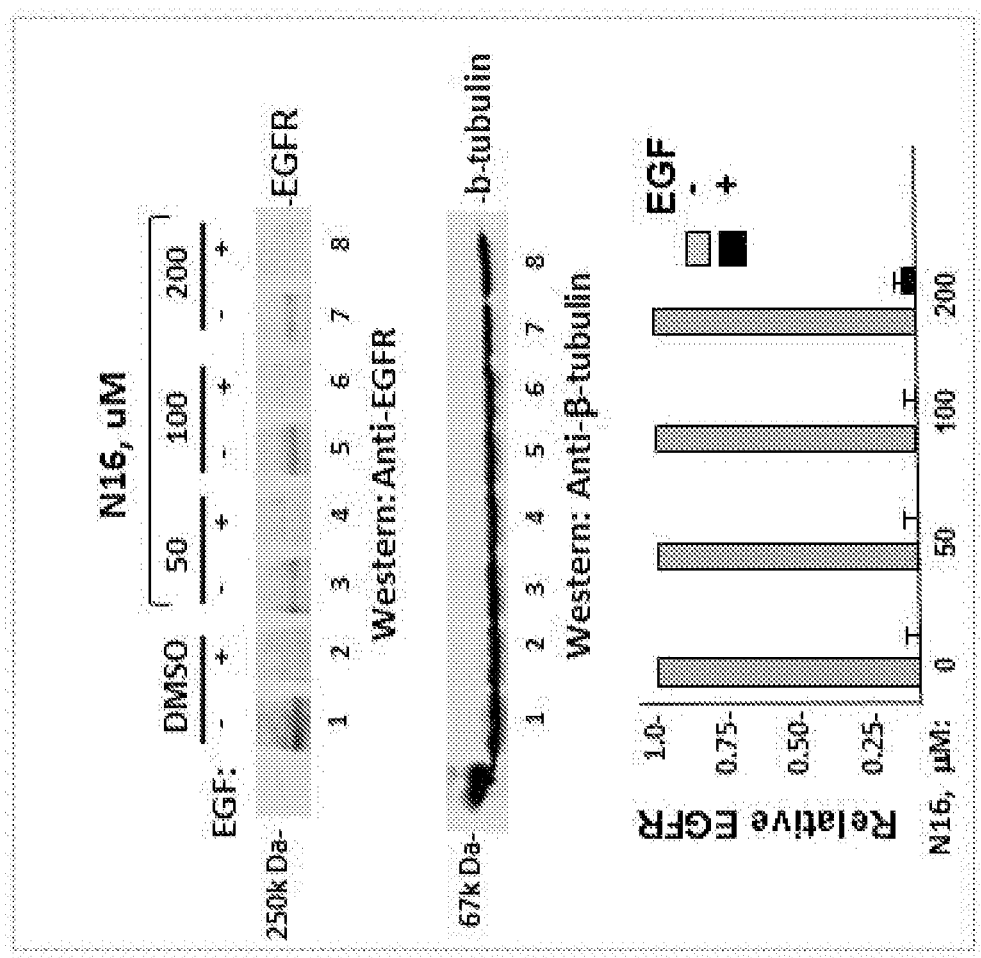

FIG. 20A-C. N16 inhibition is virus-specific. A) N16 IC50 for Hela and 293T cells. At 95% confidence levels, the IC50 values for Hela and 293T were 156-205 uM and 99.8-139.4 uM, respectively (Prism 6, Graph Pad Software Inc.). Values were calculated by measuring metabolic activity (WST-1 Assay, Roche Applied Science) after cells were grown for 24 hr in N16. Data points represent the mean of 2 assays, 3 time points each for each cell line. B) The frequency of cells exhibiting Tsg101 midbody localization in 200 cells sampled was determined. Values in the absence or presence of N16 (50 uM) were 12% and 13%, respectively). C) N16 effect on EGF-stimulated EFGR degradation. Cells maintained for 24 hr in media containing DMSO alone or DMSO and N16 were stimulated with EGF ligand for a 90 min period and then assessed for EGFR steady-state level by Western analysis. EGFR levels for unstimulated and stimulated sample pairs are shown. A) n=2; B) n=2; C) n=2.

Figure 21A:
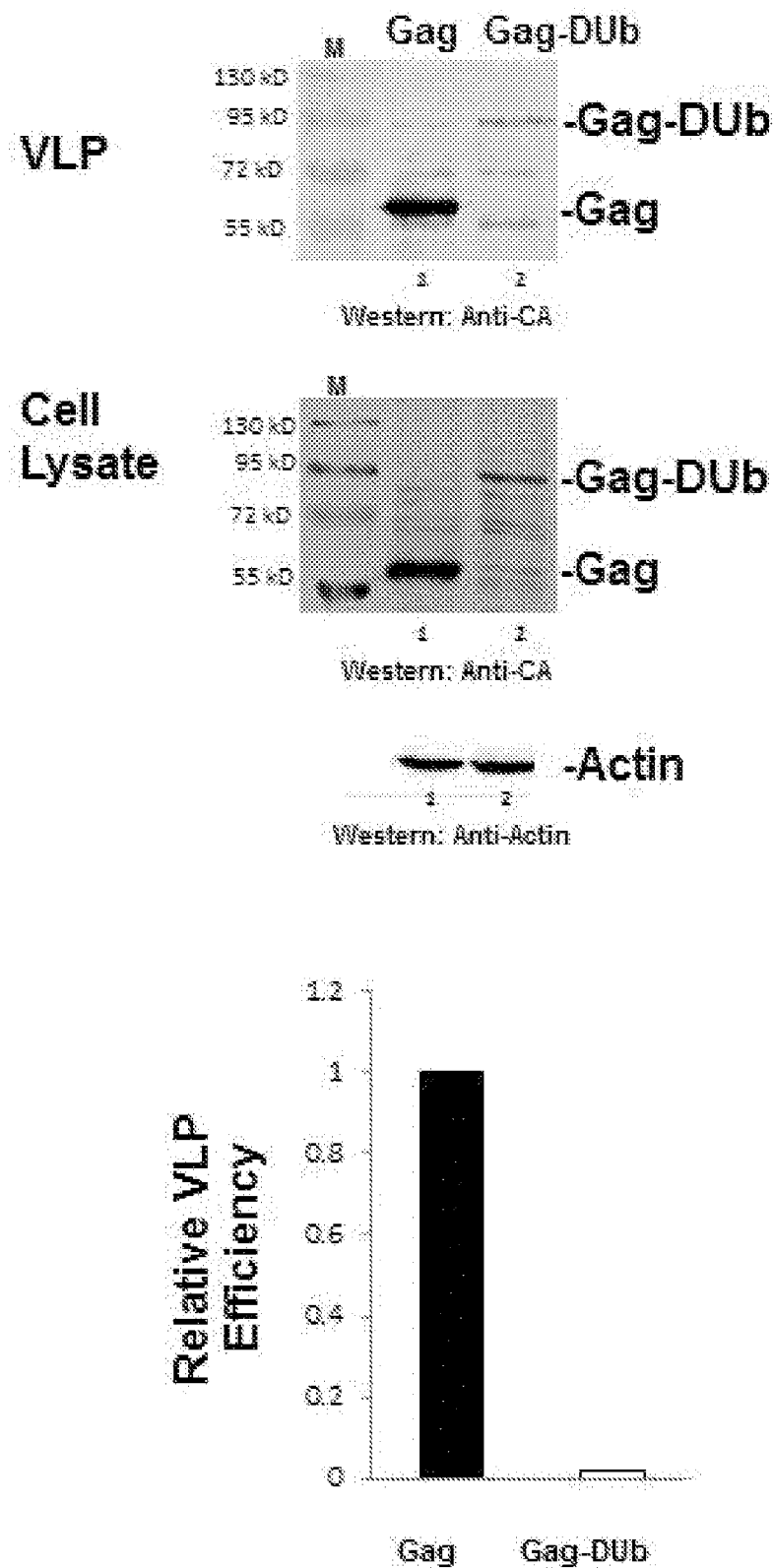
Figure 21B:
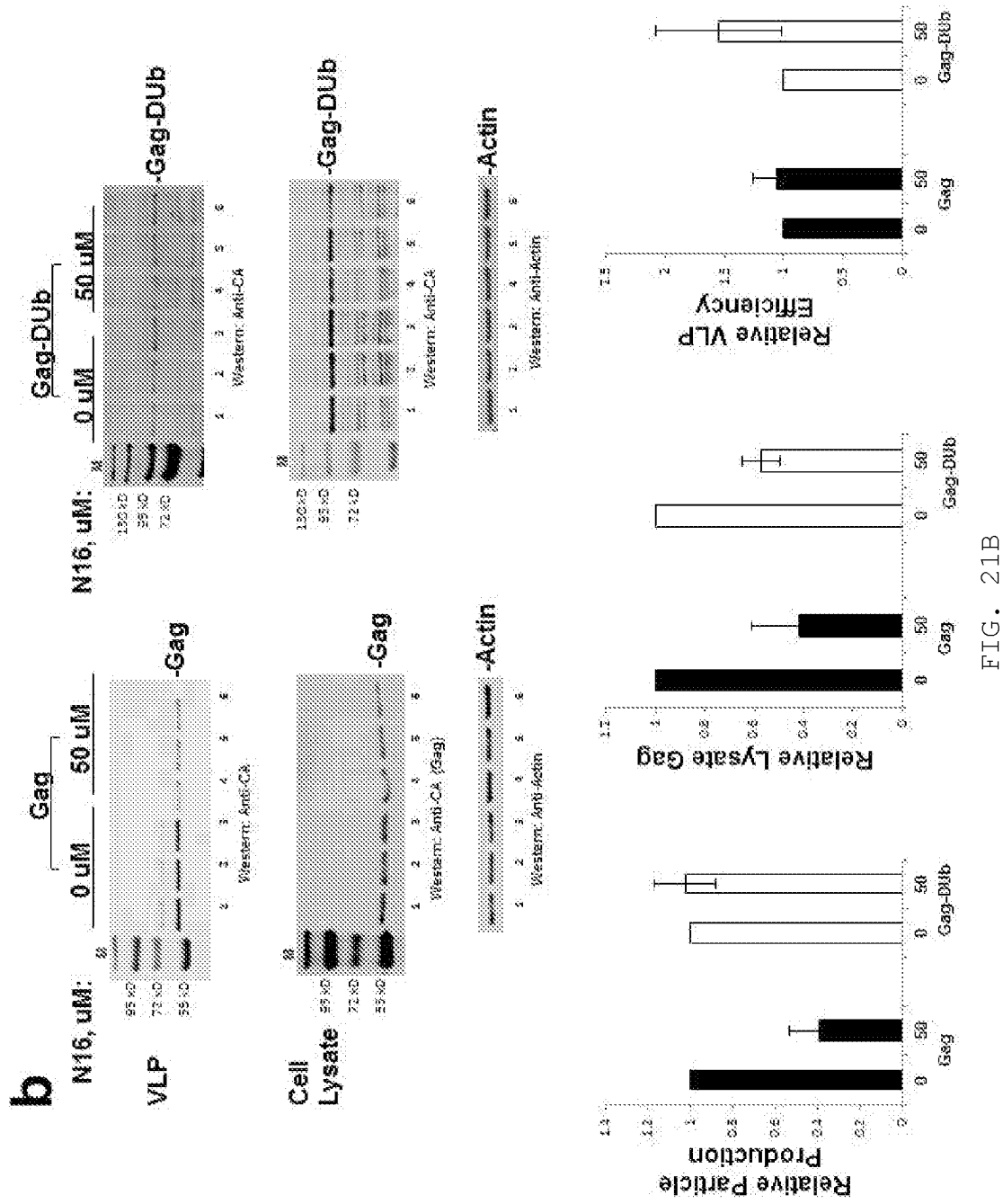

FIG. 21A-B. N16 suppresses the inhibitory effect of fusing DUb to Gag. A) 293T cells were transfected with DNA encoding Gag or Gag-DUb. After 24 hr, tissue culture media was removed for VLP isolation and cell lysates were prepared. Top, Western blot analysis of Gag in cushioned VLP samples; Middle, Gag and actin in cell lysates; Bottom, Quantitative analysis of VLP release efficiency normalized to the WT Gag control (Gag and Gag-DUb differed in sample size in order to yield visible signal); B) Effect of N16 on Gag and GagDUb VLP production. Top, Western blot analysis; Triplicate samples are shown to demonstrate reproducibility. Bottom, Quantitative analysis of VLP production (left), lysate Gag (center) and VLP release efficiency (right) normalized to the mock-treated control. Number of independent assays: n=3

FIG. 22A-H. Solution NMR reveals that N16 interferes with Ub binding to Tsg101 UEV domain. A) 100 structures of the N16-Tsg101 UEV complex were calculated. B) Enlarged depiction of the lowest energy structure of Tsg101 UEV with N16 and binding site residues shown as spheres and sticks. NMR restraints and structural statistics are described in FIG. 14. C), E), G) Structure of Tsg101 UEV domain using a surface representation in white (PDB ID: 1KPP) with large chemical shift perturbations (>1.5 standard deviations from zero) upon addition of N16 (C), Gag PTAP peptide (E), and ubiquitin (G). D), F), H) Residue-specific chemical shift perturbations of Tsg101 UEV following incubation with N16 (D); PTAP (F); Ub (H), all shown with black circles and lines. Large chemical shift perturbations are above the dotted grey line (>1.5 standard deviations from zero). Circles and lines in (F) and (H) represent pre-incubation with N16 before addition of PTAP (F) or Ub (H).

Figure 23:
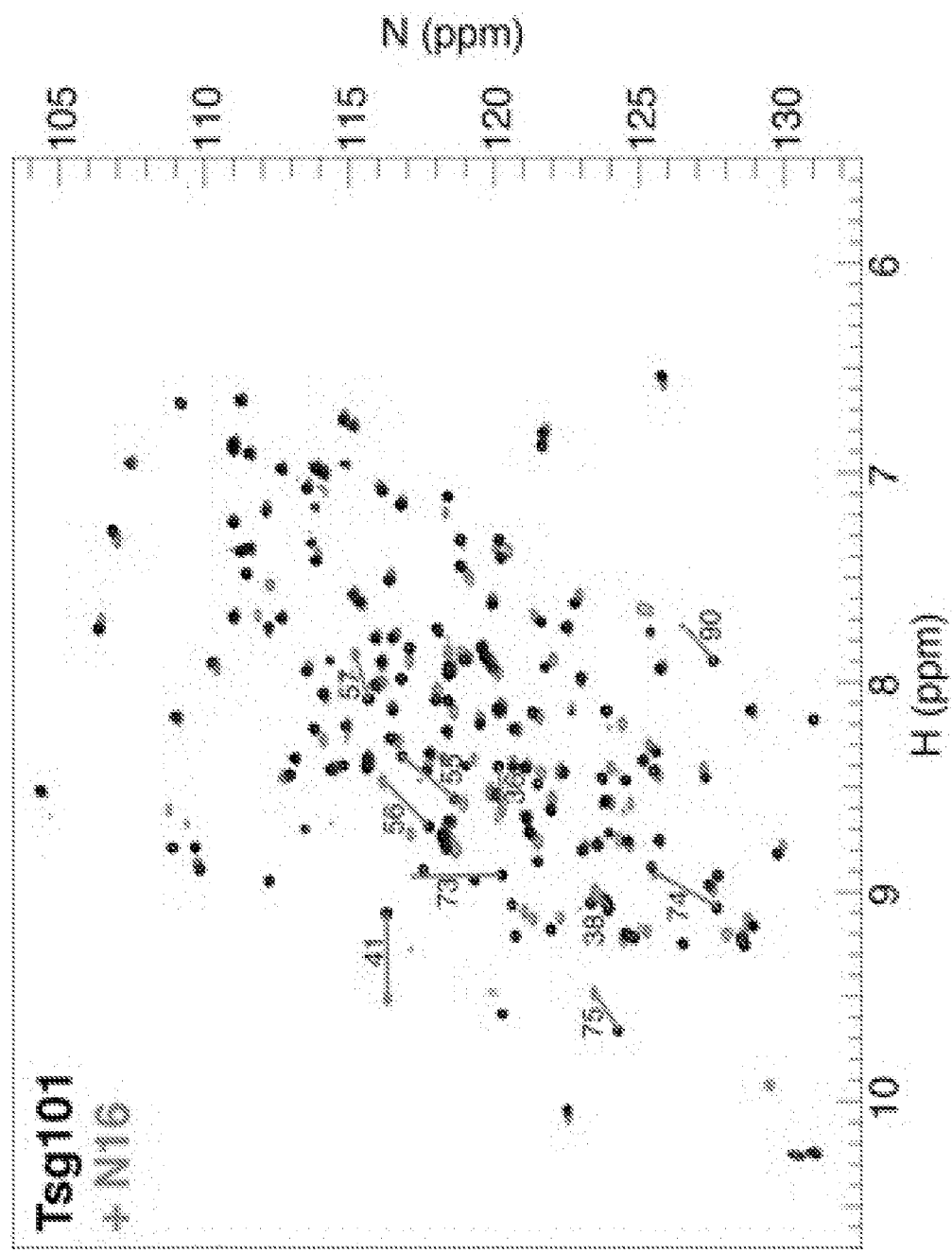

FIG. 23. HSQC spectra of the Tsg101 UEV domain in the presence and absence of N16. 15N-Tsg101 UEV HSQC spectrum in the absence of N16 (excess N16 and DMSO removed by ultrafiltration). The ten largest chemical shift perturbations are highlighted with residue numbers. Stars indicate the location of residues C73 and K90, which are broadened in the presence of N16.

FIG. 24A-B. HSQC spectra of the Tsg101 UEV domain in complex with the PTAP peptide, in the presence and absence of N16. A) 15N-Tsg101 UEV HSQC spectrum in the absence and presence of PTAP at a 1:1 ratio. The ten largest chemical shift perturbations are highlighted with residue numbers. B) As in A) but with pre-incubation of N16.

FIG. 25A-B. HSQC spectra of the Tsg101 UEV domain in complex with ubiquitin, in the presence and absence of N16. A) 15N-Tsg101 UEV HSQC spectrum in the absence and presence of Ub at a 1:1 ratio. The ten largest chemical shift perturbations are highlighted with residue numbers. B) As in A) but with pre-incubation of N16.

FIG. 26A-D. N16 binds covalently to C73 in the Tsg101 UEV domain. A) Activation of N16 to reactive sulfenamide. N16 (i) is converted to intermediates sulfenic acid (ii) and sulfenamide (iii) through acid catalysis to yield a covalently attached N16-Tsg101 UEV complex (iv). B) HNCACB Cβ regions for residues C73, L74, I86 and C87 of Tsg101 without (−) and with (+) N16. C) Examination by fluorescence microscopy of cells co-expressing GagWT-GFP and Tsg101WT-Myc, Tsg101C73A-Myc or Tsg101C87A-Myc in the absence and presence of 50 µM N16. n=3 D) Pearson's coefficient of correlation values.

Figure 27A:
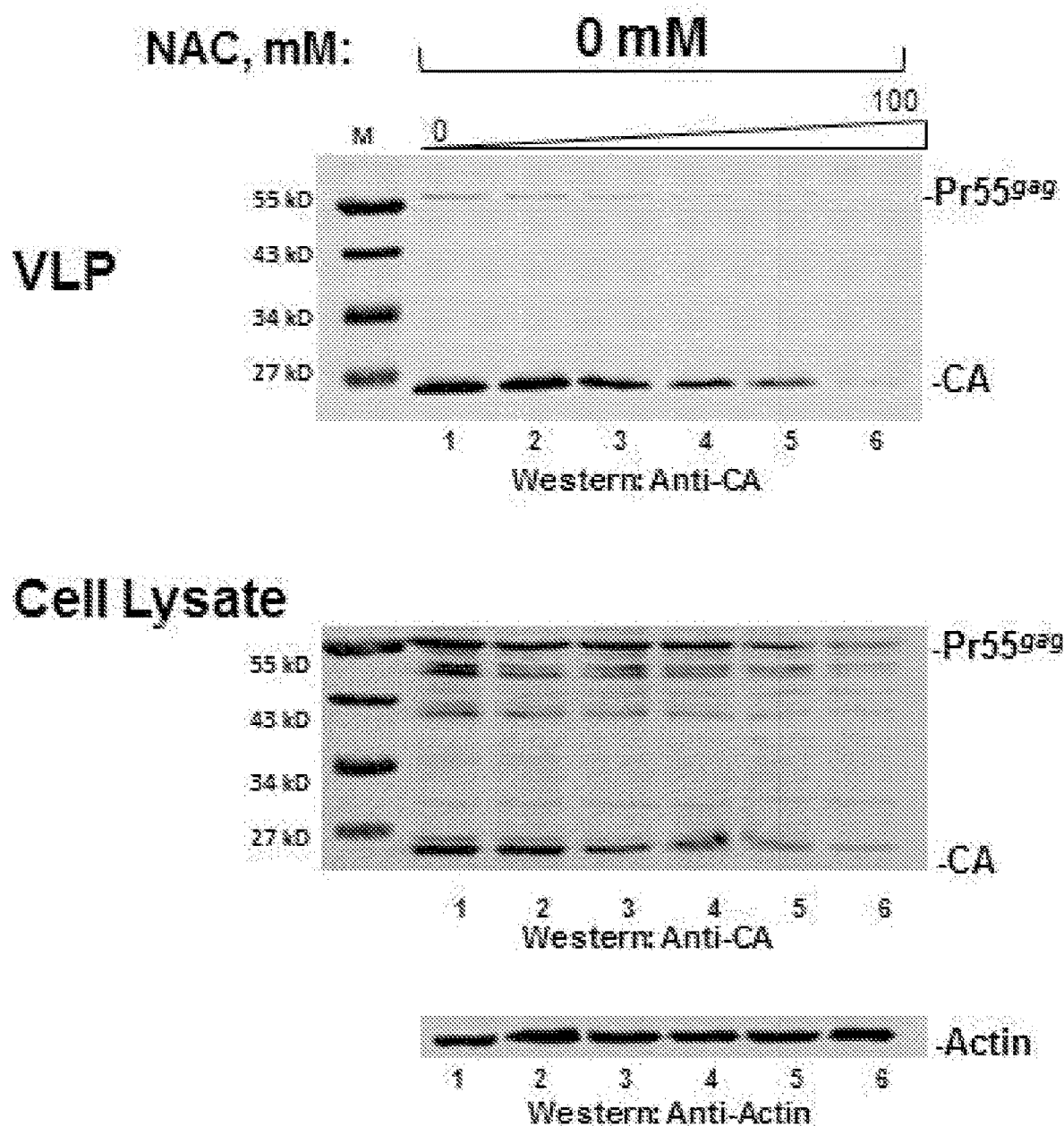
Figure 27B:
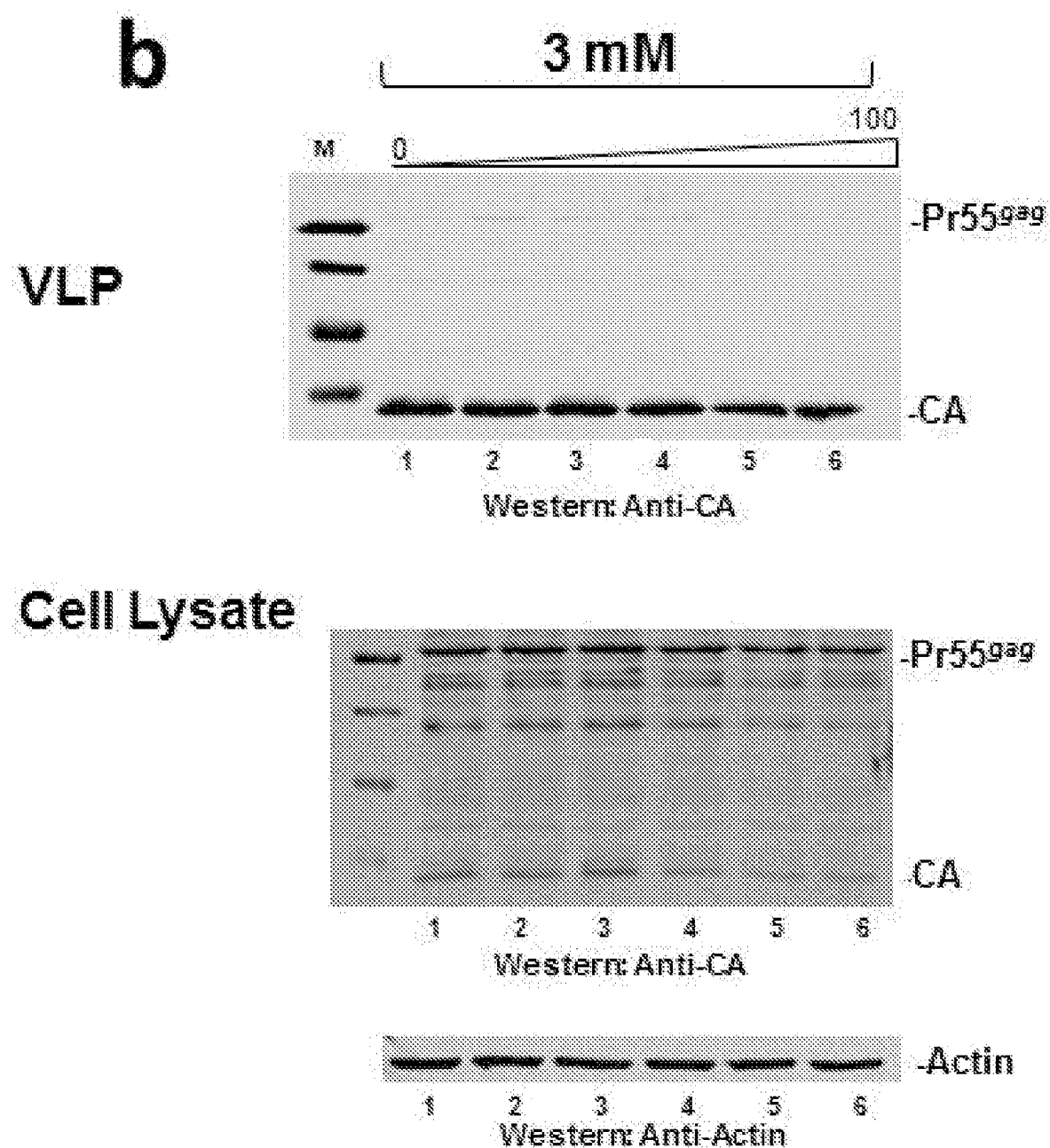
Figure 27C:
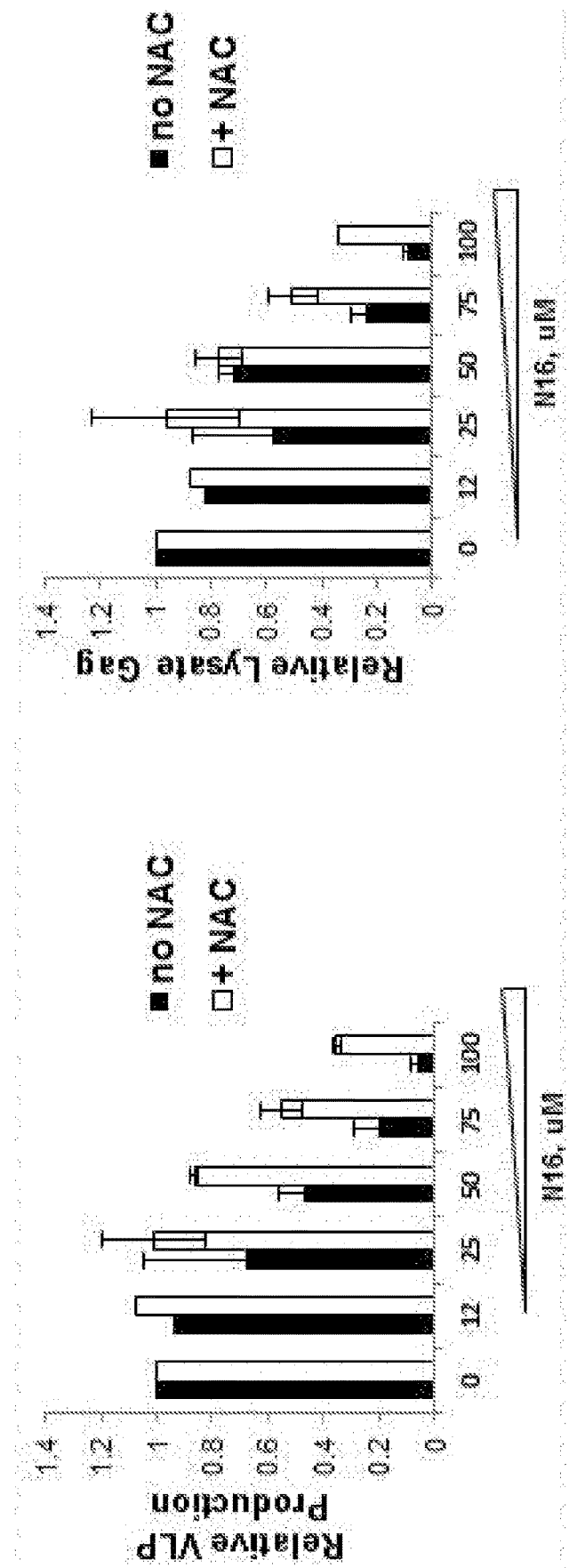

FIG. 27A-C. Effect of N-Acetyl Cysteine (NAC) on N16-mediated inhibition of VLP production and intracellular Gag accumulation. Metabolic measurements (Roche WST-1 reagent) indicated that 293T cells were robust up to at least 4 mM NAC. A concentration of 3 mM NAC was therefore used to test the effect of the antioxidative reagent on the N16 inhibitory effect. N16 (0, 12, 25, 50, 75, and 100 uM) was added 8.5 hr prior to transfection with pNL4-3ΔEnv. Cells were harvested 16 hr later. A) Dose-dependent inhibition of VLP production (Top panel) and intracellular Gag accumulation (Bottom panel) by N16. B) Suppression of the N16 inhibitory effect by 3 mM NAC. C) Quantitative analysis. n=2.

Figure 28C:
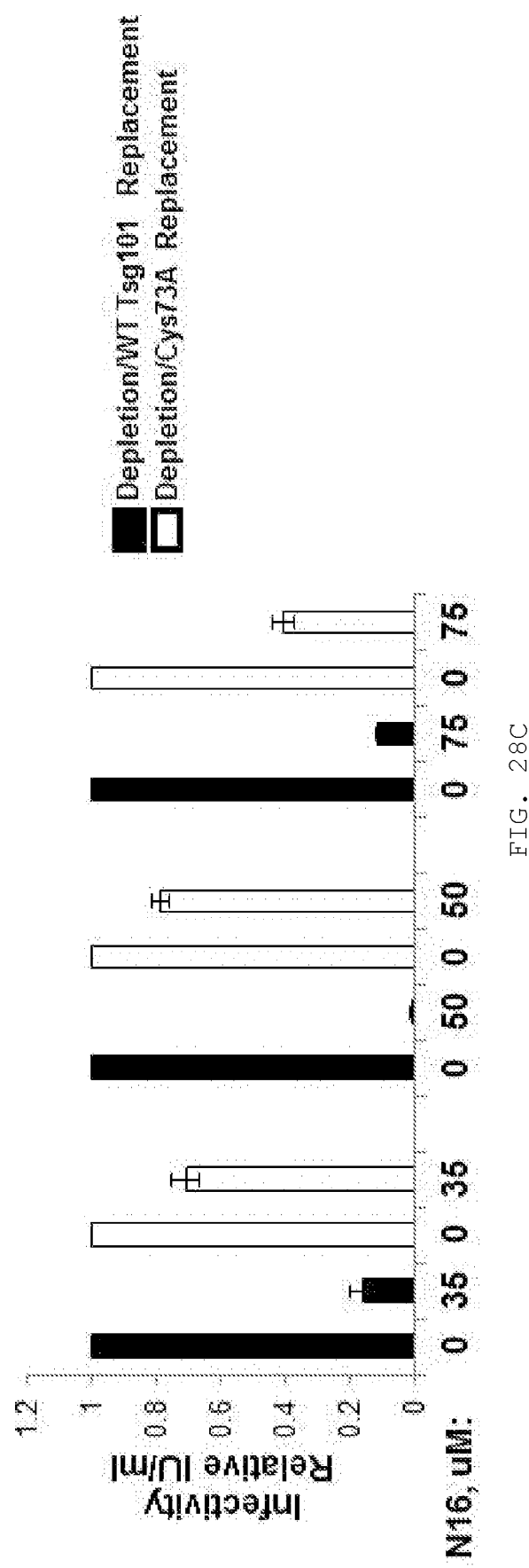

FIG. 28A-C. N16 inhibition is suppressed by replacing endogenous Tsg101 with the Tsg101-C73A mutant. A) Schematic diagram summarizing experimental protocol. 293T cells were transfected with non-targeting siRNA or siRNA targeting Tsg101. Thirty minute later, cells treated previously with the targeting siRNA were transfected with siRNA-resistant replacement Ts101 constructs (RWT or RC73A). Eighteen hours later, all cells were treated with the DMSO control or with 50 uM N16. Six hours later, all cells were co-transfected with HIV-1 pNL4-3 delta env+HIV-1 IIIB-env constructs and additional siRNA. Tissue culture media was collected 24 hr post-DNA transfection, filtered and examined for virus production. B) Western analysis showing Tsg101 steady-state level following depletion (Left) or Replacement (Right). The targeted siRNA reduced the steady-state level of Tsg101 in the cell lysate compared to the level in mock-treated cells or cells transfected with the non-targeting control siRNA. The specificity of the siRNAs was indicated by the finding that the actin level was not affected. C) Quantification of released viral particles following replacement with WT (Left) or C73A (Right), replacement as measured by the MAGI assay. In the cells where siRNA-resistant WT Tsg101 was expressed following targeted siRNA depletion, N16 reduced the amount of infectious units in the MAGI assay. Less N16 inhibition was observed following replacement with the siRNA-resistant C73A Tsg101 variant. The results support the conclusion that C73 is a critical residue for the antiviral effect. (n=2).

DETAILED DESCRIPTION OF THE INVENTION

The present invention provides a method of inhibiting release of a virus from a cell, comprising contacting the cell with a compound that binds an ubiquitin E2 variant (UEV)

domain of a cellular polypeptide, or fragment thereof, with an affinity sufficient to inhibit or disrupt the binding of the cellular polypeptide, or fragment thereof, to ubiquitin.

In an embodiment, the compound binds the UEV domain of the cellular polypeptide, or fragment thereof, with an affinity sufficient to inhibit or disrupt formation of an associative complex comprising the cellular polypeptide, or fragment thereof, that includes the UEV domain Ub-binding pocket, and:

a) an ubiquitin-modified polypeptide of the virus, or fragment thereof, that is capable of binding said UEV domain Ub-binding pocket; or b) an ubiquitin-modified cellular polypeptide for the virus' production other than the cellular polypeptide that includes the UEV domain Ub-binding pocket, or fragment thereof, that is capable of binding said UEV domain Ub-binding pocket.

In an embodiment, the associative complex comprises a) the cellular polypeptide, or fragment thereof, that includes the UEV domain Ub-binding pocket and b) an ubiquitin-modified cellular polypeptide for the virus' production other than the cellular polypeptide that includes the UEV domain Ub-binding pocket, or fragment thereof, that is capable of binding said UEV domain Ub-binding pocket.

In an embodiment, the associative complex further comprises a) an ubiquitin-modified polypeptide of the virus, or fragment thereof, that is capable of binding said UEV domain Ub-binding pocket.

In an embodiment, the compound disrupts at least 50% of the binding of the UEV domain of the cellular polypeptide, or fragment thereof, to ubiquitin.

In an embodiment, the compound is present at a concentration of 1-200 μM, preferably the compound is present at a concentration of 10-150 μM, more preferably the compound is present at a concentration of 15-100 μM, even more preferably the compound is present at a concentration of about 25 μM.

The present invention also provides a method of treating a patient infected with a virus, comprising administering to the patient a compound which binds to the UEV domain Ub-binding pocket of a cellular polypeptide in an amount effective to inhibit the binding of the cellular polypeptide to ubiquitin.

In an embodiment, the cellular polypeptide that includes the UEV domain Ub-binding pocket is TSG101.

In an embodiment, the virus is an enveloped virus.

In an embodiment, the virus is not known to have an L-domain motif, wherein the L-domain motif is any one of $PPX_nY$, PTAP or $LYPX_nL$.

In an embodiment, the virus is at least one of Hepatitis C virus, Human Papillomavirus, Herpes Simplex virus type 1, Dengue virus, Japanese Encephalitis virus, Human Parainfluenzavirus Type 1, or Epstein Barr Virus.

In an embodiment, the virus is known to have an L-domain motif, wherein the L-domain motif is any one of $PPX_nY$, PTAP or $LYPX_nL$.

In an embodiment, the virus is at least one of Human Immunodeficiency virus type 1 (HIV-1), Influenza virus or Human cytomegalovirus.

In an embodiment, the virus is at least one of Zika virus, Dengue virus, Epstein Barr virus, Influenza virus or Measles virus.

In an embodiment, the virus is at least one of Human Immunodeficiency virus type 1 (HIV-1), Human Papillomavirus or Herpes Simplex virus type 1.

In an embodiment, the virus is at least one of Mopeia virus, Tacaribe virus, Human Parainfluenzavirus Type 1, Dengue virus, Hepatitis C virus, Japanese Encephalitis virus, Herpes Simplex virus, Epstein-Barr virus and Human Cytomegalovirus.

In an embodiment, the virus is not an enveloped virus.

In an embodiment, the virus is at least one of Polio virus or Human Papilloma virus.

In an embodiment, the compound is:

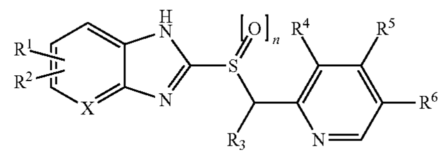

wherein:

$R^1$ is H, halogen, $C_{1-6}$ alkyl unsubstituted or substituted with halogen, $C_{1-8}$ alkoxy unsubstituted or substituted with fluorine or a cycloalkyl group of 3-6 carbon atoms, chlorodifluoromethoxy, fluoroalkyloxy, $C_{1-6}$ alkoxycarbonyl or carboxyl group, or alkanoyl;

$R^2$ is H, halogen, $C_{1-6}$ alkyl unsubstituted or substituted with halogen, $C_{1-6}$ alkoxy unsubstituted or substituted with fluorine, $C_{1-6}$ alkoxycarbonyl or carboxyl group, or alkanoyl;

$R^3$ is H, methyl or ethyl;

$R^4$ is H, $C_{1-6}$ alkyl, $C_{1-3}$ alkoxy, methoxyethoxy, or ethoxyethoxy;

$R^5$ is H, methyl, $C_{1-5}$ alkoxy unsubstituted or substituted with fluorine, methoxyethoxy, ethoxyethoxy, or $—OC_{2-10}$ alkyl-$OC_{0-6}$ alkyl;

$R^6$ is H, $C_{1-3}$ alkyl, $C_{1-3}$ alkoxy, methoxyethoxy, or ethoxyethoxy;

n is 0-2; and

X is C, C—$R^1$ or —$R^2$, or N.

In an embodiment, the compound is:

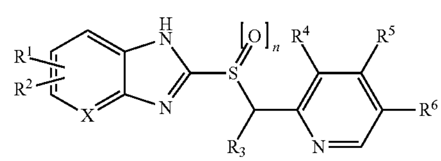

wherein:

$R^1$ is halogen, $C_{1-6}$ alkyl substituted with halogen, chlorodifluoromethoxy, or $C_{3-6}$ alkoxycarbonyl or carboxyl group;

$R^2$ is halogen, $C_{1-6}$ alkyl substituted with halogen, $C_{1-6}$ alkoxy unsubstituted or substituted with fluorine, or $C_{3-6}$ alkoxycarbonyl or carboxyl group;

$R^3$ is H;

$R^4$ is $C_{2-6}$ alkyl or $C_3$ alkoxy;

$R^5$ is $C_{3-5}$ alkoxy unsubstituted, $C_{2-5}$ alkoxy substituted with fluorine, or $—OC_{2-10}$ alkyl-$OC_{0-6}$ alkyl;

$R^6$ is $C_{2-3}$ alkyl or $C_3$ alkoxy;

n is 0-2; and

X is C, or C—$R^1$ or —$R^2$.

In an embodiment, $R^1$ is $C_{1-8}$ alkoxy unsubstituted or substituted with a cycloalkyl group of 3-6 carbon atoms or fluoroalkyloxy;

$R^2$ is H;

$R^3$ is H;

$R^4$ is H or methyl;

$R^5$ is H, methyl or methoxy;
$R^6$ is H or methyl;
n is 1; and
X is N.
In an embodiment,
$R^1$ and $R^2$ are independently H, $C_{1-6}$ alkyl, halogen, methoxycarbonyl, ethoxycarbonyl, alkoxy, or alkanoyl;
$R^3$ is H, methyl, or ethyl;
$R^4$-$R^6$ are independently H, methyl, methoxy, ethoxy, methoxyethoxy, or ethoxyethoxy, wherein $R^4$-$R^6$ are not all hydrogen, and wherein if two of $R^4$-$R^6$ are hydrogen, then the remaining group is not methyl;
n is 1; and
X is C, or C—$R^1$ or —$R^2$.
In an embodiment,
$R^1$ is $C_{1-3}$ alkoxy substituted with fluorine, or chlorodifluoromethoxy;
$R^2$ is H, halogen, trifluoromethyl, $C_{1-3}$ alkyl, or $C_{1-3}$ alkoxy unsubstituted or substituted with fluorine;
$R^3$ is H;
$R^4$ and $R^6$ are independently H, $C_{1-3}$ alkyl, or $C_{1-3}$ alkoxy, wherein $R^4$ and $R^6$ are not the same and wherein one of $R^4$ and $R^6$ is $C_{1-3}$ alkoxy;
$R^5$ is $C_{1-3}$ alkoxy;
n is 0 or 1; and
X is C, or C—$R^1$ or —$R^2$.
In an embodiment,
$R^1$ is H, methoxy, or trifluoromethyl;
$R^2$ is H;
$R^3$ is H;
$R^4$ and $R^6$ are independently H or methyl;
$R^5$ is $C_{2-5}$ alkoxy substituted with fluorine;
n is 0 or 1; and
X is C, or C—$R^1$ or —$R^2$.
In an embodiment,
$R^1$ and $R^2$ are independently H, halogen, $C_{1-6}$ alkyl unsubstituted or substituted with halogen, $C_{1-6}$ alkoxy, or $C_{1-6}$ alkoxycarbonyl or carboxyl group;
$R^3$ is H;
$R^4$ is $C_{1-6}$ alkyl;
$R^5$ is —$OC_{2-10}$ alkyl-$OC_{0-6}$ alkyl;
$R^6$ is H;
n is 0-2; and
X is C, or C—$R^1$ or —$R^2$.
In an embodiment, the compound has the structure:

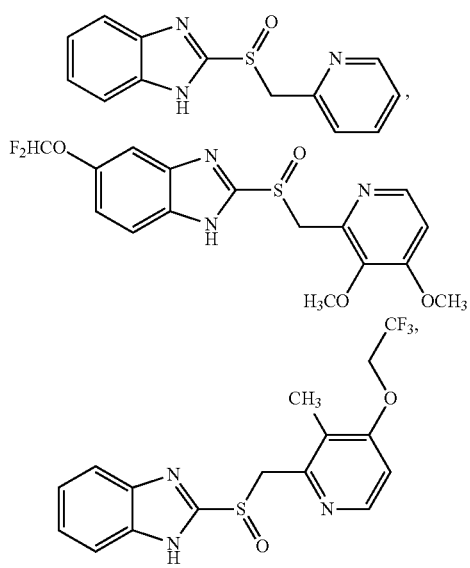

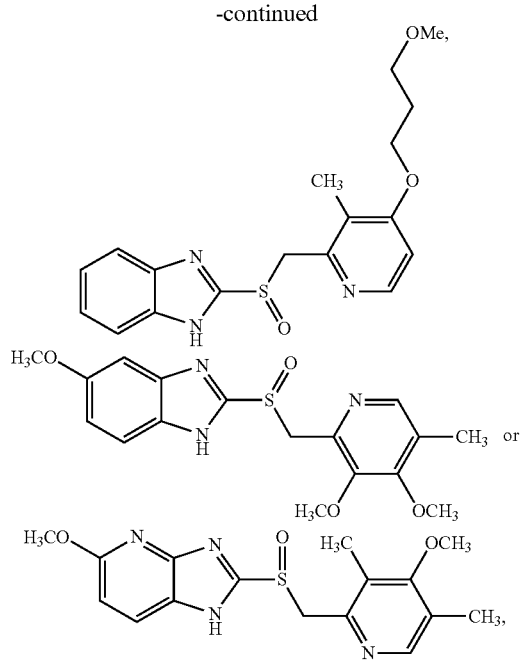

or a pharmaceutically acceptable salt thereof.

In an embodiment, the compound has the structure:

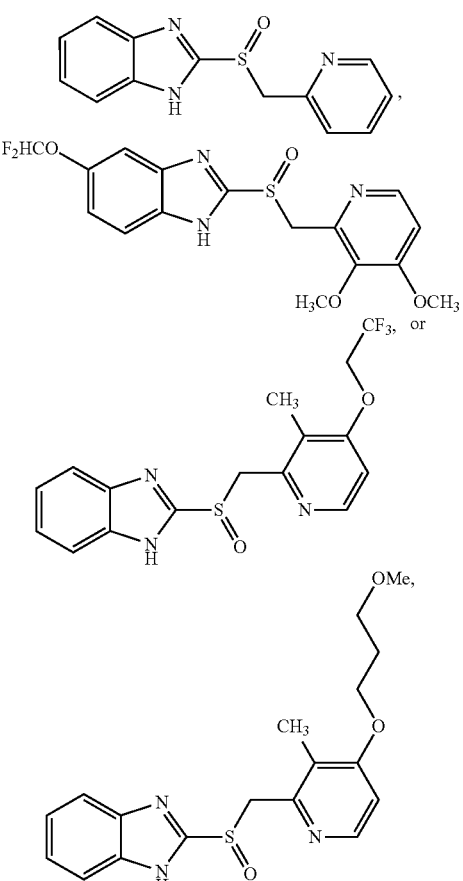

or a pharmaceutically acceptable salt thereof.

In an embodiment, the cell is a human cell.

In an embodiment, the cell is a plant cell.

In an embodiment, the virus is at least one of Tomato Bushy Stunt virus or Brome mosaic virus.

The present invention also provides a method for identifying a compound that binds a UEV domain Ub-binding pocket of a cellular polypeptide with an affinity sufficient to inhibit or disrupt formation of an associative complex in a cell, comprising the steps of:

a) obtaining a test compound;

b) contacting the test compound with a cellular polypeptide, or fragment thereof, including a UEV domain Ub-binding pocket, in the presence of an ubiquitin-modified polypeptide of the virus, or fragment thereof, that is capable of binding said UEV domain Ub-binding pocket, or an ubiquitin-modified cellular polypeptide for the virus' production other than the cellular polypeptide that includes the UEV domain Ub-binding pocket, or fragment thereof, that is capable of binding said UEV domain Ub-binding pocket;

c) determining whether the test compound inhibits or disrupts the formation of an associative complex comprising the cellular polypeptide, or fragment thereof, including a UEV domain Ub-binding pocket and the ubiquitin-modified polypeptide of the virus, or fragment thereof, that is capable of binding said UEV domain Ub-binding pocket, or the ubiquitin-modified cellular polypeptide for the virus' production other than the cellular polypeptide that includes the UEV domain Ub-binding pocket, or fragment thereof, that is capable of binding said UEV domain Ub-binding pocket, thereby identifying the test compound as a compound that binds a UEV domain Ub-binding pocket of a cellular polypeptide with an affinity sufficient to inhibit or disrupt formation of an associative complex in a cell.

The detailed description of embodiments of the invention is made in reference to the accompanying drawings. In describing the invention, explanation about related functions or constructions known in the art are omitted for the sake of clearness in understanding the concept of the invention to avoid obscuring the invention with unnecessary detail.

The present invention relates generally to anti-viral therapeutics that target a factor critical for production of a broad spectrum of viral pathogens, but which will not induce formation of resistant viruses, and in particular, to methods of inhibiting animal viruses using compositions targeting TSG 101-ubiquitin interaction. Some formulations of the therapeutics are deliverable as agents that have already been demonstrated to be safe, well-tolerated, and market acceptable as drugs.

Advantages of the embodiments of the invention described herein include 'First-in-class" anti-TSG101 therapeutics that (1) minimize emergence of drug-resistance by targeting a highly conserved cell-encoded, rather than viral-encoded protein. The use of virus-encoded gene products as targets invariably selects for drug-resistant variants. (2) A further advantage includes delivery of the anti-viral agents as long-acting and sustained release formulations that are anticipated to reduce current problems arising from lack of patient adherence to therapeutic regimens. (3) The formulations in use are already known to be safe, well-tolerated, and market acceptable as drugs for a different indication. (4) An additional advantage includes the fact that the therapeutic composition is highly specific for the target as required by the virus rather than host. (5) Furthermore, the anti-viral therapeutic is broad spectrum as many pathogens require the Tsg101 protein to mediate trafficking functions. (6) Moreover, efficacy does not require direct binding of a viral-encoded protein to the targeted cellular protein. (7) The therapeutic can be presented as a pro-drug, i.e., requiring local formation of an active derivative, thereby reducing possible off-target encounters.

As further described herein, a method is provided for inhibiting a mechanism used by the enveloped virus HIV-1 to prevent internalization and promote its release from the cell. This method includes contacting a cell with a compound having an antiviral activity, said antiviral activity comprises: (i) inhibiting formation of an associative complex; or (ii) weakening formation of an associative complex, wherein the associative complex comprises a mono- or di-ubiquitin (Ub) moiety on any protein, viral-encoded or cellular-encoded, that is required for production of released infectious virus particles and TSG101 or fragment thereof, capable of binding the Ub moiety on a viral or cellular protein.

The mechanism used by the virus to prevent internalization is based on the fact that TSG101 is an intrinsically inactive E2 enzyme and, as such, addition of another Ub moiety to the Ub moiety on the viral/cellular protein to create a polyUb signal is prevented. See FIG. 1.

Figure 2:
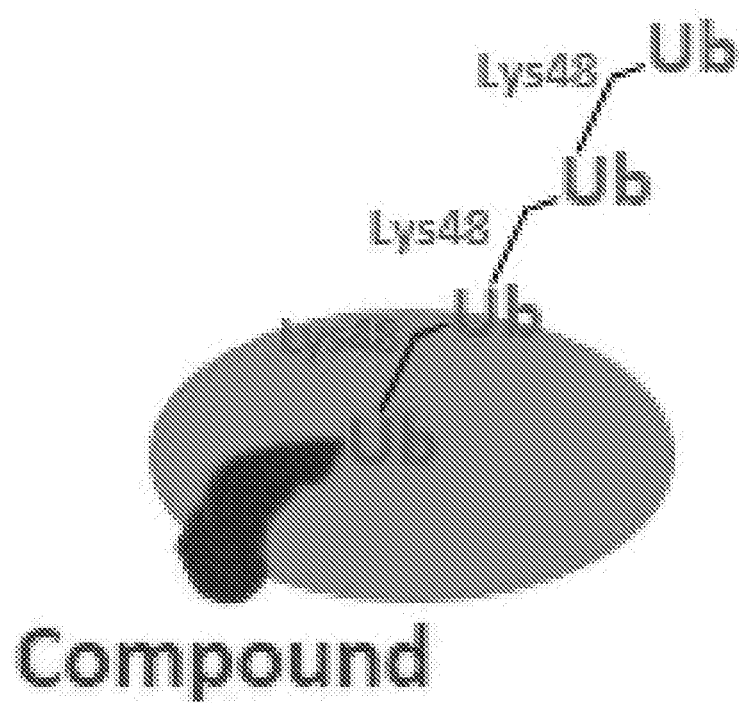
FIG. 2. Compound-induced unwanted polyubiquitination. In a Lys48-linked polyubiquitin chain, ubiquitin moieties are linked as a result of isopeptide formation between Lys48 in the acceptor Ub and the C-terminus of an incoming Ub. The last Ub in the chain has its Lys48 solvent exposed and available to the next incoming Ub. The illustration shows unwanted K48-linked polyubiquitination resulting from compound binding and the ensuing interference with Ub binding in the pocket within the Tsg101 UEV domain.

The antiviral activity is based on the novel understanding that compounds having the property specified within this disclosure disrupt or inhibit formation of the TSG101 complex with Ub, thereby promoting the undesirable polyUb events that signal viral protein internalization. See FIG. 2.

The effect of the viral protein internalization is inhibition of viral particle release from the cell (see FIG. 3, top and middle panels) and reduction of virus infectivity (see FIG. 3, bottom panel).

Figure 4:
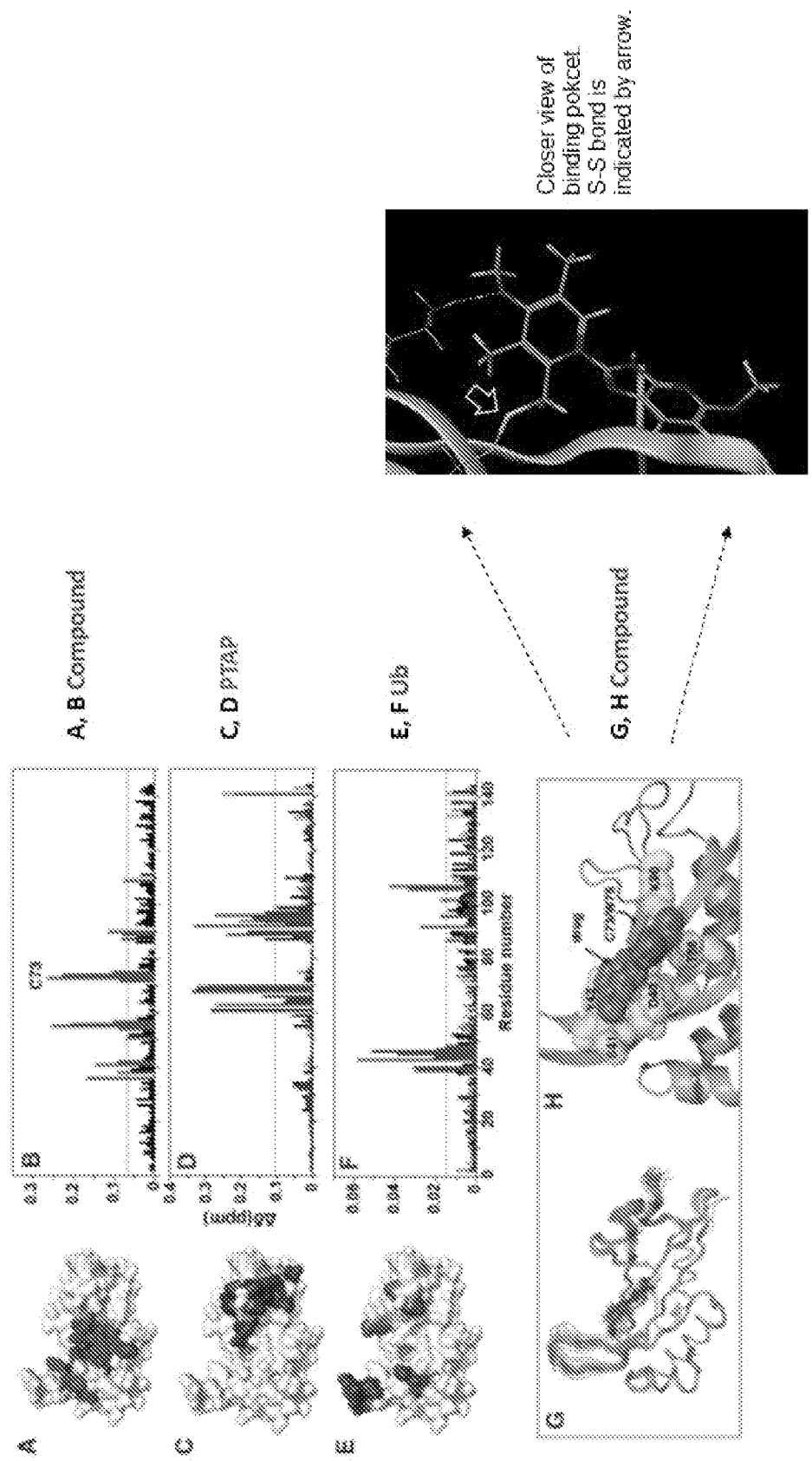
FIG. 4A-E. Binding of compound to Tsg101 UEV domain. Panels A, C, and E provide an illustration of regions significantly perturbed (darkened regions) in the Tsg101 UEV domain surface (white; from PDB ID: IKPP; Pornillos et al. EMBO J, 2002) following binding of compound (perturbed regions in red), PT AP (perturbed regions shown as darker region) and Ub (perturbed regions shown as darker region). Panels B, D, F, Large (gray bars) and small (black bars) NMR chemical shifts by residues in the Tsg101 UEV domain induced by incubation with compound (red); PTAP (panel D); and Ub (panel F). Chemical shifts obtained when the UEV domain was first incubated with compound and then followed by PTAP or Ub are represented as unfilled bars. Panel G, 200 structures of the compound-Tsg101 UEV complex were calculated of which the twenty lowest in energy are shown in ribbon, with the compound in lines. Panel H, Enlarged depiction of the lowest energy complex structure showing UEV domain region, compound (darker region) and binding site residues shown as spheres and sticks. Inset: illustration of disulfide adduct formed by compound.
Figure 5A:
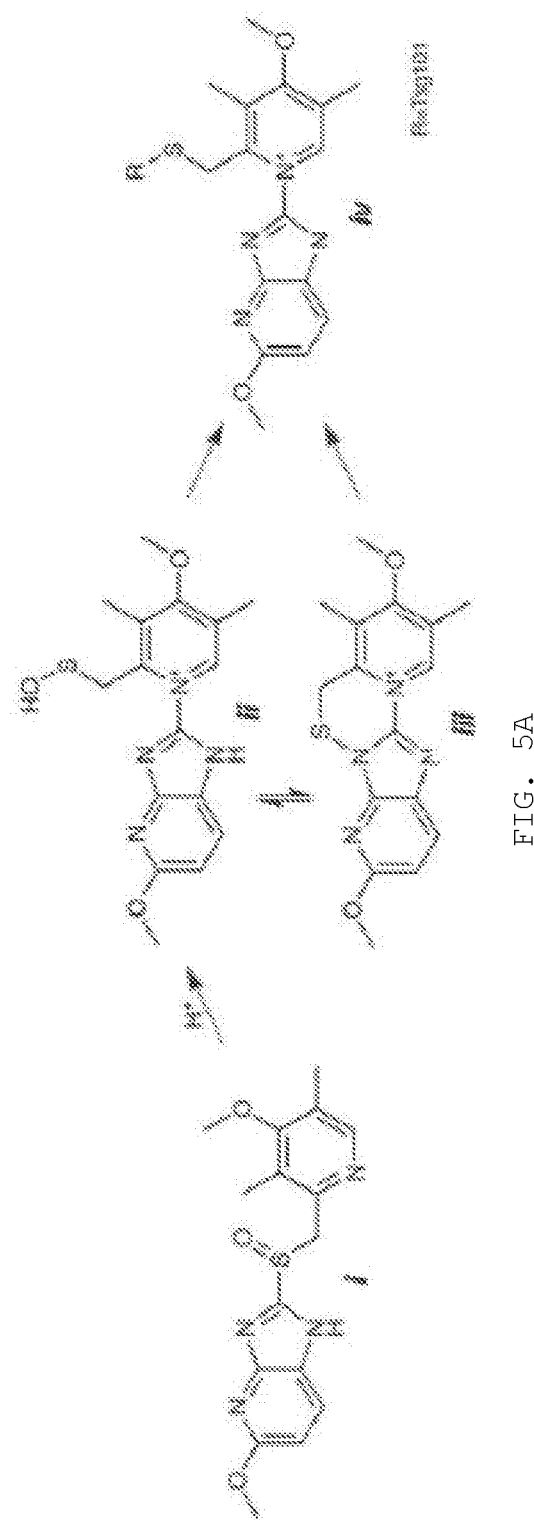
Figure 5B:
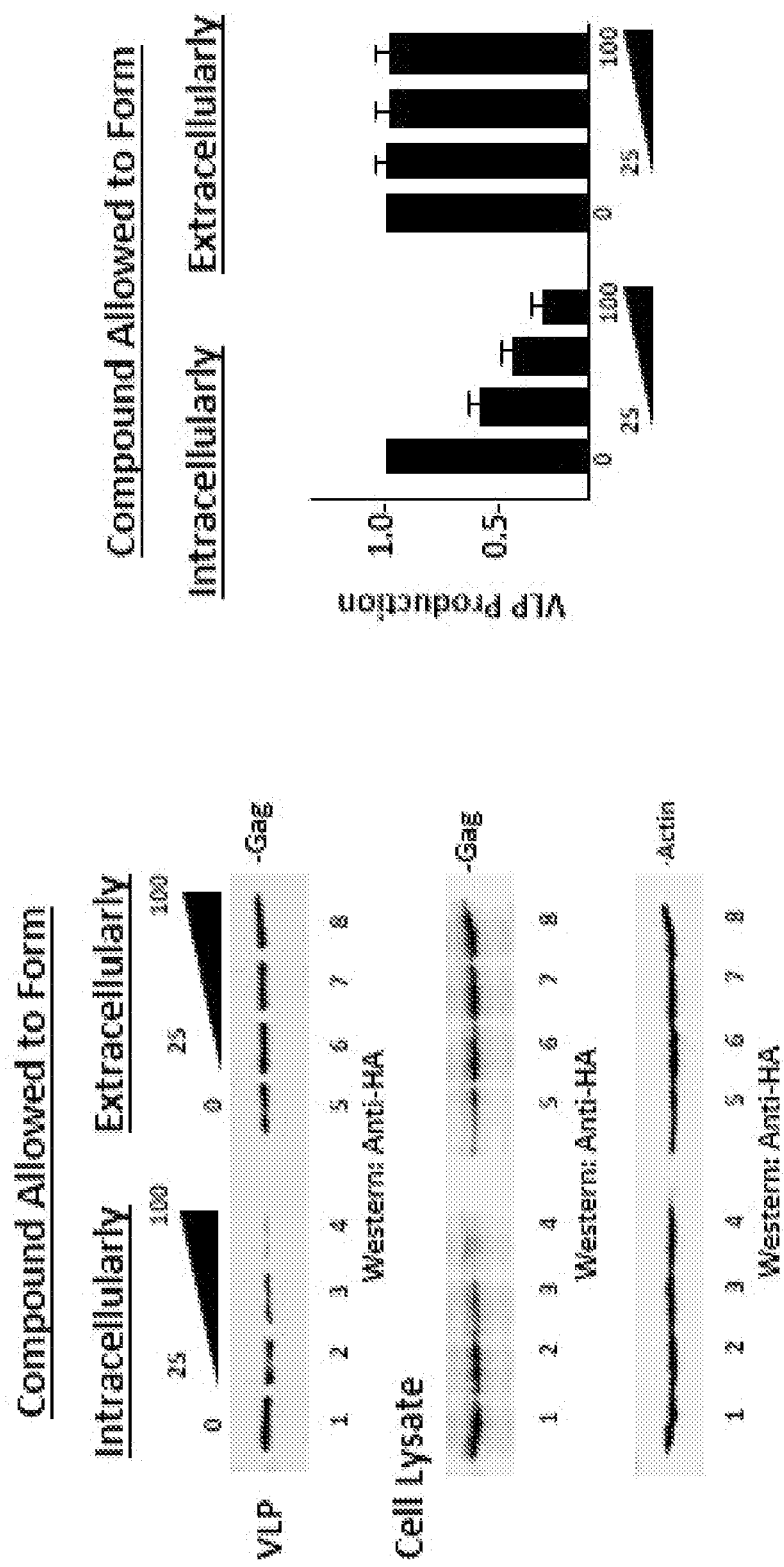
Figure 5C:
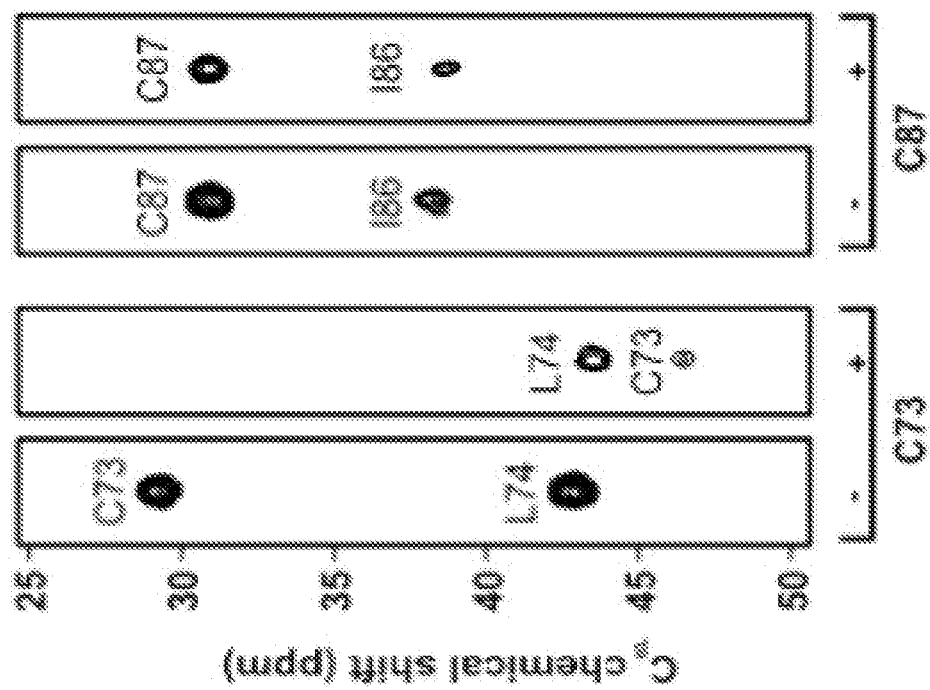

A key property conferring the compound with antiviral activity is the ability to form a reactive sulfide moiety within the cellular milieu at a site where the virus replicates that can attack specific Cys residues in TSG101, namely, Cys73 and/or Cys87 within the Ub-E2-variant (UEV) domain of the TSG101 protein (depending on the specific compound employed). See FIG. 4. W7S and F88 are also important contacts. FIG. 5A illustrates formation of the reactive sulfide moiety using a related compound. FIG. 5B illustrates that the antiviral activity requires intracellular formation of the reactive sulfide: inducing formation prior to cell uptake, ablates antiviral activity. FIG. 5C illustrates that the specific target residue within TSG101 for the compound illustrated in FIG. 5A is Cys73, as indicated by its perturbation when a compound capable of forming the reactive group is added; a nearby Cys residue is not disturbed. FIG. 5D illustrates that the Cys73 residue in TSG101 is also the specific target of the compound inside the cell as indicated by failure to prevent co-localization of Gag (green signal) and TSG101 (red signal) when Ala is substituted for Cys73 but not when Ala is substituted for Cys87.

Figure 6A:
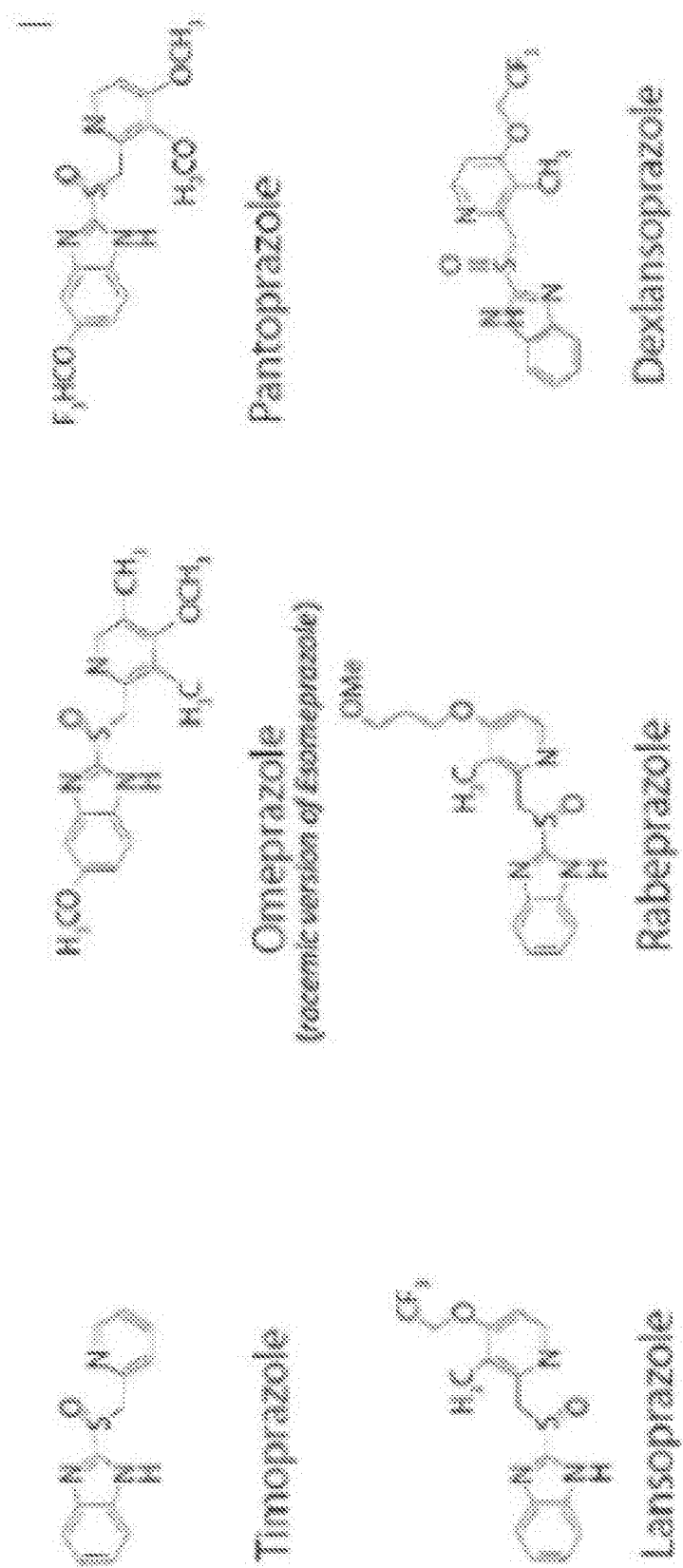
FIG. 6A-B. Proposed rabeprazole derivatives.

Compounds exemplifying the properties described herein are Rabeprazole (FIG. 6A) and related compounds (FIG. 6A, except tenatoprazole and esomeprazole).

Figure 7:
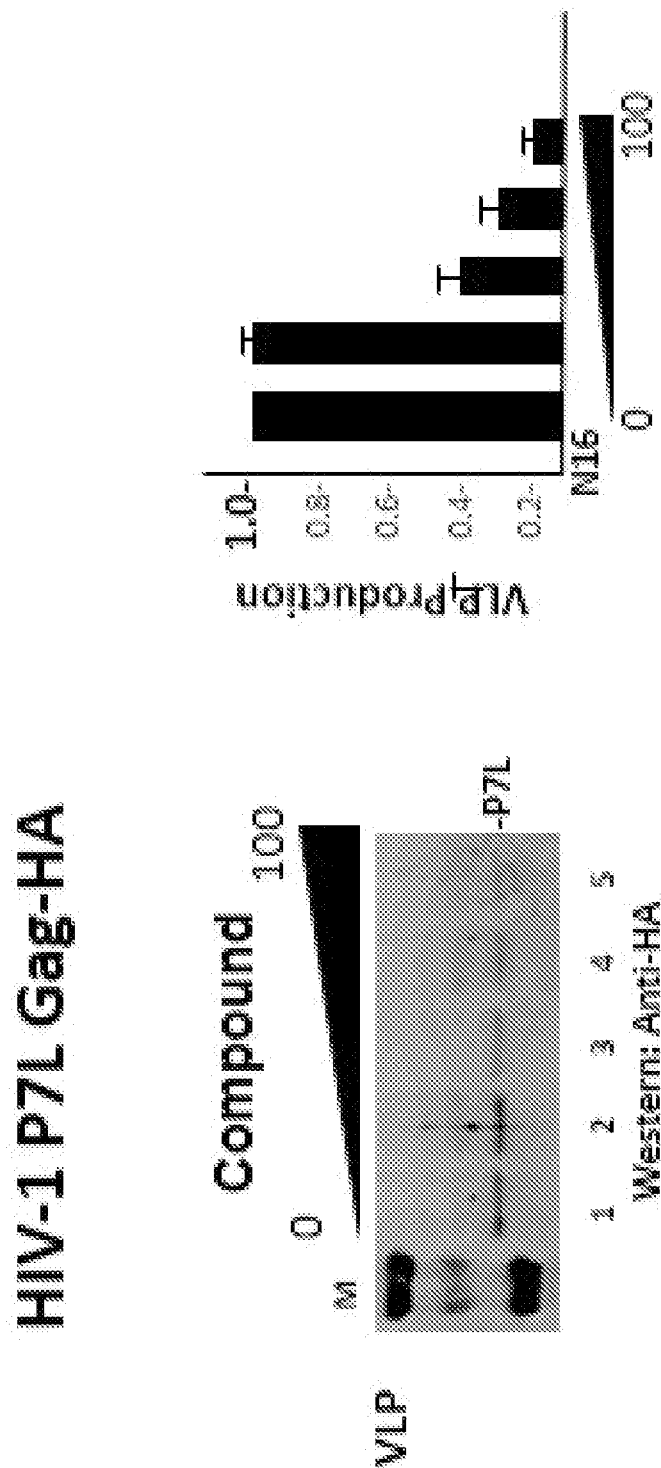
FIG. 7. Inhibitory effect of compound on Alix-driven budding of an HIV-1 Gag mutant. Western analysis of VLP production by cells expressing an HIV-1 Gag mutant (GagP7L) with a PTAP to LTAP mutation. P7L-Gag budding is directed by Alix which binds to the LYXP motif located several residues downstream of the PTAP motif. Bar graph, quantitation of VLP production normalized to that of mock-treated control.

The L domain motif (Pro-Thr-Ala-Pro or PTAP) in the HIV-1 Gag protein can bind a PTAP-binding pocket in the UEV domain of TSG101. The antiviral property described herein affects some residues involved in L domain recognition but does not require or target the intact L domain motif in the Gag protein for the interaction with TSG101. [e.g., Kim et al (2011) Elucidation of New Binding Interactions with the Human TSG101 Protein Using Modified HIV-1 Gag-p6 Derived Peptide Ligands ACS Med. Chem. Lett. 2, 337-341 targets the motif itself]. The evidence supporting this distinction is that a viral-encoded protein that lacks the intact L domain motif (designated as P7L Gag) can nevertheless be expected to be subject to ubiquitination (Gottwein et al. (2005)) and the replication of viruses bearing this mutation are, in fact, inhibited by compounds with the antiviral property specified in this Disclosure. See FIG. 7.

Figure 8:
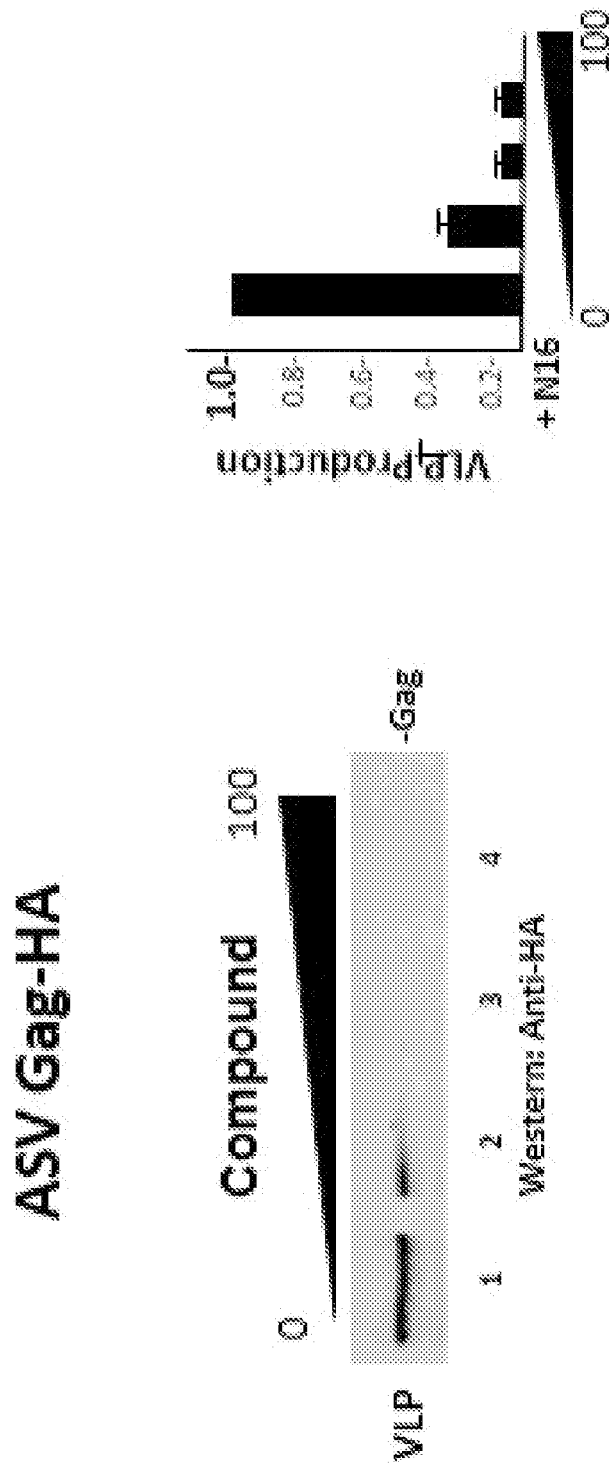
FIG. 8. Inhibitory effect of compound on Nedd4-driven budding of Avian Sarcoma Virus. Western analysis of VLP production by cells expressing the Avian Sarcoma Virus (ASV) Gag which does not have a PTAP motif but instead has a PY motif that is required for its budding. The PY motif recruits the E3 ligase, Nedd4. Bar graph, quantitation of VLP production normalized to that of mock-treated control.
Figure 9:
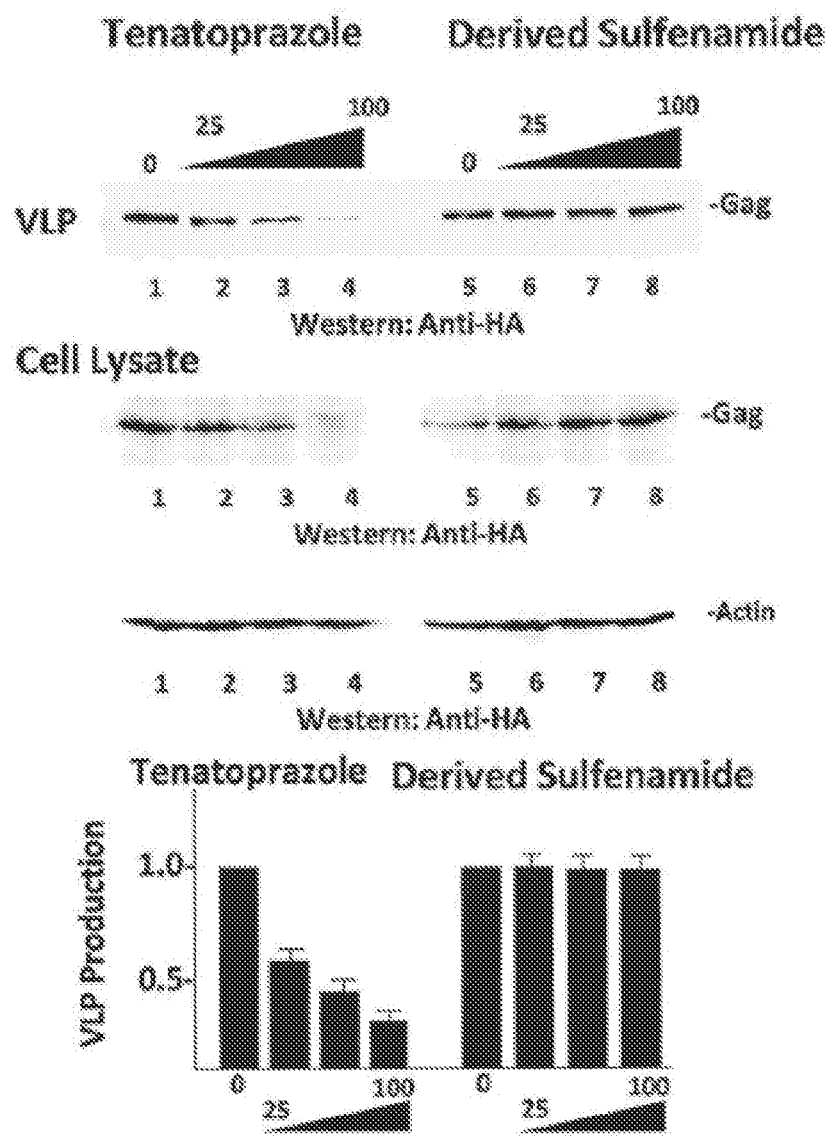
FIG. 9. See FIG. 5B above.
Figure 10A:
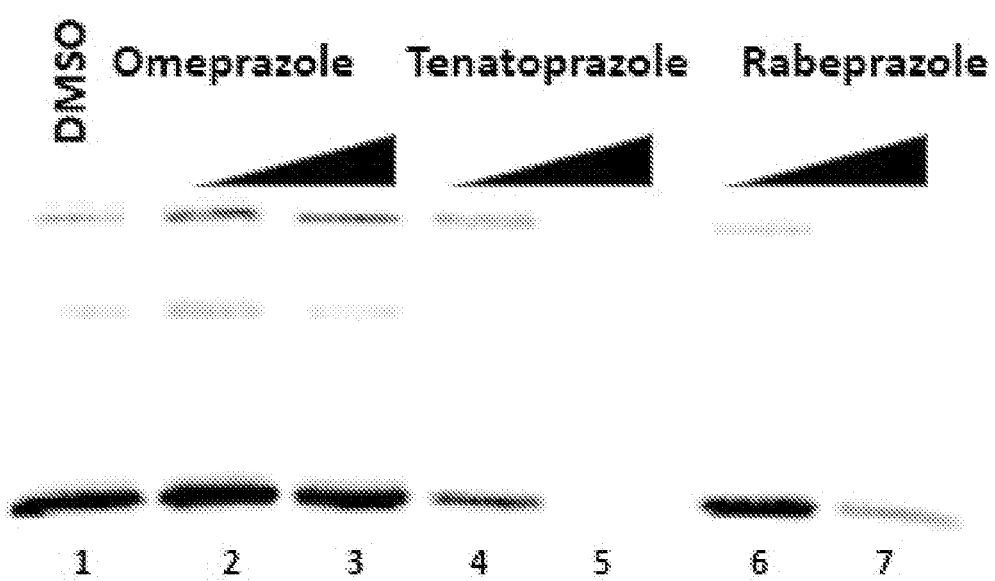
FIG. 10A-10C.
Figure 10B:
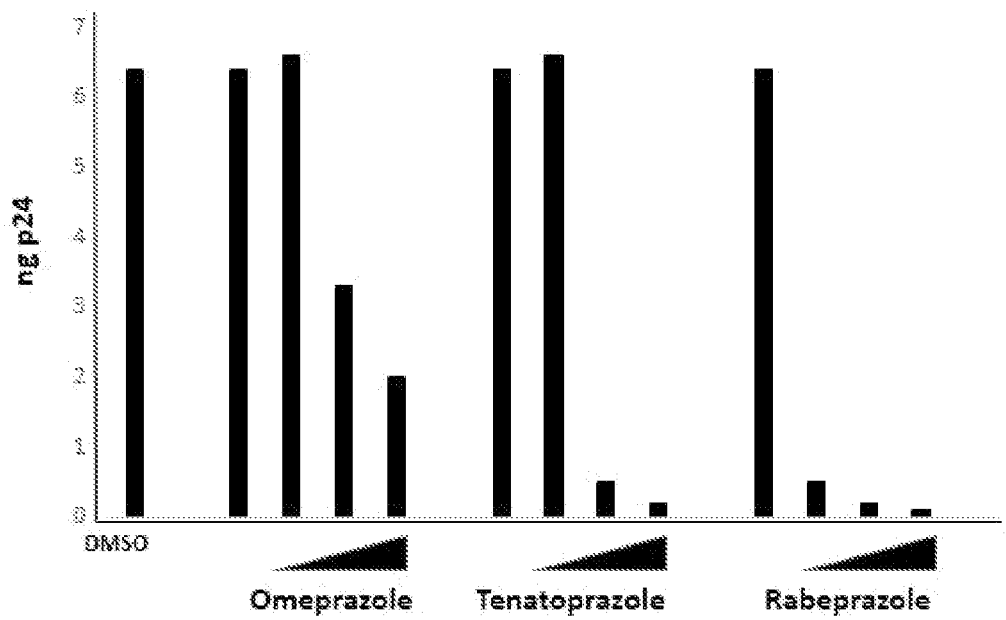
Figure 10C:
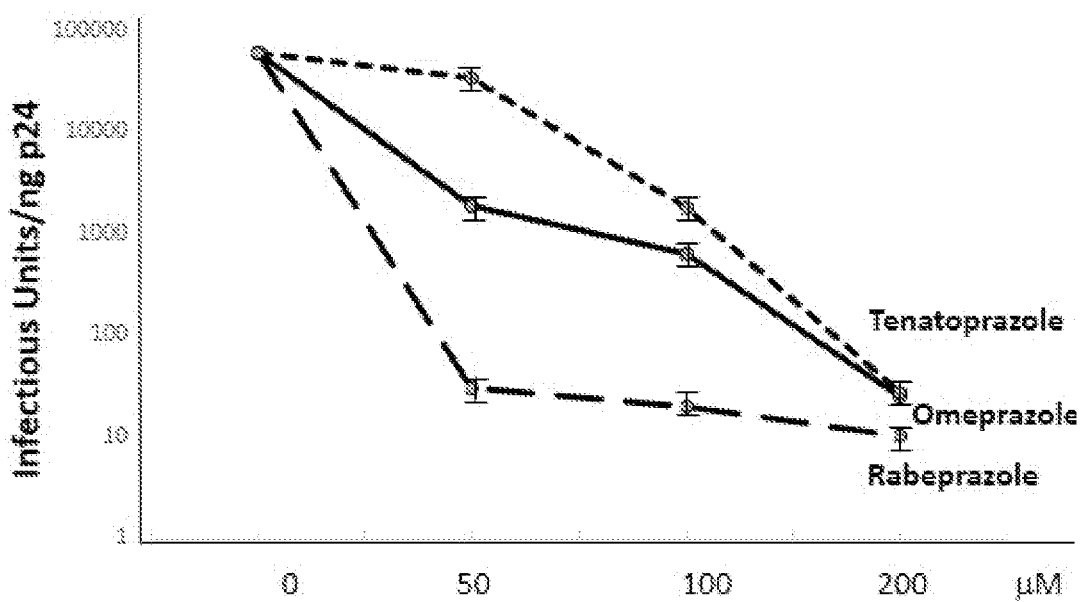
Figure 11A:
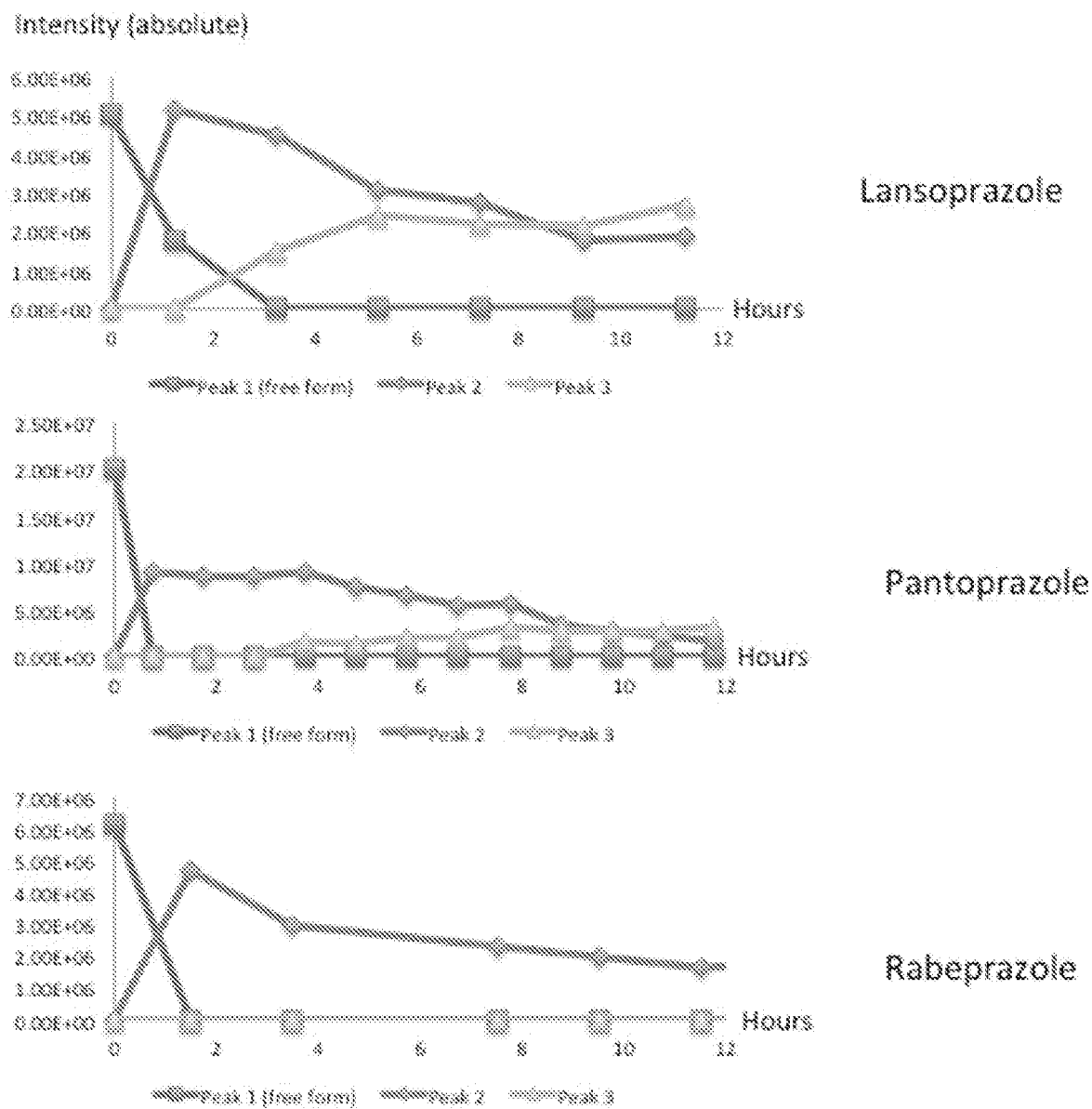
FIG. 11A. Comparison to time to formation of active sulfenamide compound.
Figure 11B:
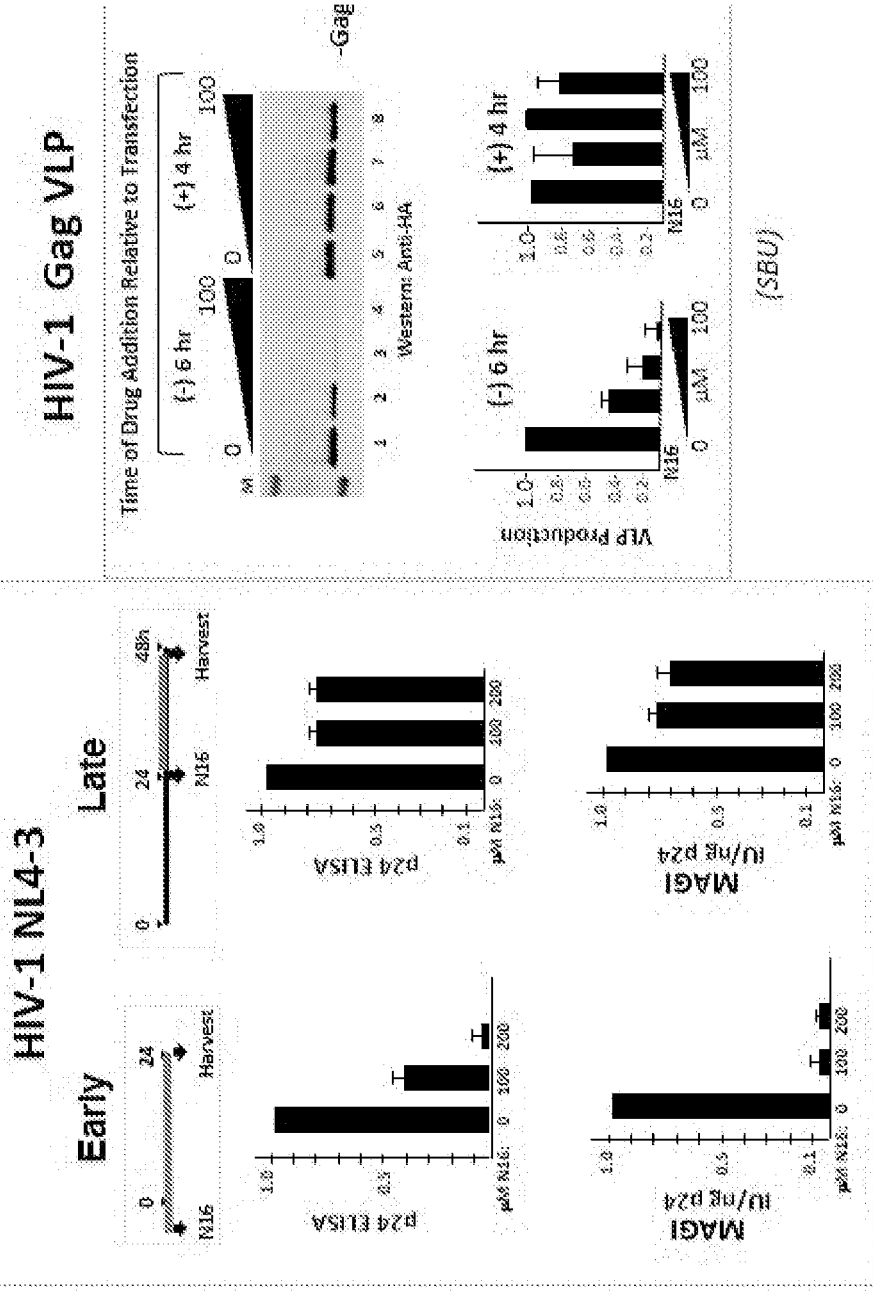
FIG. 11B. Time-dependence of anti-viral impact.
Figure 12:
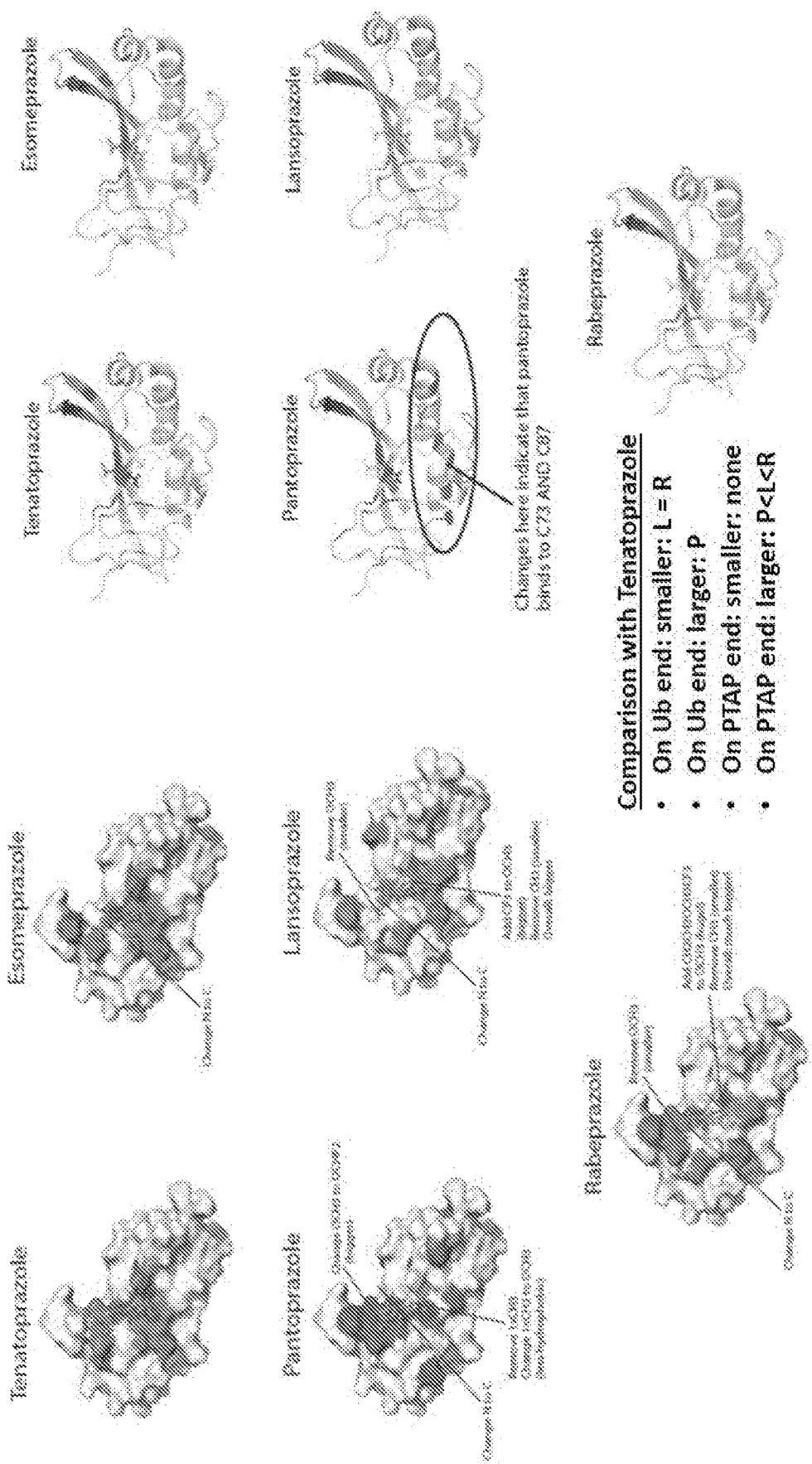
FIG. 12. Comparison of prazoles "fit" within Tsg101-UEV structure, relative to positions of Ub- and PTAP-binding pockets.

The antiviral properties of the compositions disclosed herein extends the anticipated range of pathogens that can be targeted beyond those that just rely on TSG101 for budding to those that also require Ub, which is a significantly broader group. Thus, the enveloped viruses to which the herein specified antiviral activity may apply can be Zika virus, Dengue virus, Human Immunodeficiency virus, Ebola virus, certain Hepatitis viruses, Herpes Simplex virus-1 and/or -2, Epstein-Barr virus, Mumps, Measles, Influenza virus, Vesicular Stomatitis virus, and viruses related to the above named groups. The evidence supporting this claim is that compounds with the antiviral property inhibit the production of the avian retrovirus (ASLV) which does not bind the TSG101 protein [Medina et al, (2008) TSG101 can replace Nedd4 function in ASV Gag release but not membrane targeting. Virol. 377:30-8.]. See FIG. 8.

Figure 6B:
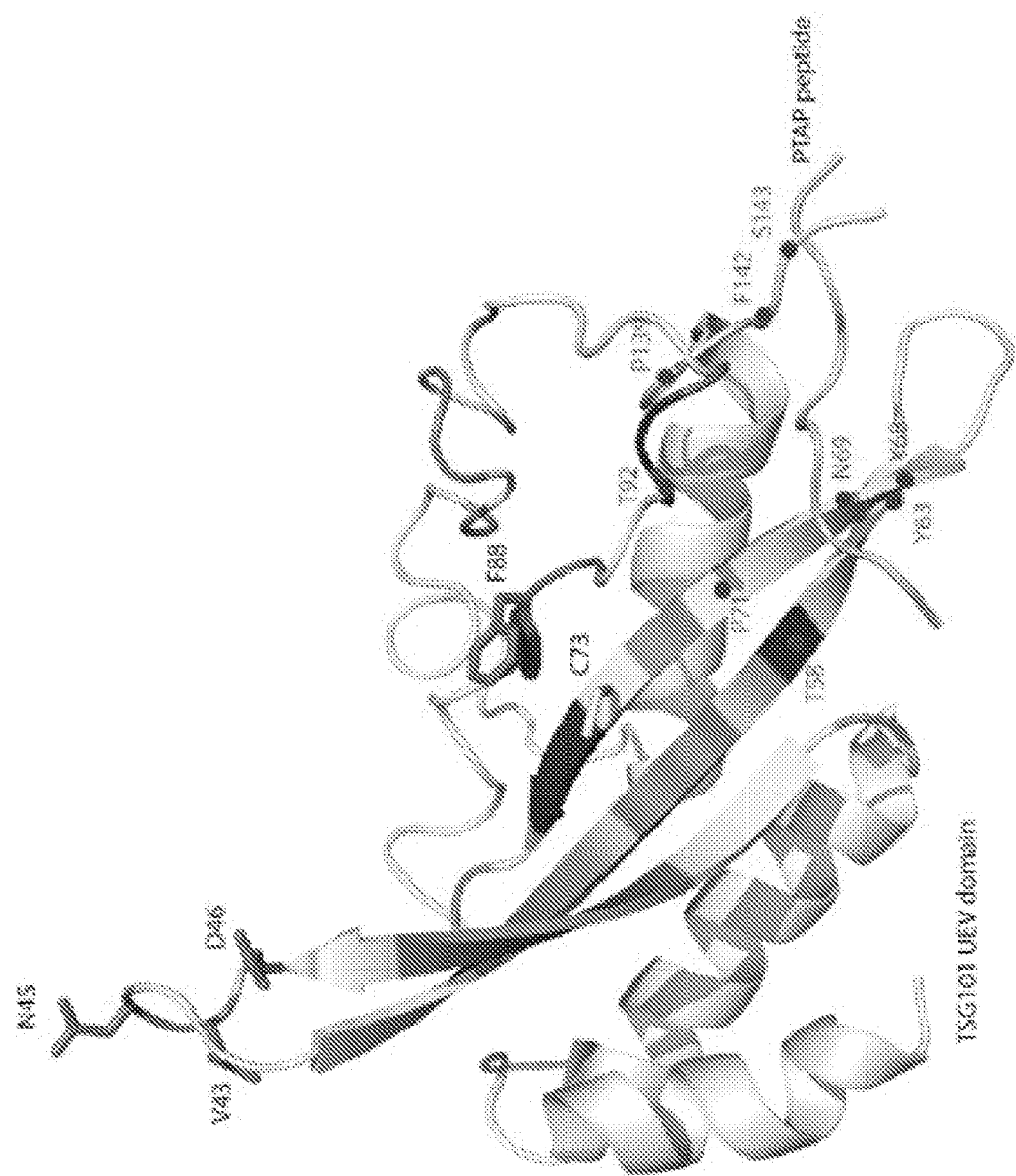

FIG. 6B shows the L domain motif contacts relative to the location of TSG101-Cys 73 that is target of compounds in panel 6A. The UEV domain of TSG101 in complex with the PEPTAPPEE peptide from the late domain of HIV-1 p6 (Gag) is derived from PDB structure 1M4P (Pornillos et al (2002) Nat Struct Biol 9, 812-817). Residues important for ubiquitin complexation are shown in sticks (D43, N45, D46 and F88) (PDB ID: ISlQ, Sundquist et al (2004) Molec Cell 13, 783-789). Residues which were found to undergo NMR chemical shift perturbations upon addition of the compound tenatoprazole are highlighted in light gray (moderate changes, >1 SD above zero) and dark gray (large changes, >2 SD above zero). Tenatoprazole was found to bind covalently to cysteine 73, as confirmed by mass spectroscopy and NMR. Chemical shifts measured by NMR are an indication of local environment. Changes in chemical shifts upon addition of a ligand can indicate the location of ligand binding. In the UEV domain of TSG101, these chemical shift changes occurred around cysteine 73, with larger changes closer to this residue indicating that this was indeed the site of ligand binding.

The evidence for covalent binding to cysteine 73 is that mass spectrometry of the UEV domain of TSG101 in the presence and absence of tenatoprazole indicated two things: (1), that Tenatoprazole binds to TSG101 in a covalent manner; and (2), that there is a 1:1 binding ratio of tenatoprazole to TSG101. It is noted that NMR spectroscopy is capable of revealing sites of covalent attachment by comparison of the spectra before and after addition of the ligand. After addition of tenatoprazole to the UEV domain of TSG101, cysteine 73 showed a large change in the C_beta chemical shift characteristic of covalent disulfide bond formation, whereas the C_beta of cysteine 87 did not. Putting the data together, tenatoprazole binds covalently via a disulfide bond to cysteine 73 of the UEV domain of TSG101.

The tenatoprazole binding site therefore overlaps with both the PTAP binding site and that of Ub. See FIG. 4. Perturbations line up with the Pro 7 and Pro 10 contacts but the Thr 8 or Ala 9 contacts were not disturbed. Threonine 58 is the key. It has a large chemical shift change when N16 binds. In addition, it definitely makes multiple contacts with the PTAP peptide. It binds two proline residues in particular in the PEPTAPPEE peptide: the first and third prolines, i.e., (P)E(P)TAPPEE. Rationale: For enhancement of binding affinity, attach the compound to a peptide via one of the aromatic rings of the compound. That way the binding of the compound to TSG101 should not be affected (since the different proton pump inhibitors are all altered on one or both of these rings, indicating that changing the substituents on the rings doesn't change the binding too much. These rings could be attached to the N-terminus of the peptide, or via a linker, or synthetic unnatural amino acid.

Omeprazole: The binding mode is the same as in ATPase (via sulfonamide intermediate).

The sulfenamide is made more quickly in acidic conditions and with heat. It is very reactive and can go on to form a dimer. Isolation of the dimer and testing indicates that it doesn't bind to TSG101.

The sulfenamide has no antiviral activity in tissue culture (FIG. 5B) most likely its charge prevents it from passing through cell membrane).

Esomeprazole is more soluble than tenatoprazole. They exhibited comparable binding in the in vitro binding assay but Esomeprazole is less effective than Tenatoprazole in the tissue culture budding assay (FIGS. 9A-9C).

Pantoprazole, Lansoprazole/Dexlansoprazole (dexlansoprazole is the active enantiomer of the racemic lansoprazole), and Rabeprazole were in the NWU screen but were not considered hits.

Lansoprazole bound weakly in the NWU screening assay; Rabeprazole bound as well as tenatoprazole; uncertain why it was not considered a hit.

Esomeprazole is unstable in water: a red compound (presumably the rearranged dimer) is formed after only one hour at room temperature in water.

Esomeprazole is insoluble in water, DMSO is fine. It is also more stable in DMSO, as long as it is not exposed to air/moisture/heat.

Esomeprazole reacts slowly (presumably because a covalent bond is forming and the molecule must rearrange before binding). It seems to bind faster at higher temperature and lower pH. Reactions have been done at pH 5.8 as the recombinant TSG101 protein seems to be unstable at any pH above 7.5. In cytosolic conditions, pH is likely to be around 7.4, which might change the reactivity.

Esomeprazole must rearrange to bind TSG101. The intermediate is short-lived and charged, possibly preventing it from crossing membranes. It should be noted that the number of moles of pro-drug is not the same as the number of moles that rearrange and bind to TSG101. Antiviral property might require higher prodrug concentration.

Rabeprazole is the fastest binder; it converts to the sulfenamide faster than Omcprazole, Lansoprazole, and Pantoprazole versus Pantoprazole, which takes ~9 hr to form sulfenamide (Primi et al 1999;). Lanzoprazole is ~2× as slow as Rabeprazole. Pantoprazole also perturbs residues AWAY from PTAP versus Tenatoprazole [In Primi et al, when half-lives of lansoprazole and rabeprazole were compared at pH 5.1, the lansoprazole half-life was 1.5 h while that of rabeprazole was 0.12 h]

To measure sulfenamide formation: Dissolve each compound in water/buffer and measure the formation of colored compounds by UV-visible absorption, since the initial compound is colorless and the final compound (the sulfenamide dimer) is colored. Interestingly, they are all different colors. F15 and N16 are red, pantoprazole is yellow, rabeprazole is green and lansoprazole is purple.

For the on-rate (i.e, time to binding; since a disulfide bond is formed, the off-rate is very slow), Panto- and Lanzo show two peaks: the first appears at the beginning of the experiment, usually within an hour or two, the second after ~3-4 hours (which seems to increase while the first drops). The compound may first bind to one cysteine (C73) and then to another (C87) or the binding may be biphasic. Tenato-, Rabe- and Esomeprazole show no evidence of two binding sites in the NMR.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon or nitrogen-nitrogen double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^2H$ and/or wherein the isotopic atom $^{13}C$. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

Variations on those general synthetic methods will be readily apparent to those of ordinary skill in the art and are deemed to be within the scope of the present invention.

The articles "a", "an" and "the" are non-limiting. For example, "the method" includes the broadest definition of the meaning of the phrase, which can be more than one method.

As used herein, "about" in the context of a numerical value or range means ±10% of the numerical value or range recited or claimed.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times weekly and so on, etc.

As used herein, to "treat" or "treating" encompasses, e.g., inducing inhibition, regression, or stasis of the disorder and/or disease. As used herein, "inhibition" of disease progression or disease complication in a subject means preventing or reducing the disease progression and/or disease complication in the subject.

For the foregoing embodiments, each embodiment disclosed herein is contemplated as being applicable to each of the other disclosed embodiments.

All combinations, sub-combinations, and permutations of the various elements of the methods described herein are envisaged and are within the scope of the invention.

By any range disclosed herein, it is meant that all hundredth, tenth and integer unit amounts within the range are specifically disclosed as part of the invention. Thus, for example, 10 mg to 60 mg means that 10.01, 10.02 . . . 10.09; 10.1, 10.2 . . . 10.9; and 11, 12 . . . 59 mg unit amounts are included as embodiments of this invention. By any range of time disclosed herein (i.e. weeks, months, or years), it is meant that all lengths of time of days and/or weeks within the range are specifically disclosed as part of the invention. Thus, for example, 3-6 months means that 3 months and 1 day, 3 months and 1 week, and 4 months are included as embodiments of the invention.

Another aspect of the invention comprises a compound used in the method of the present invention as a pharmaceutical composition. In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

This invention will be better understood by reference to the Examples which follow, but those skilled in the art will readily appreciate that the specific experiments are only illustrative of the invention as described more fully in the claims which follow thereafter. Every embodiment and feature described in the application should be understood to be interchangeable and combinable with every embodiment contained within

EXPERIMENTAL DETAILS

Example 1

An experiment was conducted to show that disruption of UEV Ub binding by commonly used drugs arrested assembly at an early step distinct from the late stage involving PTAP binding disruption. NMR revealed that the disruption by the drugs is due to the formation of a covalent adduct near the Ub-binding pocket.

The human immunodeficiency virus type-1 (HIV-1) is dependent on the cellular protein, Tsg101, for budding. The recruitment and delivery of Tsg101 to viral assembly sites is accomplished through its interaction with the virally-encoded structural precursor polyprotein, Gag, which directs viral particle release and has a Pro-Thr-Ala-Pro (PTAP) motif in its C-terminal p6 region that serves as docking site for Tsg101 (Garrus, J. E. et al. (2001); Martin-Serrano, J., et al. (2001); VerPlank, L. et al. (2001)). The critical dependence on Tsg101 for productive viral replication is reflected in the fact that, despite motif duplication and extensive genetic heterogeneity in the HIV genome sequence, HIV variants with mutations within the PTAP motif have not been identified to date (Martins, A. N. et al. (2016)). The Tsg101 protein is a component of ESCRT-I, one of four complexes (ESCRT-0, -I, -II, -III) that comprise the highly conserved ESCRT (endosomal sorting complex required for transport) machinery. As such, Tsg101 participates in the role of ESCRT in endosomal sorting and trafficking of ubiquitinated cargo to degradative compartments in the cell interior (Hurley, J. H. (2008); Raiborg, C. & Stenmark, H. (2009)). Gag and the recruited Tsg101 most likely meet in the cytosol and the complex brought to sites of assembly on the plasma membrane by virtue of membrane-binding determinants in the matrix domain of Gag (Ehrlich, L. S. & Carter, C. A. (2012); Dordor, A., et al. (2011)).

Central to Tsg101 participation in Gag assembly is its ubiquitin E2 variant (UEV) domain. UEV proteins, and the UEV domain in Tsg101, lack the critical Cys residue essential for conjugation and transfer of Ub to protein substrates or Ub-ligating (E3) enzymes (Koonin, E. V. & Abagyan, R. A. (1997); Ponting, C. P., et al. (1997)). UEV proteins are highly conserved in evolution and constitute a family of proteins structurally related to, but distinct from, E2 enzymes. The Tsg101 UEV domain contains, in addition to an Ub-binding pocket, another pocket with affinity for PT/SAP motifs (Pornillos, O., *Nat Struct Biol* 9, 812-817, doi:10.1038/nsb856 (2002); Pornillos, O. et al. *EMBO J* 21, 2397-2406, doi:10.1093/emboj/21.10.2397 (2002); Teo, H., et al. (2004); Sundquist, W. I. et al. (2004)). The inventors hypothesized that Tsg101 uses its UEV domain to regulate protein levels of other proteins (VerPlank, L. et al. (2001)). The inventors earlier finding that HIV-1 Gag binds Tsg101 through the UEV domain suggested that Tsg101 was recruited as a chaperone to block non-productive Gag ubiquitination that might lead to its degradation, an idea supported by the fact that cyclin-specific E2 enzymes with Ser substituted for the active Cys are, in fact, dominant-negative inhibitors of cyclin destruction (Townsley, F. M., et al. (1997)). Mak, Cohen and collaborators demonstrated that, in concert with the E3 ligase MDM2, Tsg101 regulates protein levels of the transcription factor p53 (Li, L., et al. (2001); Ruland, J. et al. (2001)). This function was suggested to be independent of the PTAP-binding pocket. Despite indications that Ub plays a critical role in both budding and virus maturation (Patnaik, A., et al. (2000); Schubert, U. et al. (2000); Strack, B., et al. (2000); Martin-Serrano, J., et al. (2004); Sette, P., et al. (2013)), how the Tsg101 Ub binding pocket participates in the virus assembly pathway is presently not known.

The following study provides evidence that the UEV domain of Tsg101 provides chaperone function to HIV-1 Gag that is independent of its interaction with the PTAP motif, supporting the hypothesis that the domain provides a function in addition to its well-established role in ESCRT factor recruitment. Key tools in these studies are agents identified by high-throughput screening of a small molecule library for compounds capable of binding the Tsg101 UEV domain. The inhibitory effects of these probes on HIV-1 Gag assembly, which were found to be highly specific, suggest that the agents can serve as leads for identification of potent inhibitors of HIV and other pathogens that require Tsg101 participation in viral replication.

Figure 13A:
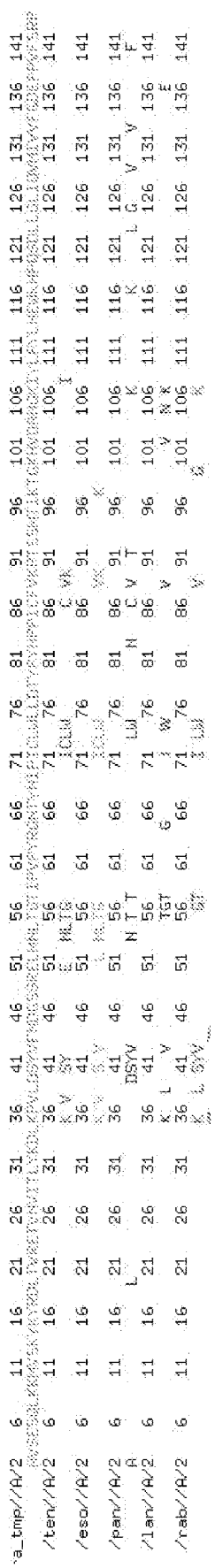
FIG. 13A. NMR and fluorescence perturbances indicate that all of the compounds (tenatoprazole, esomeprazole, pantoprazole, lansoprazole, and rabeprazole) bind to residue C73. Pantoprazole has additional binding at C87.
Figure 13B:
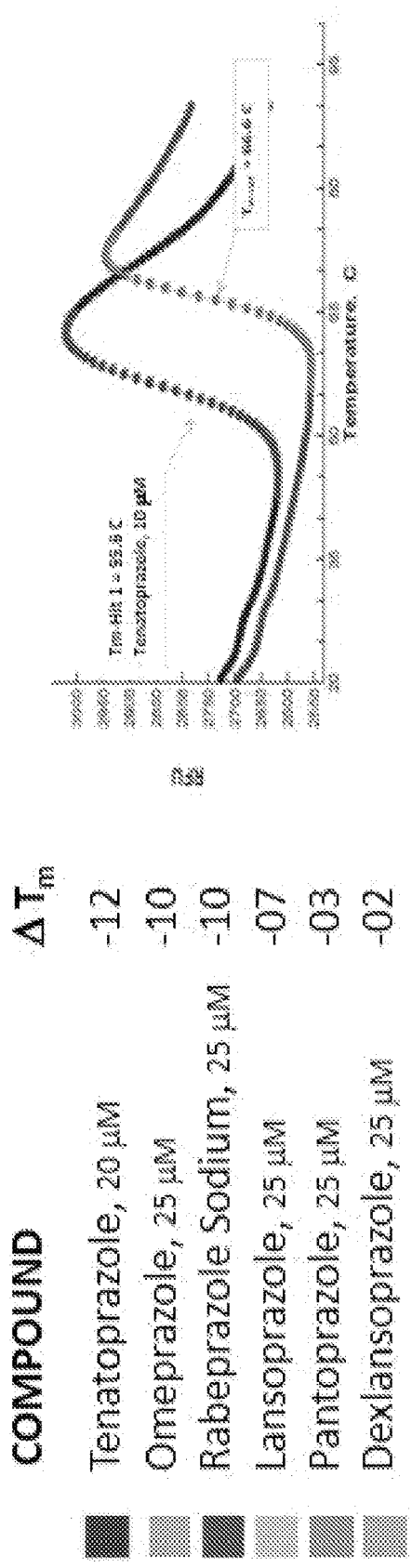
FIG. 13B. TSG101 binding of prazole compounds. Melting curves of TSG101 with various prazole compounds assayed by relative fluorescence (RFU) shift. Two control compounds, K21 and N20, had no effect at 40 μM on the Tsg101 melting curve.

F15 (esomeprazole) and N16 (tenatoprazole) are two related compounds identified in a screen of small molecules capable of binding to the UEV domain of Tsg101 (FIG. 13A-B). F15 (trade name Nexium) is widely used for indications of heartburn (also known as acid indigestion). The compounds share the same heteroaromatic core structure, differing in only one atom, and behaved very similarly in all experiments.

Materials & Methods
Plasmids and Reagents pNL4-3ΔEnv, pIIIB-Env3-1, pCMV-Gag-HA encoding HIV-1 Gag C-terminally tagged with hemagglutinin, as previously described in the art were used (Watanabe et al. (2013)). pCMV-Gag-EGFP encoding HIV-1 Gag C-terminally tagged with green fluorescent protein (GFP) and pLLEXP1-hTsg101-myc encoding full-length human Tsg101 C-terminally tagged with myc as previously described in the art were used (Goff, A., et al. (2003)). pLLEXP1-hTsg101-myc and pLLEXP1-hTSG101-FLAG (siRNA resistant) were used as templates for site-directed mutagenesis to generate single amino acid substitution mutants: C73A and C87A (Lu, Q., et al. (2003)). Primary antibodies were: Rb anti-CA; mouse anti-HA and anti-actin (Biolegend); mouse anti-myc (Santa Cruz Biotechnology). Secondary antibodies were: goat anti-mouse IgG Alexa Fluor 680 and Texas Red tagged anti-mouse IgG (Molecular Probes); goat anti-rabbit IRDye800 (Rockland). Chemicals: N-ethylmaleimide (NEM) and carbobenzoxyl-leucine-leucine-leucinal (MG132) (Sigma); bortezomib (Selleck Chemicals).

Transfection and Assays for Particle Budding and Infectivity

For production of virus particles, 293T cells were transfected with pNL4-3-ΔEnv and pIIIB Env3-1 plasmids and for virus-like particles (VLP), with pCMV-Gag-HA as previously described (Watanabe et al. (2013)). For specific infectivity, media-associated p24 was determined by ELISA (Immunodiagnostics, Inc.) and equivalent amounts of p24 were used to infect HeLa-CD4+-LTR-3 gal cells for infectivity measurement by the multinuclear activation of a galactosidase indicator (MAGI) assay. For VLP isolation and analysis, media was filtered (0.45 micron), pelleted through a 20% sucrose cushion and examined by Western blotting. For cell-associated Gag analysis, cell pellets were lysed with either Triton X-100 or RIPA buffer with complete mini protease inhibitor cocktail (Roche) and analyzed by Western blotting. Protein bands were visualized using an infrared-based imaging system (Odyssey, LI-COR Biotechnology) and band intensities measured using the Li-Cor Odyssey software version 2.1.15. Virus particle release efficiency was calculated [VLP signal intensity/(VLP signal intensity+cell lysate signal intensity)]. Quantification analyses plot the data mean with error bars signifying plus or minus 1 standard deviation (SD).

IC50 Calculation

Cells were grown in 96-well trays for 24 hr with increasing levels of drug, metabolic activity was measured using WST-1colorimetric assay (Roche), and IC50 values were calculated (Prism 6, Graph Pad Software Inc.).

Fluorescence Microscopy

Hela cells grown on cover slips were transfected with pCMV-Gag-EGFP alone or together with pLLEXP1-hTsg101-myc. Cells were fixed in 4% formaldehyde (Sigma) and permeabilized in 0.1% Triton X-100. Tsg101 was detected in the samples by indirect immunofluorescence using anti-myc Mab and Texas Red anti-mouse IgG. Nuclei were stained with Hoechst. Images were captured on an inverted fluorescence/differential-interference contrast (dic) Zeiss Axiovert 200M deconvolving fluorescence microscope operated by AxioVision Version 4.5 (Zeiss) software and deconvolved by using the constrained iterative method (AxioVision). Protein co-localization was assessed in 40 or more cells by determination of Pearson's coefficient of correlation using Image J software and regarded as significant when a value of 0.6 or higher (equivalent to a 95% level of confidence for that number of cells) was observed (Manders, E. M. M., et al. (1993)).

Electron Microscopy 293T cells grown on ACLAR film that have been transfected and treated as described were fixed in 2.5% EM grade glutaraldehyde in PBS, soaked in 2% osmium tetroxide, dehydrated in a graded series of ethyl alcohol solutions and embedded in Durpan resin. Thin sections of 80 nm were counterstained with uranyl acetate and lead citrate and viewed with a FEI Tecanal BioTwinG2 electron microscope.

Production of Recombinant Tsg101 UEV Domain

N-terminally Hiss-tagged Tsg101 UEV domain (residues 2-145) was encoded in a pET-28b vector (Novagen—EMD Millipore), which included a TEV protease cleavage site ($His_6$-TEV-Tsg101$^{2-145}$). Tsg101 protein was expressed in Rosetta 2 (DE3) pLysS *E. coli* competent cells (EMD Millipore) grown in M9 medium containing 50 mgL$^{-1}$ kanamycin (Sigma) and 34 mgL$^{-1}$ chloramphenicol (Sigma), supplemented with $^{15}NH_4Cl$ and either natural abundance glucose or [U-$^{13}$C]-glucose to obtain 15N-Tsg101 UEV and $^{15}N/^{13}C$-Tsg101 UEV, respectively. The proteins were purified to homogeneity using immobilized nickel ion affinity chromatography (HisTrap FF, GE Healthcare) before and after TEV protease cleavage to remove the N-terminal His$_6$ tag, followed by size-exclusion chromatography (HiLoad 16/60 Superdex 75 pg, GE Healthcare) for final purification. Cleavage by TEV protease resulted in a non-native glycine at the N-terminus (residue 1). NMR samples contained ~0.6 mM Tsg101 UEV, 20 mM potassium phosphate (pH 5.8), 50 mM NaCl, and 8% $^2$H2O. For the $^{13}$C-aromatic, $^{13}$C-aliphatic, and $^{13}$C-filtered NOESY experiments, the sample was exchanged into the same buffer dissolved in 99.96% D20 (Cambridge Isotope Laboratories).

Preparation of Tsg101 UEV-N16 Complex

N16 (20 mM solution, DMSO) was added to Tsg101 UEV domain in a 10:1 ratio (N16 excess). Complete formation of the N16 UEV complex was observed at 2 hours by following chemical shift perturbations, which coincided with a red coloring of the solution. Since the complex was covalent, excess unbound N16 and DMSO could be removed by Amicon Ultra centrifugal filtration (MWCO 10 kDa, Millipore).

Liquid Chromatography-Mass Spectrometry (LC-MS)

The intact mass and purity of the protein samples were confirmed by LC-MS (Agilent 6224 ESI-TOF LC-MS). LC-MS confirmed 99% $^{15}$N-labeling (16727.8 Da for $^{15}$N-Tsg101 UEV vs expected 16729.2 Da for 100% $^{15}$N-labeling) and 98% $^{13}$C-labeling (17471.5 Da for $^{15}$N/$^{13}$C-Tsg101 UEV assuming 99% $^{15}$N-labeling vs expected 17488.2 Da for 100% $^{15}$N- and $^{13}$C-labeling). Covalent attachment of N16 was also confirmed by LC-MS (17057.2 Da for N16 $^{15}$N-Tsg101 UEV vs expected 17057.2 Da, assuming loss of oxygen associated with rearrangement).

NMR Spectroscopy (Binding Studies)

For binding studies using NMR spectroscopy, the following complexes were made: Tsg101 UEV-N16, UEV-PTAP, UEV-Ub, UEV-N16-PTAP, and UEV-N16-Ub, all in Tsg101 NMR buffer: 20 mM potassium phosphate, 50 mM NaCl, pH 5.8, with UEV concentration of 200 µM. PTAP (Ace-NFLQSRPEPTAPPEE-CONH2, Bio-Synthesis, Texas), is a synthetic peptide based on residues 15-16 of the HIV-1 Gag$^{WT}$ spacer peptide 2 ($^{15}$NF$^{16}$) and 1-13 of the HIV-1 Gag$^{WT}$ p6 sequence ($^1$LQSRPEPTAPPEE$^{13}$), which was dissolved in Tsg101 NMR buffer at a concentration of 1 mM before addition to Tsg101 UEV or UEV-N16 at a final 1:1 ratio. Ub (wild-type, unlabeled ubiquitin, 936 µM) was purified as previously described and was dialyzed against Tsg101 NMR buffer along with UEV or UEV-N16 prior to mixing at a final 1:1 ratio (Lazar, G. A., et al. (1997)).

Chemical Shift Perturbations

The assignment of Ub in complex with Tsg101 UEV and UEV-N16 was carried out using chemical shift titrations, by measuring HSQC spectra at a 1:0, 1:0.5, and 1:1 ratio of UEV or UEV-N16 to Ub. The assignment of the UEV-PTAP complex was carried out using a $^{15}$N-edited NOESY spectrum and by comparison with the BMRB chemical shifts previously deposited for the structure of Tsg101 UEV in complex with a PTAP peptide (BMRB: 5532, PDB: 1M4Q, 1M4P) (Pornillos, O., et al. Nat Struct Biol 9:812-817, doi:10.1038/nsb856 (2002)). The assignment of the UEV-N16-PTAP complex was assigned by direct comparison with the UEV-N16 and UEV-PTAP chemical shifts, for residues in the N16 and PTAP binding sites, respectively. All chemical shift perturbations were calculated according to the following equation: $\sqrt{[(H_{complex}-H_{free})^2+(\alpha(N_{complex}-N_{free}))^2]}$, where α is a scaling factor equal to 0.13, calculated from $\alpha=(H_{max}-H_{min})/(N_{max}-N_{min})$, where $H_{complex}$ and $N_{complex}$ describe the H and N chemical shifts in the complexed form, $H_{free}$ and $N_{free}$ describe the H and N chemical shifts in the free form, $H_{max}$ and $N_{max}$ describe the largest chemical shifts from the $^1$H/$^{15}$N-HSQC spectrum of Tsg101 in the free form, and $H_{min}$ and $N_{min}$ describe the smallest chemical shifts (Williamson, M. P. (2013)). Additionally, chemical shift perturbations involving two ligands, e.g. Tsg101-N16 with PTAP or Ub, were calculated in an analogous manner. The cutoff for large chemical shift perturbations was 1.5 standard deviations from zero.

NMR Spectroscopy

NMR data were acquired at 300 K on Bruker 600, 800, and 900 MHz spectrometers, each equipped with a cryogenic probe, using $^{13}$C/$^{15}$N-Tsg101 in complex with natural abundance N16. Spectra were processed using NMRPipe and analyzed using CCPN Analysis 2.4.1 (Delaglio, F. et al. (1995); Vranken, W. F. et al. (2005)). Assignments were completed using standard triple-resonance techniques, with data obtained from the following three-dimensional experiments: HNCACB and CBCA(CO)NH for backbone assignment C-dipsi-(CO)NH, H-dipsi-(CO)NH, and $^{15}$N-edited NOESY for side-chain assignment, $^{15}$N-edited NOESY, $^{13}$C-edited NOESY (aliphatic and aromatic collected separately) for protein-protein NOE assignments, and $^{13}$C-filtered NOESY for protein-ligand NOE assignments, of which the latter exploited differences in isotopic labeling between the ligand (natural abundance, 99% $^{12}$C) and the protein (98% $^{13}$C) (Grzesiek, S. & Bax, A. (1993); Constantine, K. L. et al. (1993); Marion, D. et al. (1989); Zwahlen, C. et al. (1997)). Two conformations of the protein-ligand complex were visible in NMR spectra, with the apparent populations changing over time. The first conformation to appear (the kinetic product) disappeared over time until only the second conformation was visible (the thermodynamic product). Both conformations caused similar chemical shift perturbations and are likely to result from slight differences in ligand orientation within the same Tsg101 binding site. We chose to solve the structure of the more stable thermodynamic product since it would result in a higher quality structure.

Tsg101 UEV-N16 Structure Calculations

The structure of the Tsg101 UEV domain in complex with N16 was calculated using Xplor-NIH (Schwieters, C. D., et al. (2003); Schwieters, C. D., et al. (2006)). Simulated annealing was used in combination with NOE distance restraints, dihedral angle restraints, and hydrogen bond restraints. Distance restraints were calculated from NOE peak heights using CCPN Analysis 2.4.1 (Vranken, W. F. et al. (2005)). Dihedral angle restraints were derived from backbone chemical shift data using TALOS$^N$ (Shen, Y. & Bax, A. (2013)). Hydrogen bond restraints were obtained by predicting secondary structure propensity using MICS and combining with known hydrogen bonds from the Tsg101 UEV domain structure in the free form (PDB: 1KPP) (Shen, Y. & Bax, A. (2012); Pornillos, O. et al. EMBO J 21:2397-2406, doi:10.1093/emboj/21.10.2397 (2002)). 200 structures were calculated using simulated annealing, of which the 20 with lowest energy were used for further refinement. During the secondary refinement stage, 100 structures were calculated, with the inclusion of the Xplor-NIH 'repel' energy term to avoid atomic clashes, and a 'refRMSD' term to prevent calculated structures from straying too far from the lowest energy structure derived using simulated annealing. The 20 structures from the final refinement that were lowest in energy were chosen for the structural bundle presented here.

Results

N16 Inhibition of Infectious HIV-1 Production

To investigate whether the ability to bind the UEV domain could affect Tsg101's function during HIV's budding process, viral particle production was tested (FIG. 15). Addition of N16 six hours before the time of transfection with a plasmid containing the HIV genome (pNL4-3) resulted in a dose-dependent reduction in viral particle production from 293T cells, as indicated by the enzyme-linked immunosorbent assay (ELISA), a test that measures the concentration of the viral capsid (CA) p24 antigen in the cell culture medium ($EC_{50}$ between 25 and 50 µM, FIG. 15A, top). Addition of N16 at 24 hr post-transfection had little effect on budding even at higher concentrations (FIG. 15A, bottom). The latter suggested that the drugs were well-tolerated by cells and that the target of N16 inhibition is an early assembly event. The specific infectivity of the virus was diminished in dose-dependent fashion (FIG. 15B) although higher concentrations were required. N16 also reduced viral particle production in a spreading infection of Jurkat cells infected with NL4-3 (FIG. 16). After 15 days, virus production was reduced by 15-fold. Cell viability was maintained under these conditions of sustained drug exposure as indicated by trypan blue viability assay every 3rd day. Subsequent incubation in media without inhibitor resulted in a 10-fold resurgence of the virus after 4 days. Following the re-addition of N16 to the media, virus titer at this point was reduced 50-fold 4 days indicating maintenance of drug susceptibility.

N16 Arrest of Gag Budding

Electron microscopy was used to identify the event arrested by N16 treatment. Four morphologically identifiable stages comprise HIV-1 viral particle assembly: Deposition of electron-dense material at the cell surface is followed by progressive membrane deformation that results in a protruding bud that is eventually released as an immature virus particle. This particle undergoes morphogenetic rearrangement into the mature infectious particle (FIG. 15C, top, designated as 'Early', 'Tethered', 'Released Immature', and 'Released Mature', respectively). The untreated virus exhibited all of these stages to various degrees. N16 significantly aggravated the transition from 'Early' to 'Tethered', thereby impairing production of the mature particle. By comparison, interference with the $Gag^{PTAP}$ L domain interaction with Tsg101 by substitution of Leu for Pro7 (P7L) in the PTAP motif results in accumulation of mainly 'Tethered' immature-appearing particles bound either to the cell periphery or to each other in addition to the 'Early' form (Garrus, J. E. et al. (2001); Demirov, D. G., et al. J Virol 76, 105-117 (2002); Watanabe, S. M. et al. (2013)). Treatment of P7L with N16 blocked the residual particle release that the mutation permits (mediated by Alix, an ESCRT adaptor, Fujii, K. et al. (2009)) and shifted the predominant form detected from 'Tethered' to 'Early'. Collectively, the effect of N16 on WT and P7L budding suggests that the compound targets an event that occurs early in assembly, upstream of the event impacted by PTAP disruption and necessary for budding progression.

Figure 15C:
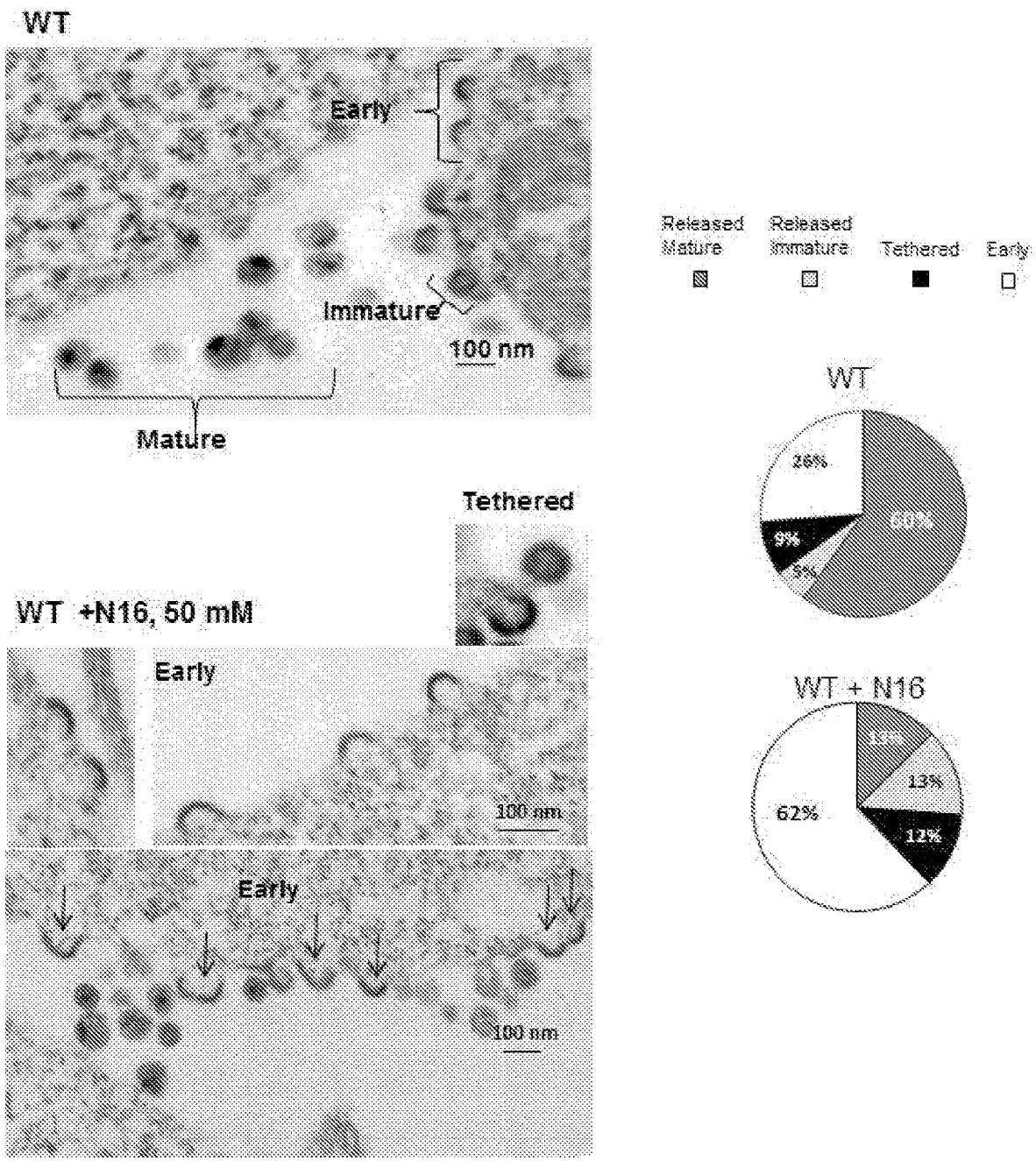
Figure 15D:
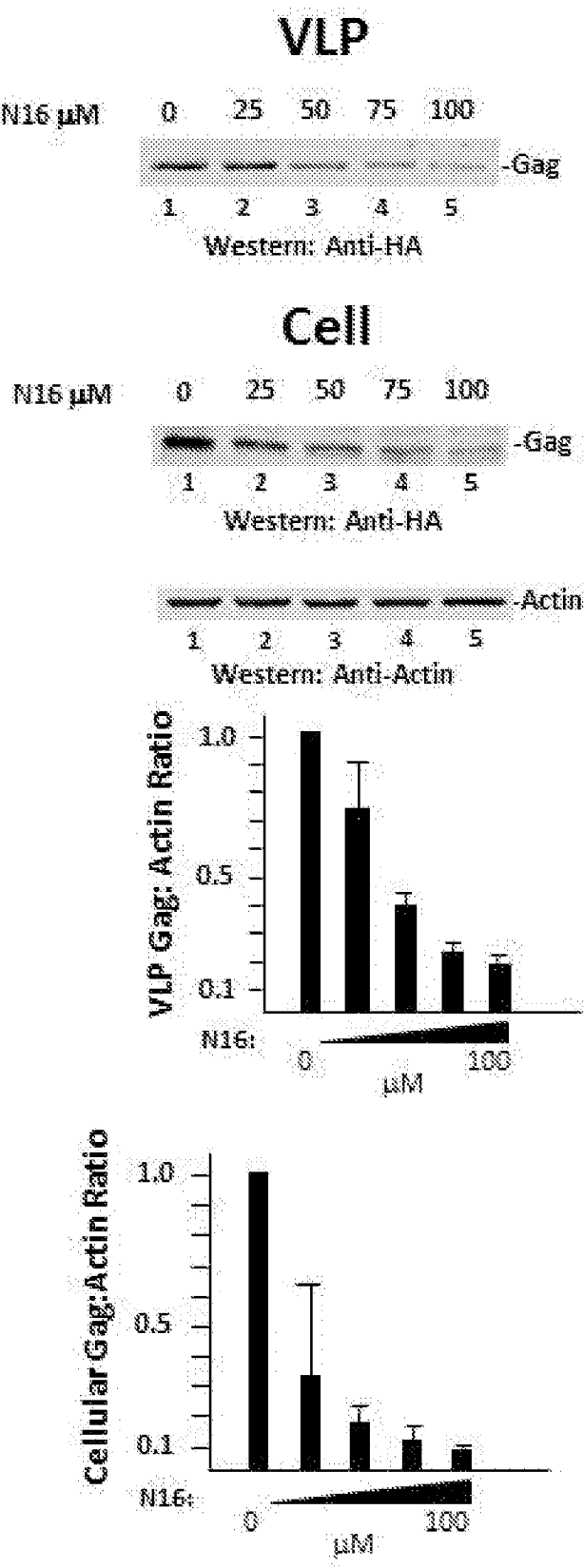

Since Tsg101 involvement in virus production is specific to trafficking and release of the assembled Gag polyprotein precursors, the mechanism underlying inhibition by investigating the effect on Gag function was studied. Gag contains all determinants necessary for formation and budding of immature virus-like particles (VLPs) (Ehrlich, L. S. & Carter, C. A. (2012); Dordor, A., et al. (2011)). As shown in FIG. 15D, N16 treatment was accompanied by dose-dependent reduction in both the steady-state level of Gag intracellular accumulation and the amount of VLP formation. Interestingly, however, although N16 also inhibited VLP release from HeLa cells, Gag intracellular accumulation was not affected (FIG. 17A). As shown in FIG. 17, treating cells with proteasome-specific inhibitor bortezomib (Goldberg, A. L. (2012)) throughout the period of N16 exposure failed to stabilize the cytoplasmic Gag (FIG. 17B). However, 'ex cellulo' treatment of cells (i.e., treatment just prior to cell lysate preparation) with a mixture of 25 µM MG132 (Goldberg, A. L. (2012)) (another proteasome inhibitor); and 10 µM N-ethylmaleimide (NEM; an inhibitor of the fusion of late endosomes and lysosomes) (Luzio, J. P., et al. (2007)) preserved Gag in the lysate. NEM alone was not effective. A mixture of proteases (aprotinin, 2 µg/ml; pepstatin, 1 µg/ml; leupeptin, 2.5 µg/ml; TPCK, 90 µM; and PMSF, 35 µg/ml) was also effective.

Figure 19E:
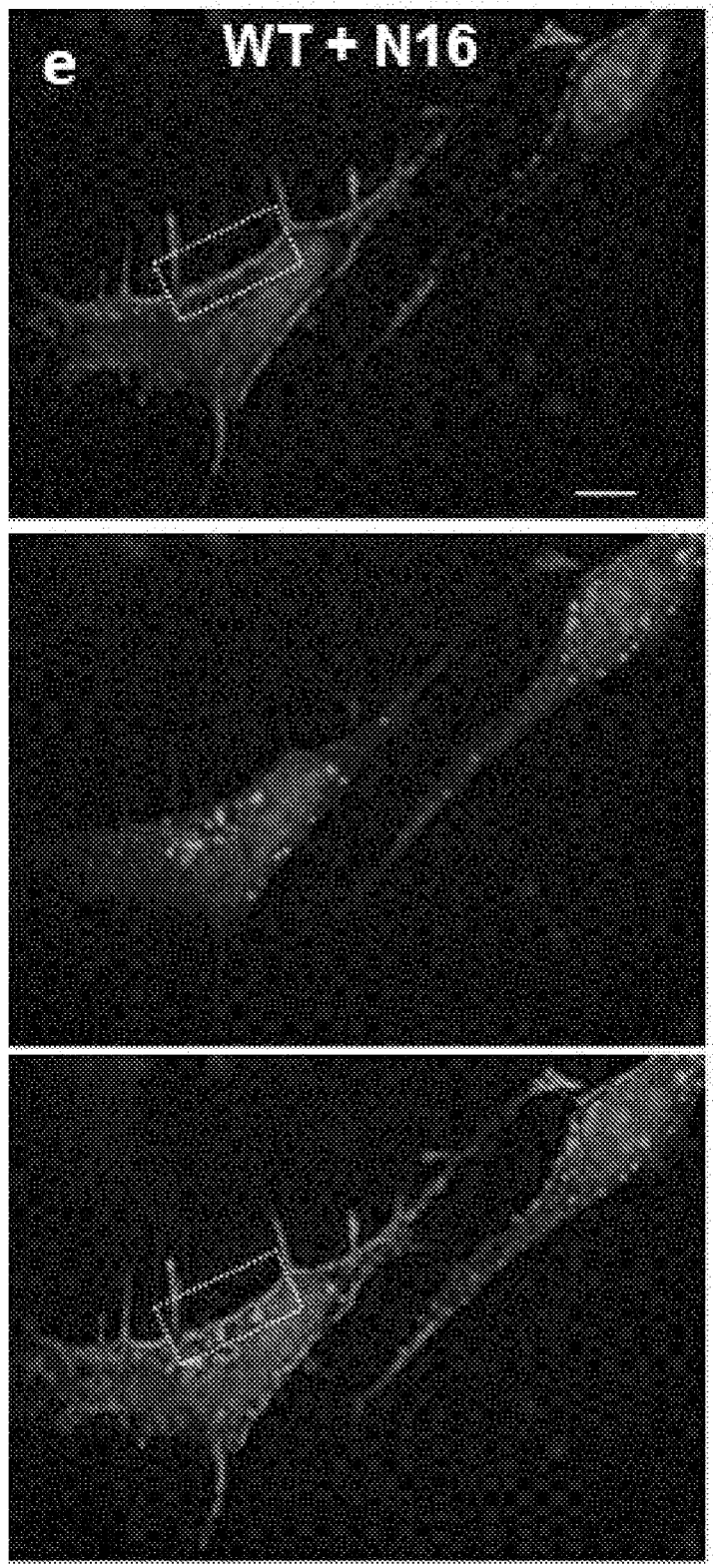
Figure 19F:
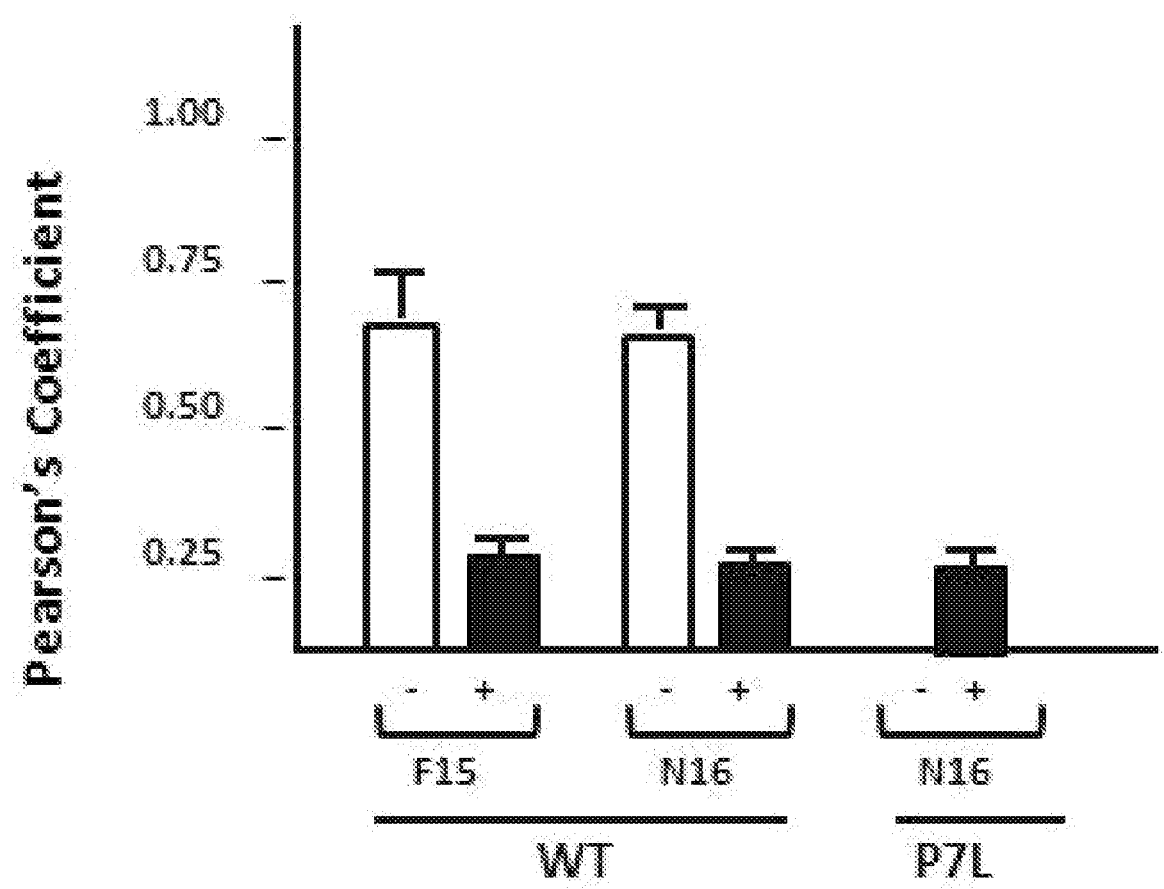

At steady-state, endogenous Tsg101 is detected in the cytosol and on the surface of endolysosomal vesicles (Bache, K. G., et al. (2003); Welsch, S. et al. (2006)). Western blot analysis revealed little change in partitioning of the protein to soluble (S1, S3) and particulate (P2, P3) subcellular fractions in the presence or absence of N16 (FIG. 18). Fluorescence microscopy was used to examine the effect of N16 on recruitment of Tsg101 by Gag to the plasma membrane. Previously shown aberrant enlarged (>200 nm in diameter) endosomal compartments induced by adventitious expression of the Tsg101 protein (or several other ESCRT subunits) (Goila-Gaur, R., et al. (2003); Eastman, S. W., et al. (2005)) were seen by fluorescence microscopy of cells expressing Tsg101 tagged with Myc (FIG. 19A, top). N16 induced no apparent change in the size or location of these structures (FIG. 19A, bottom). HIV-1 $Gag^{WT}$-GFP (FIG. 19B, top) co-localized with Myc-tagged Tsg101 (FIG. 19B, middle) in these structures and in smaller puncta on the plasma membrane (FIG. 19B, bottom). The $Gag^{P7L}$ mutant localized to the cell periphery (FIG. 19C, top, boxed region) however, as expected since its PTAP motif is disrupted, co-localization with Tsg101 (FIG. 19C, middle) was not detected (FIG. 19C, bottom). Under these conditions, Tsg101-Myc was detected as large puncta (~200-300 nm) in the cell interior. To identify the N16-sensitive event, we determined the effect of the compounds following treatment. Like the PTAP mutation in Gag, F15 (FIG. 19D) and N16 (FIG. 19E) did not interfere with the accumulation of Gag on the plasma membrane (top panels); however, they prevented Gag-Tsg101 co-localization at this site (bottom panels) indicating that they both blocked Tsg101 accumulation at the plasma membrane. With both F15 and N16, Tsg101-Myc was detected as large puncta in the cell interior (FIG. 19D middle and FIG. 19E middle) and, although significantly less overall Gag-Tsg101 co-localized puncta were detected, the ones detected were detected exclusively in the cell interior. Thus, the affected Tsg101 function was not Tsg101-Gag association per se. A comparison of Pearson's coefficient of correlation values (Manders, E. M. M., et al. (1993)) for Gag-Tsg101 colocalization in the presence or absence of N16 is shown in panel 19F: Treatment with F15 or N16 reduced the intensity of the co-localization signal by ~2-fold. We conclude that the F15 and N16 agents interfere with a Tsg101 function that determines Gag's ability to stably recruit the protein to virus assembly sites on the plasma membrane.

N16 Specificity to Anti-Viral Effect

We investigated the specificity of the inhibitory effect. F15 and N16 impaired Tsg101-co-localization with Gag on the plasma membrane (c.f, FIG. 19) and reduced release of the VLPs assembled by Gag (c.f, FIG. 15). Under the same conditions (50 µM, 24 hr exposure), the N16 compound did not induce detectable cytotoxicity, nor did it interfere with the Tsg101 steady-state level, with well-established cell-specified Tsg101 functions such as Tsg101 localization to the mid-body of cells undergoing the abscission stage of cytokinesis (Carlton, J. G. & Martin-Serrano, J. (2007)) nor with epidermal growth factor receptor (EGFR) down-regulation (Lu, Q., et al. (2003)) (FIG. 20; F15 was not tested). Cell metabolic activity was not affected after exposure to N16 for 24 hr; it decreased by less than 10% after exposure to N16 for 48 hr (not shown). Tsg101 localization to the midbody of dividing cells requires its recruitment to that location by centrosomal protein of 55k (CEP55) which binds a site in the Tsg101 Pro-rich domain (aa 154-166) (Lee, H. H., et al. (2008)). Finding this function unaffected at a concentration inhibitory to virus budding is consistent with the lack of any indication that cell division was reduced in the presence of N16. The lack of effect on this function also supports the specificity of N16 targeting as limited to functions of the Tsg101 UEV domain. EGF ligand-binding to EGFR on the cell surface signals receptor internalization, ubiquitination, and sequential ESCRT 0-, I-, II- and III- mediated transport to degradative compartments, ultimately lowering the EGFR steady-state level (Tomas, A., et al. (2014)). This trafficking requires the engagement of the P(T/S)AP-binding pocket in the Tsg101 UEV domain with the PSAP motif in hepatocyte growth factor-regulated tyrosine kinase substrate (Hrs), a component of ESCRT-0 (Lu, Q., et al. (2003)). The down-regulation function remained unimpaired at concentrations well above 50 JAM. The results indicated that well-established cell-directed Tsg101 functions were resistant to N16 at the concentration to which virus production was susceptible.

Fusing a De-Ubiquitinating Enzyme to Gag Conferred Resistance to N16

The fact that fusion of Ub to Gag increases budding efficiency has been reported widely (Patnaik, A., et al. (2000); Joshi, A., et al. (2008); Zhadina, M. & Bieniasz, P. D. (2010)). In contrast, Sette et al. observed that fusion of a de-ubiquitinating enzyme (DUb) to Gag decreased budding efficiency. We confirmed this observation (see below, FIG. 21A). Together these observations indicate that Ub and DUb contribute to budding in opposing manners. It has also been widely reported that mutation of the PTAP motif in HIV-1 Gag leads to increased Gag ubiquitination (Martin-Serrano, J., *J Virol* 79, 9134-9144, doi:10.1128/JVI.79.14.9134-9144.2005 (2005); Hahn, S., et al. (2011)). This observation suggests that Tsg101 binding to Gag might be accompanied by recruitment of a Ub peptidase that removes Ub from Gag. Previous studies indicated that Vps23, the orthologue of Tsg101 in yeast, and Doa4, a deubiquitinating enzyme, were both required for removal of Ub from endosomal cargo prior to initiation of multivesicular body (MVB) formation (Katzmann, D. J., et al. (2001)). As budding from the plasma membrane is considered to be topologically equivalent to MVB formation, it seemed possible that the observed increased accumulation of early budding structures following N16 treatment (c.f., FIG. 15C) was a manifestation of disrupted Ub dynamics during the budding process. If opposing functions of Ub and DUb are both required for budding the imbalance caused by DUb fusion to Gag, whose negative impact on budding was shown previously (Sette et al. (2013)) and recapitulated in FIG. 21A, might be reversed by the N16 targeting of Tsg101.

To test this hypothesis, the effect of N16 on Gag fused to DUb was examined in the absence and presence of N16 (FIG. 21). FIG. 21A (top panel) shows that fusion of the catalytic domain of the Herpes Simplex virus UL36 deubiquitinating enzyme (DUb) onto Gag inhibited budding, as expected based on previous studies (Sette et al.). Quantitative analysis indicated that VLP release efficiency was reduced ~50-fold (FIG. 21 A, bottom panel). FIG. 21B shows the effect of N16. As expected based on the results above, budding directed by WT Gag was inhibited by 50 µM N16 (FIG. 21B, top, left). In contrast, budding of the DUb fusion was not inhibited when N16 was present (FIG. 21B, top, right). Also interestingly, although the N16-imposed vulnerability of the intracellular Gag was unchanged (FIG. 21B bottom, center), the overall VLP release efficiency was increased (FIG. 21B, bottom, right). The results clearly indicate that the inhibitory effect of N16 treatment can be opposed by DUb, suggesting that the drug targets a previously unappreciated Tsg101 function linked to Ub dynamics during the budding process.

N16 Disruption of Ub Binding to the Tsg101 UEV Domain

Figure 14F:
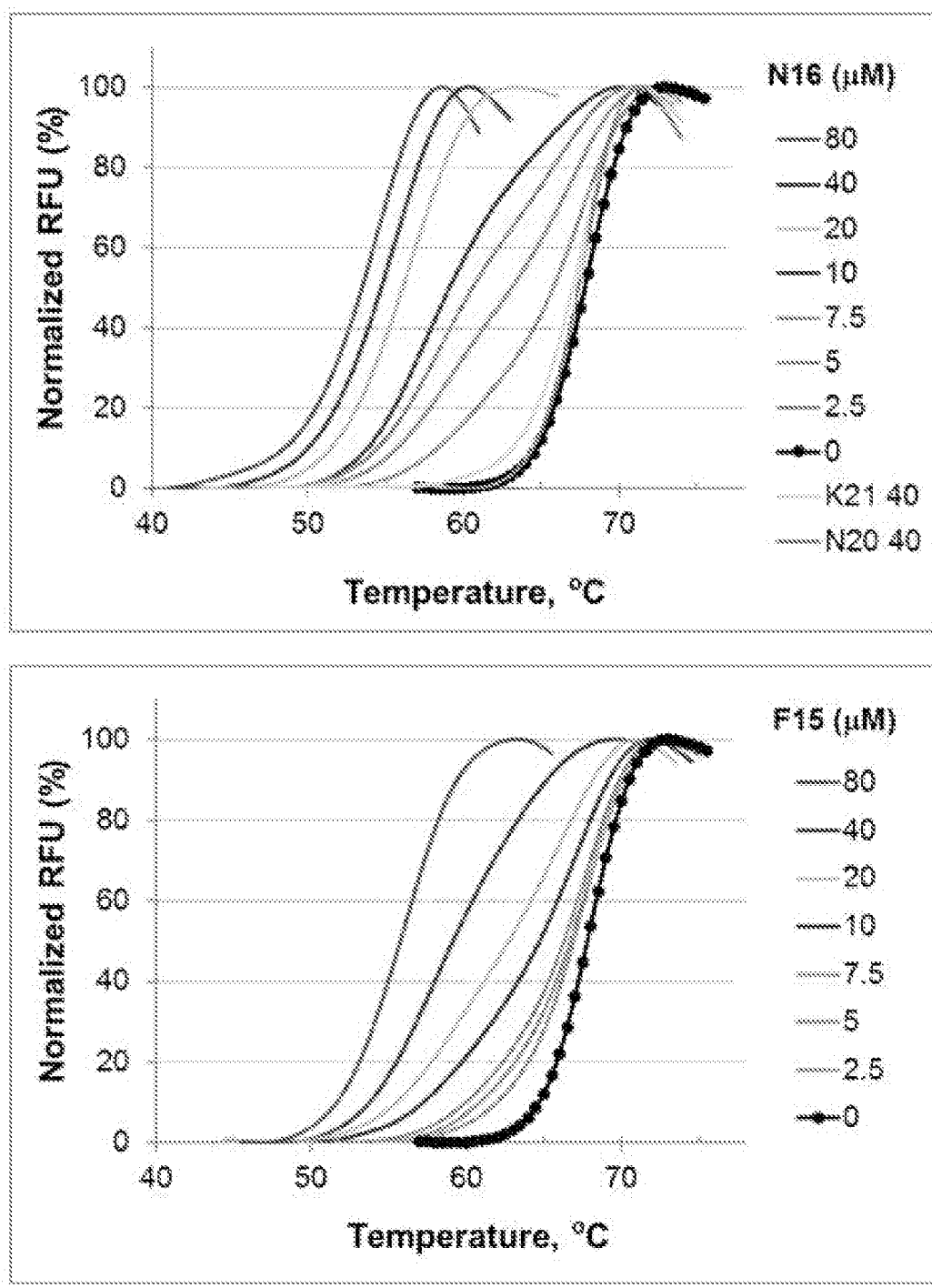

The high-resolution structure of the N16-Tsg101 UEV complex was solved using NMR, and the atomic interactions between N16 and Tsg101 were probed (PDB ID 5VKG, BMRB ID 30285, FIG. 14). The N16 binding site of Tsg101 comprised a region surrounding residue C73 that included D40, S41, Y42, N54, T56, W75 and K90 (FIGS. 22A and 22B), which correlated well with the observed chemical shift perturbations of N16 with Tsg101 (FIGS. 22C and 22D, 23). The interaction was stabilized by aromatic π-stacking between the imidazopyridine ring of N16 with residues Y42 and W75 of Tsg101, hydrophobic interactions with T56, and hydrogen bonding between aryl methoxy groups of N16, the backbone NH of S41 and the side-chain amine of K90 (FIG. 22B). Tsg101 chemical shift perturbations caused by PTAP binding showed the same general profile with and without pre-incubation of N16, with some differences around residues 87-98 (FIGS. 22E and 22F, 24). This contrasts with the Ub-binding pocket perturbation profile, which indicated N16 interfered throughout the pocket resulting in a significantly lower Tsg101-Ub binding affinity in the presence of N16 (FIGS. 22G and 22H, 25).

Figure 26A:
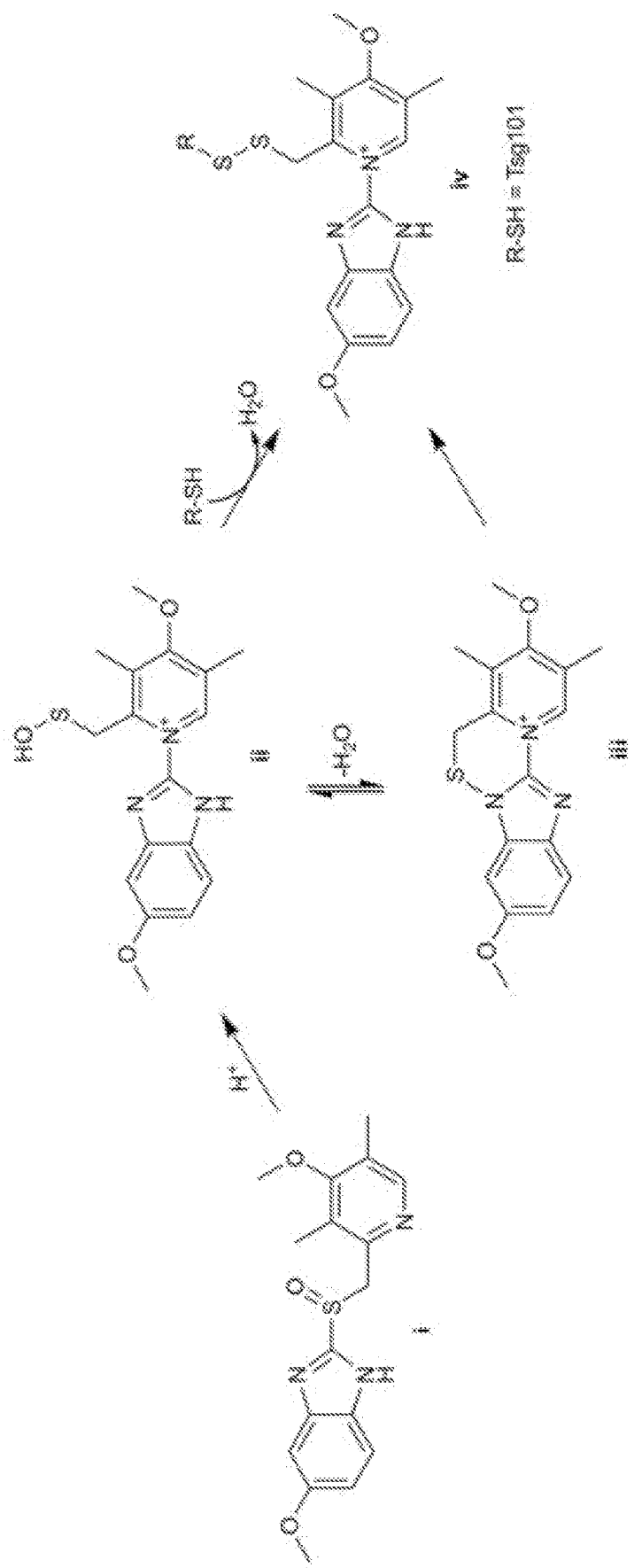
Figure 26B:
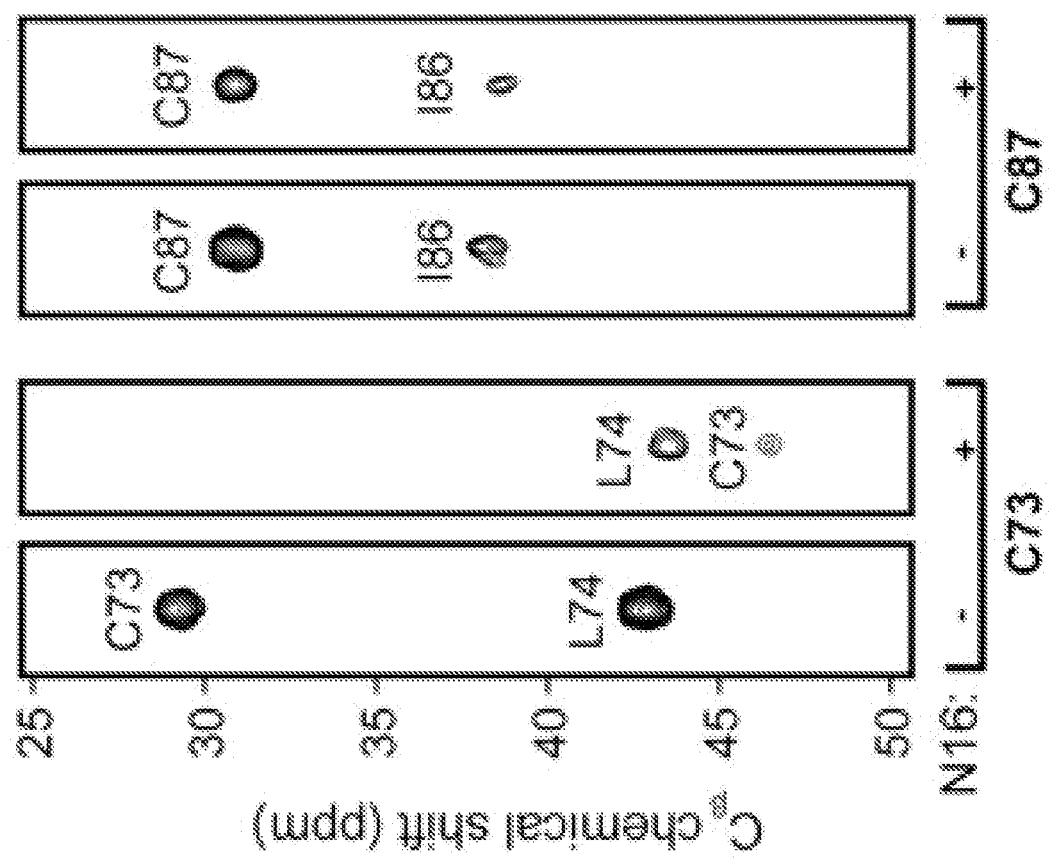
Figure 26C:
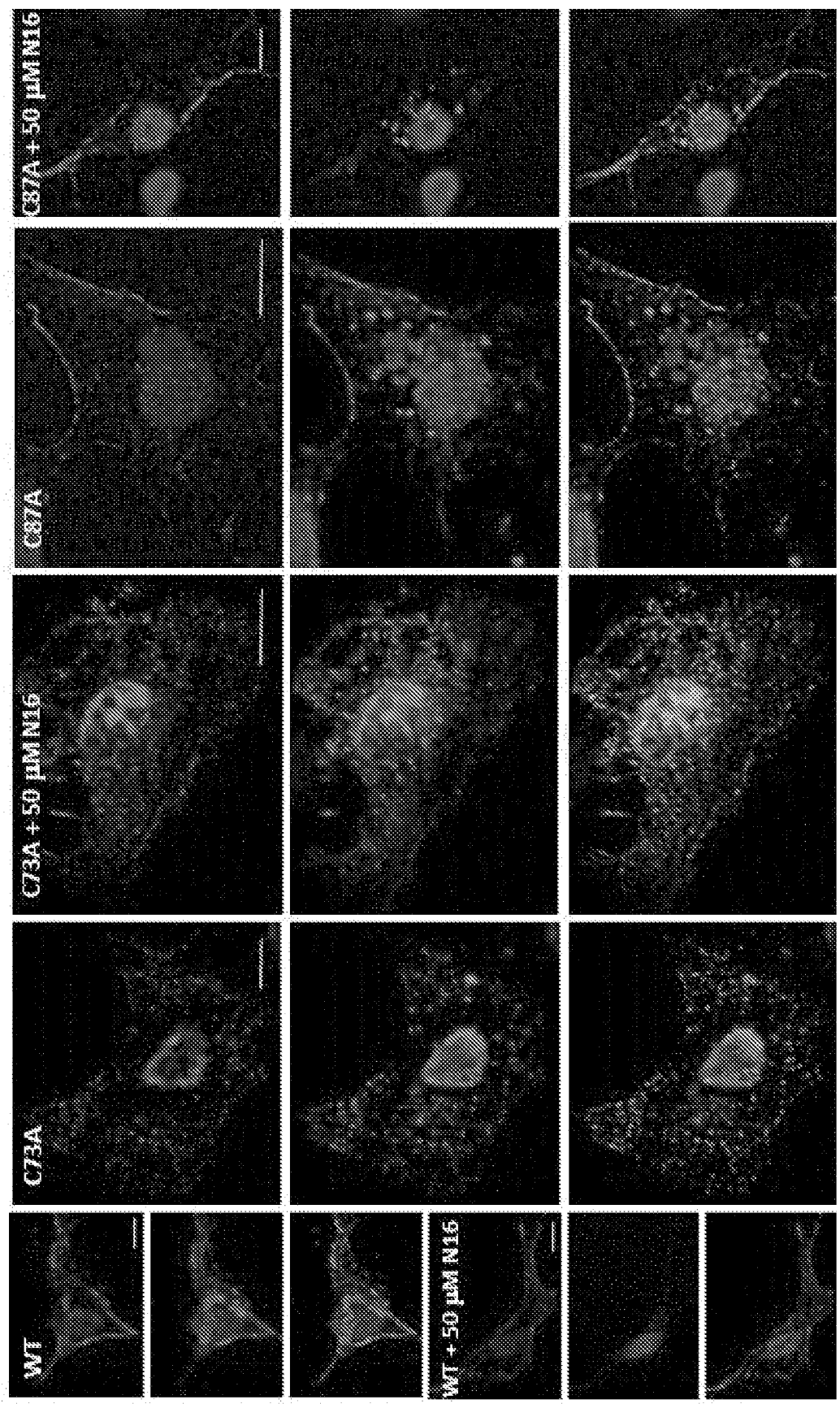
Figure 26D:
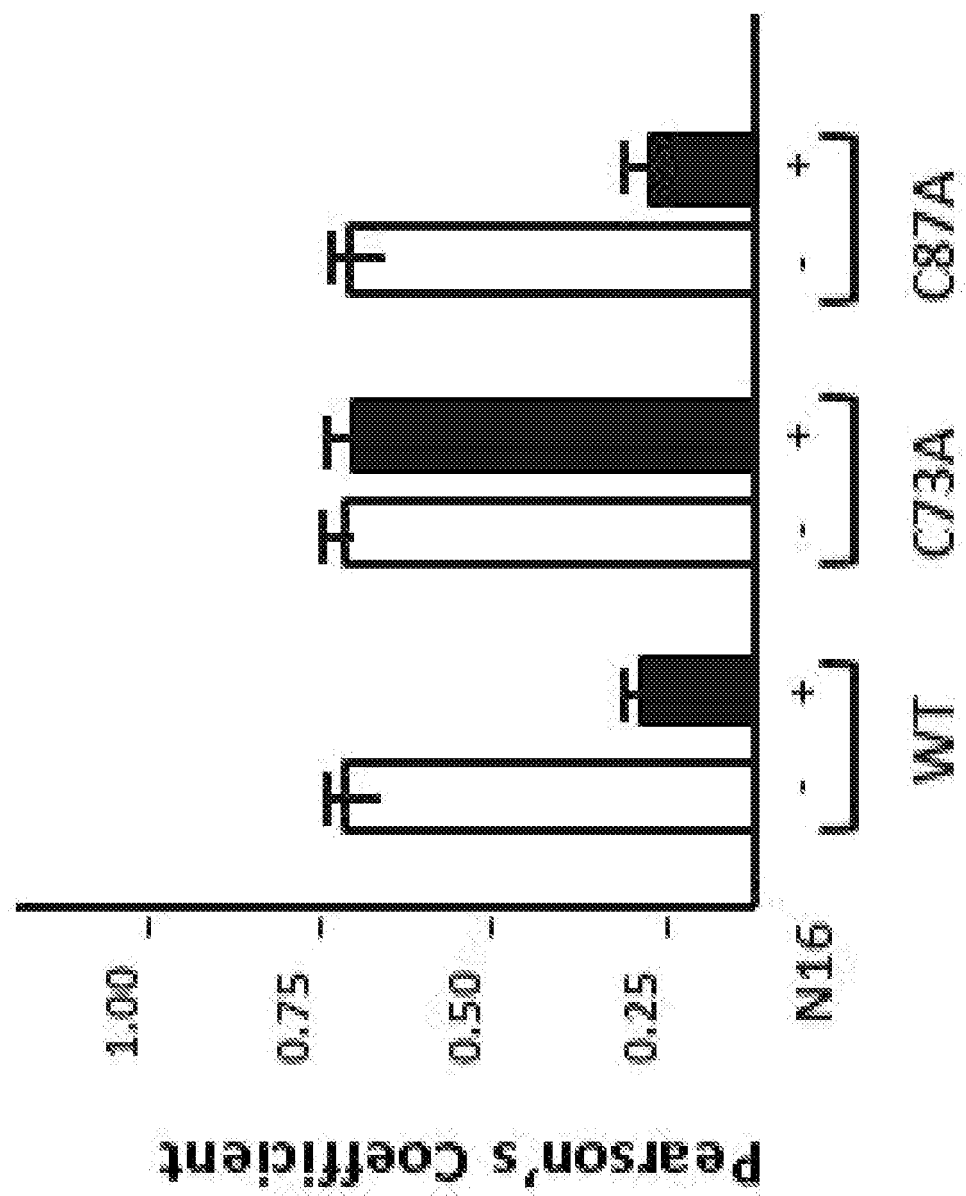

N16 (FIG. 26A, i) is a prodrug that is acid-activated into derivatives (FIG. 26A, ii and iii) that form disulfide linkages (e.g., FIG. 26A, iv) (Shin, J. M. & Kim, N. (2013)). The prodrug, but not the charged sulfenamide derivative, can cross the plasma membrane barrier. It was hypothesized that Cys73, the Cys residue in the Tsg101 UEV domain that was perturbed by N16, formed a disulfide linkage with a derivative produced inside the cell following N16 uptake. Mass spectrometry was performed to examine for covalent bond formation following mixing of drug and the Tsg101 UEV domain. This analysis revealed that the interaction between N16 and UEV was covalent, consistent with prodrug conversion to the active sulfenamide form under the conditions of the experiment. The specificity of the effect was confirmed by demonstrating that the addition of N-acetyl Cysteine, an antioxidative reagent, prevented the N16 effect (FIG. 27). NMR spectroscopy indicated that the β-carbon of Tsg101 residue C73, but not C87, was shifted after N16 binding from ~30 ppm to ~45 ppm as is typical of covalent binding (FIG. 26B). If the sulfenamide derivative of N16 serves as the antiviral agent in the cellular milieu, the substitution of Ala for C73, but not C87, is predicted to permit Gag-Tsg101 co-localization in the presence of the drug by preventing the covalent blockade. As shown in FIGS. 26C and 26D, N16 failed to prevent co-localization of Gag and Tsg101$^{C73A}$-myc. However, N16 effectively eliminated co-localization of Gag and Tsg101$^{C87A}$-myc. Moreover, if Tsg101 residue C73 is the target of N16, then knocking down endogenous Tsg101 and providing a siRNA-resistant version of the C73A mutant should render HIV-1 assembly/release insensitive to N16. This prediction was supported by resistance of budding to N16 treatment in in C73A replaced cells. This contrasted with the N16 sensitivity of budding in cells where endogenous Tsg101 was replaced with a siRNA-resistant version of the WT protein (FIG. 28). These findings provide further support for the conclusion that Tsg101 is the target of N16 in living cells. Moreover, they demonstrate that C73, the NMR-postulated target of the active drug form, is one of the residues essential for the antiviral effect.

Discussion

The known role of Tsg101 in HIV-1 production is as conduit to the membrane-remodeling machinery associated with ESCRT-III, which is required for virus budding (Hurley, J. H. & Hanson, P. I. (2010); Adell, M. A. & Teis, D. (2011); Votteler, J. & Sundquist, W. 1. (2013)). The Tsg101-Gag$^{PTAP}$ binding activity is mainly responsible for the virus' ability to recruit Tsg101 to Gag assembly sites on the plasma membrane. Determinants within Gag direct the complex to budding sites on the plasma membrane where the Tsg101-mediated recruitment of ESCRT-III membrane scission machinery facilitates virus particle release from the cell. The findings described here indicate that the productive interaction of Gag with the Ub-binding pocket in Tsg101 is another critical contribution, as it facilitates productive sorting of the protein and progression through the budding stages to ultimate egress. Here or in the cytosol, Gag ubiquitination permits engagement of the Tsg101 Ub-binding pocket, which for WT Gag serves to significantly increase Gag-Tsg101 binding affinity (Pornillos et al., *EMBO J* 21, 2397-2406, (2002)) and for P7L, provides a way of recruiting Tsg101. The inventor hypothesize that, following UEV binding of F15 and N16 compounds, allosteric changes that disturb the Tsg101 Ub-binding pocket prevent plasma membrane localization of the Gag-Tsg101 complex, resulting in the apparently delayed evagination of Gag assemblages on the plasma membrane. For P7L-Gag, if released VLPs represent Ub-modified P7L Gag molecules that bound Tsg101 though the Ub-binding pocket, the compounds can be expected to prevent such release. However, this mode of contribution to budding by the Ub-binding pocket does not adequately explain the fact that known inhibitory effects (i.e., tethered particles, defective maturational p25 to p24 processing, polyubiquitination and single released particles arrested in the immature state) from disruption of the Gag-Tsg101 interaction in various ways (Tsg101 depletion (Garrus et al.), PTAP mutation (Demirov et al., J Virol 76, 105-117 (2002); Martin-Serrano, J. & Bieniasz, P. D. (2003); Goff, A., et al. (2003)), dominant-negative Tsg101 expression (Goila-Gaur et al. (2003); Goff, A., et al. (2003); Demirov et al., *Proc Natl Acad Sci USA* 99, 955-960, doi:10.1073/pnas.032511899 (2002))) are clearly distinct from those resulting from exposure to F15 and N16 (aggravated accumulation of 'Early' buds). These differences do not appear to result from off-target effects of the compounds as we eliminated cell toxicity and lack of functional specificity as likely explanations. Rather, the interaction of Gag with the Ub-binding pocket in Tsg101 appears critical for initiating the budding event.

Regarding the Gag instability imposed by N16 treatment of 293T cells, it is of interest that treatments to Tsg101 (depletion followed by replacement with C73A) or Gag (fusion of DUb to Gag) were capable of rescuing the N16-induced inhibition of VLP budding but had no detectable impact on the drug-induced Gag instability (FIG. 28 and FIG. 21, respectively). In contrast, the N16-induced Gag instability was blocked by treatment with MG132 (FIG. 17). Interestingly, the proteasome inhibitor, bortezomib (Goldberg (2012)), a dipeptide which reversibly inhibits the chymotrypsin-like activity at the β5-subunit of proteasome (PSMB5) had no apparent impact on the N16-induced inhibition of Gag budding and instability. MG132 is a structurally & functionally unrelated proteasome inhibitor which reversibly blocks all activities of the 26S proteasome but is not as specific as bortezomib (Goldberg (2012)). MG132 is known to have off-target effects, e.g., it inhibits calpain and clasto-Lactacystin β-lactone which inhibits cathepsin A. Although Schwartz et al. (Schwartz, O., et al. (1998)) showed that treatment of target cells with the proteasome inhibitors MG132 and lactacystin increased the early steps of HIV infection, Schubert et al. demonstrated that virus assembly, maturation & budding require an active proteasome system. (For that reason, we did not conduct 'in cellulo' MG132 treatments). Interestingly, like N16, pretreatment of HIV-1 infected cells with MG132 enhances its inhibitory effect (Schubert, U. et al. (2000)), suggesting that it, like N16, targets an early event in the budding pathway. However, in contrast to N16 treatment, MG132 treatment results in ultrastructural changes in budding virions similar to those resulting from mutations in the PTAP Late assembly domain (Schubert, U. et al. (2000)), while the impact of N16 appears to be at an earlier stage. In any event, the observation that MG132 (NEM contribution to be defined) can oppose the N16-induced Gag instability while bortezomib did not, makes it unlikely that a specific complex like the proteasome is responsible. Consistent with this, we observed that the Gag lability could also be prevented by lysing cells in the presence of a mixture of protease inhibitors, as described in the text. At this point, is not clear whether the Gag-destabilizing effect of N16 observed in 293T but not HeLa cells is an "off-target" effect of N16 in 293T cells or is in some way linked to an indirect impact on Tsg101 function in those cells.

This application proposes a Tsg101 chaperone function that is based on the participation of the Ub binding pocket in temporal and/or spatial balancing of Gag ubiquitination and deubiquitination during budding. This adds Tsg101 to a list with proteins like BAG (Schonbuhler, B. et al. (2016)), cdc48/97 (Bonizec, M. et al. (2014)) and PDCL3 (Srinivasan, S., et al. (2013)) that fulfill their chaperoning function by influencing ubiquitination. Through this chaperone function, Tsg101 makes a previously unappreciated contribution to virus budding that appears to be required early in the budding process and distinct from the recruitment of ESCRT-III that is critical to HIV egress. Moreover, this function is required whether or not the PTAP pocket in the Tsg101 protein is engaged, as evident from P7L susceptibility. Possibly, as the binding is covalent, the F15/N16-modified Tsg101 might exert a trans-dominant-negative interfering influence on a function required for Alix-mediated P7L budding and thereby affect egress even if direct binding does not normally occur. That both Tsg101-driven and Alix-driven budding was inhibited by an agent (N16) that disrupts Tsg101 Ub-binding activity implies a requirement for this Tsg101 chaperone function in a fundamental aspect of budding.

Targeting of the Gag-Tsg101 interaction for inhibition of HIV budding has been an active field over the last fifteen years, mostly focusing on interference with PTAP binding (Tavassoli, A. et al. (2008); Chen, H., et al. (2010); Kim, S. E. et al. (2011); Lu, J. et al. (2014)). Theoretically, a synthetic peptide that mimics the PTAP motif could compete for the PTAP binding pocket of Tsg101 in cells. The wild-type synthetic peptide $^5$PEPTAPPEE[13] displays a low binding affinity to Tsg101 in vitro, with a $K_d$ of 54 µM (Liu, F. et al. (2008)), however, a significant increase in affinity can be achieved by introducing a bulkier and more hydrophobic group at the first proline in the PTAP motif (Kim, S. E. et al. (2011); Liu, F. et al. (2008)). Although high-resolution structures for the highest affinity complexes have not yet been elucidated, docking studies indicate that these PTAP inhibitors bind to the hydrophobic surface of Tsg101 around residue T56 (Kim, S. E. et al. (2011)). Interestingly, this binding interface overlaps with the N16 interface, underscoring the importance of that hydrophobic surface. Cyclic peptides have also been shown to inhibit the Gag-Tsg101 interaction (Tavassoli, A. et al. (2008)). Several cyclic peptides structurally unrelated to PTAP but exhibiting high Tsg101 binding affinity inhibited HIV-1 VLP release >60% when covalently attached to the HIV Tat protein to facilitate their passage through the cell membrane. These peptides also inhibited the Tsg101-PSAP-Hrs interaction but had no apparent effect on EGFR degradation at low concentrations. The present studies demonstrate the ability of small molecules like F15 and N16 to interfere with a previously unrecognized Tsg101 contribution to budding. The findings suggest that F15/N16 could most likely be used at higher concentrations than these PTAP-based inhibitors without adversely affecting normal cellular function. Indeed, the dose of N16 provided is 40 milligrams. Seven microgram/ml is achieved in human plasma (Hunt, R. H. et al. (2005)), a level that is equivalent to a 20 micromolar concentration of the drug. The lowest concentration that we achieved in tissue culture assays when N16 was provided under the optimal conditions described in the text (c.f FIG. 15) was 25-50 micromolar. The current availability of the F15/N16 compounds in diverse long-acting slow-release formulations is another feature adaptable to further refined development of the F15/N16 compounds that could address issues pertaining to drug regimen adherence. Most important to the goal of targeting this newly appreciated contribution of Tsg101 for development of next-generation antiviral agents, the structure of the N16-Tsg101 interaction is of sufficiently high resolution to be used in further development of improved Tsg101 inhibitors. Thus, findings described here present the Tsg101 UEV Ub binding activity as a novel target that can be exploited for antiviral drug design.

REFERENCES

Adell, M. A. & Teis, D. Assembly and disassembly of the ESCRT-III membrane scission complex. *FEBS Lett* 585, 3191-3196, (2011).

Bache, K. G., Brech, A., Mehlum, A. & Stenmark, H. Hrs regulates multivesicular body formation via ESCRT recruitment to endosomes. *J Cell Biol* 162, 435-442 (2003).

Bonizec, M. et al. The ubiquitin-selective chaperone Cdc48/p97 associates with Ubx3 to modulate monoubiquitylation of histone H2B. *Nucleic Acids Res* 42, 10975-10986(2014).

Carlton, J. G. & Martin-Serrano, J. Parallels between cytokinesis and retroviral budding: a role for the ESCRT machinery. *Science* 316, 1908-1912 (2007).

Chen, H., Liu, X., Li, Z., Zhan, P. & De Clercq, E. TSG101: a novel anti-HIV-1 drug target. *Curr Med Chem* 17, 750-758 (2010).

Constantine, K. L. et al. Aliphatic 1H and 13C resonance assignments for the 26-10 antibody VL domain derived from heteronuclear multidimensional NMR spectroscopy. *J Biomol NMR* 3, 41-54 (1993).

Delaglio, F. et al. NMRPipe: a multidimensional spectral processing system based on UNIX pipes. *J Biomol NMR* 6, 277-293 (1995).

Demirov, D. G., Orenstein, J. M. & Freed, E. O. The late domain of human immunodeficiency virus type 1 p6 promotes virus release in a cell type-dependent manner. *J Virol* 76, 105-117 (2002).

Demirov, D. G., Ono, A., Orenstein, J. M. & Freed, E. O. Overexpression of the N-terminal domain of TSG101 inhibits HIV-1 budding by blocking late domain function. *Proc Natl Acad Sci USA* 99, 955-960, (2002).

Dordor, A., Poudevigne, E., Gottlinger, H. & Weissenhom, W. Essential and supporting host cell factors for HIV-1 budding. *Future Microbiol* 6, 1159-1170 (2011).

Dupre et al., Ubiquitin and endocytic internalization in yeast and animal cells. *Biochim Biophys Acta.* 1695, 89-111 (2004).

Eastman, S. W., Martin-Serrano, J., Chung, W., Zang, T. & Bieniasz, P. D. Identification of human VPS37C, a component of endosomal sorting complex required for transport-I important for viral budding. *J Biol Chem* 280, 628-636 (2005).

Ehrlich, L. S. & Carter, C. A. HIV Assembly and Budding: Ca(2+) Signaling and Non-ESCRT Proteins Set the Stage. *Mol Biol Int* 2012, 851670 (2012).

Fujii, K. et al. Functional role of Alix in HIV-1 replication. *Virology* 391, 284-292(2009).

Garrus, J. E. et al. Tsg101 and the vacuolar protein sorting pathway are essential for HIV-1 budding. *Cell* 107, 55-65 (2001).

Goff, A., Ehrlich, L. S., Cohen, S. N. & Carter, C. A. Tsg101 control of human immunodeficiency virus type 1 Gag trafficking and release. *J Virol* 77, 9173-9182 (2003).

Goila-Gaur, R., Demirov, D. G., Orenstein, J. M., Ono, A. & Freed, E. O. Defects in human immunodeficiency virus budding and endosomal sorting induced by TSG101 overexpression. *J Virol* 77, 6507-6519 (2003).

Goldberg, A. L. Development of proteasome inhibitors as research tools and cancer drugs. *J Cell Biol* 199, 583-588 (2012).

Gottwein, E. & Krausslich, H. G. Analysis of human immunodeficiency virus type 1 Gag ubiquitination. *J Virol* 79, 9134-9144 (2005).

Grzesiek, S. & Bax, A. Amino acid type determination in the sequential assignment procedure of uniformly 13C/15N-enriched proteins. *J Biomol NMR* 3, 185-204 (1993).

Hahn, S., Setz, C., Wild, J. & Schubert, U. The PTAP sequence within the p6 domain of human immunodeficiency virus type 1 Gag regulates its ubiquitination and MHC class I antigen presentation. *J Immunol* 186, 5706-5718 (2011).

Hunt, R. H. et al. Effect on intragastric pH of a PPI with a prolonged plasma half-life: comparison between tenatoprazole and esomeprazole on the duration of acid suppression in healthy male volunteers. *Am J Gastroenterol* 100, 1949-1956 (2005).

Hurley, J. H. ESCRT complexes and the biogenesis of multivesicular bodies. *Curr Opin Cell Biol* 20, 4-11 (2008).

Hurley, J. H. & Hanson, P. I. Membrane budding and scission by the ESCRT machinery: it's all in the neck. *Nat Rev Mol Cell Biol* 11, 556-566 (2010).

Joshi, A., Munshi, U., Ablan, S. D., Nagashima, K. & Freed, E. O. Functional replacement of a retroviral late domain by ubiquitin fusion. *Traffic* 9, 1972-1983(2008).

Katzmann, D. J., Babst, M. & Emr, S. D. Ubiquitin-dependent sorting into the multivesicular body pathway requires the function of a conserved endosomal protein sorting complex, ESCRT-I. *Cell* 106, 145-155 (2001).

Kim, S. E. et al. Elucidation of New Binding Interactions with the Tumor Susceptibility Gene 101 (Tsg101) Protein Using Modified HIV-1 Gag-p6 Derived Peptide Ligands. *ACS Med Chem Lett* 2, 337-341 (2011).

Koonin, E. V. & Abagyan, R. A. TSG101 may be the prototype of a class of dominant negative ubiquitin regulators. *Nat Genet* 16, 330-331 (1997).

Lazar, G. A., Desjarlais, J. R. & Handel, T. M. De novo design of the hydrophobic core of ubiquitin. *Protein Sci* 6, 1167-1178(1997).

Lee, H. H., Elia, N., Ghirlando, R., Lippincott-Schwartz, J. & Hurley, J. H. Midbody targeting of the ESCRT machinery by a noncanonical coiled coil in CEP55. *Science* 322, 576-580(2008).

Li, L., Liao, J., Ruland, J., Mak, T. W. & Cohen, S. N. A TSG101/MDM2 regulatory loop modulates MDM2 degradation and MDM2/p53 feedback control. *Proc Natl Acad Sci USA* 98, 1619-1624(2001).

Liu, F. et al. SAR by oxime-containing peptide libraries: application to Tsg101 ligand optimization. *Chembiochem* 9, 2000-2004 (2008).

Lu, J. et al. A host-oriented inhibitor of Junin Argentine hemorrhagic fever virus egress. *J Virol* 88, 4736-474313 (2014).

Lu, Q., Hope, L. W., Brasch, M., Reinhard, C. & Cohen, S. N. TSG101 interaction with HRS mediates endosomal trafficking and receptor down-regulation. *Proc Natl Acad Sci USA* 100, 7626-7631 (2003).

Luzio, J. P., Pryor, P. R. & Bright, N. A. Lysosomes: fusion and function. *Nat Rev Mol Cell Biol* 8, 622-632 (2007).

Manders, E. M. M., Verbeek, F. J. & Aten, J. A. Measurement of Colocalization of Objects in Dual-Color Confocal Images. *Journal of Microscopy-Oxford* 169, 375-382 (1993).

Marion, D. et al. Overcoming the overlap problem in the assignment of 1H NMR spectra of larger proteins by use of three-dimensional heteronuclear 1H-15N Hartmann-Hahn-multiple quantum coherence and nuclear Overhauser-multiple quantum coherence spectroscopy: application to interleukin 1 beta. *Biochemistry* 28, 6150-6156 (1989).

Martin-Serrano, J., Zang, T. & Bieniasz, P. D. HIV-1 and Ebola virus encode small peptide motifs that recruit Tsg101 to sites of particle assembly to facilitate egress. *Nat Med* 7, 1313-1319 (2001).

Martin-Serrano, J. & Bieniasz, P. D. A bipartite late-budding domain in human immunodeficiency virus type 1. *J Virol* 77, 12373-12377 (2003).

Martin-Serrano, J., Perez-Caballero, D. & Bieniasz, P. D. Context-dependent effects of L domains and ubiquitination on viral budding. *J Virol* 78, 5554-5563(2004).

Martins, A. N. et al. Elucidation of the Molecular Mechanism Driving Duplication of the HIV-1 PTAP Late Domain. *J Virol* 90, 768-779 (2016).

Medina et al., TSG101 can replace Nedd4 function in ASV Gag release but not membrane targeting. *Virol.* 377, 30-8 (2008).

Patnaik, A., Chau, V. & Wills, J. W. Ubiquitin is part of the retrovirus budding machinery. *Proc Natl Acad Sci USA* 97, 13069-13074 (2000).

Ponting, C. P., Cai, Y. D. & Bork, P. The breast cancer gene product TSG101: a regulator of ubiquitination? *J Mol Med (Berl)* 75, 467-469 (1997).

Pornillos, O. et al. Structure and functional interactions of the Tsg101 UEV domain. *EMBO J* 21, 2397-2406 (2002).

Pornillos, O., Alam, S. L., Davis, D. R. & Sundquist, W. I. Structure of the Tsg101 UEV domain in complex with the PTAP motif of the HIV-1 p6 protein. *Nat Struct Biol* 9 (2002).

Primi, M. P., Bueno, L., Baumer, P., Berard, H., Lecomte, J. M. Racecadotril demonstrates intestinal antisecretory activity in vivo. *Alimentary Pharmacology and Therapeutics.* 13 (Suppl 6), 3-7. PMID 10646045. doi:10.1046/j.1365-2036.13.s6.3.x (1999).

Raiborg, C. & Stenmark, H. The ESCRT machinery in endosomal sorting of ubiquitylated membrane proteins. *Nature* 458, 445-452 (2009).

Ruland, J. et al. p53 accumulation, defective cell proliferation, and early embryonic lethality in mice lacking tsg101. *Proc Natl Acad Sci USA* 98, 1859-1864 (2001).

Schonbuhler, B. et al. BAG2 Interferes with CHIP-Mediated Ubiquitination of HSP72. *Int J Mol Sci* 18(2016).

Schubert, U. et al. Proteasome inhibition interferes with gag polyprotein processing, release, and maturation of HIV-1 and HIV-2. *Proc Natl Acad Sci US A* 97, 13057-13062 (2000).

Schwartz, O., Marechal, V., Friguet, B., Arenzana-Seisdedos, F. & Heard, J. M. Antiviral activity of the proteasome on incoming human immunodeficiency virus type 1. *J Virol* 72 (1998).

Schwieters, C. D., Kuszewski, J. J., Tjandra, N. & Clore, G. M. The Xplor-NIH NMR molecular structure determination package. *J Magn Reson* 160, 65-73 (2003).

Schwieters, C. D., Kuszewski, J. J. & Clore, G. M. Using Xplor-NIH for NMR molecular structure determination. *Prog Nucl Mag Res Sp* 48, 47-62 (2006).

Sette, P., Nagashima, K., Piper, R. C. & Bouamr, F. Ubiquitin conjugation to Gag is essential for ESCRT-mediated HIV-1 budding. *Retrovirology* 10, 79(2013).

Shen, Y. & Bax, A. Identification of helix capping and b-turn motifs from NMR chemical shifts. *J Biomol NMR* 52, 211-232 (2012).

Shen, Y. & Bax, A. Protein backbone and sidechain orsion angles predicted from NMR chemical shifts using artificial neural networks. *J Biomol NMR* 56, 227-241(2013).

Shin, J. M. & Kim, N. Pharmacokinctics and pharmacodynamics of the proton pump inhibitors. *J Neurogastroenterol Motil* 19 (2013).

Srinivasan, S., Meyer, R. D., Lugo, R. & Rahimi, N. Identification of PDCL3 as a novel chaperone protein involved in the generation of functional VEGF receptor 2. *J Biol Chem* 288, 23171-23181 (2013).

Strack, B., Calistri, A., Accola, M. A., Palu, G. & Gottlinger, H. G. A role for ubiquitin ligase recruitment in retrovirus release. *Proc Natl Acad Sci USA* 97, 13063-13068(2000).

Sundquist, W. I. et al. Ubiquitin recognition by the human TSG101 protein. *Mol Cell* 13, 783-789 (2004).

Tavassoli, A. et al. Inhibition of HIV budding by a genetically selected cyclic peptide targeting the Gag-TSG101 interaction. *ACS Chem Biol* 3, 757-764 (2008).

Teo, H., Veprintsev, D. B. & Williams, R. L. Structural insights into endosomal sorting complex required for transport (ESCRT-I) recognition of ubiquitinated proteins. *J Biol Chem* 279, 28689-28696 (2004).

Tomas, A., Futter, C. E. & Eden, E. R. EGF receptor trafficking: consequences for signaling and cancer. *Trends Cell Biol* 24, 26-34 (2014).

Townsley, F. M., Aristarkhov, A., Beck, S., Hershko, A. & Ruderman, J. V. Dominant-negative cyclin-selective ubiquitin carrier protein E2-C/UbcH10 blocks cells in metaphase. *Proc Natl Acad Sci USA* 94, 2362-2367 (1997).

VerPlank, L. et al. Tsg101, a homologue of ubiquitin-conjugating (E2) enzymes, binds the L domain in HIV type 1 Pr55(Gag). *Proc Natl Acad Sci USA* 98, 7724-7729, (2001).

Votteler, J. & Sundquist, W. 1. Virus budding and the ESCRT pathway. *Cell Host Microbe* 14, 232-241 (2013).

Vranken, W. F. et al. The CCPN data model for NMR spectroscopy: development of a software pipeline. *Proteins* 59, 687-696 (2005).

Watanabe, S. M. et al. The S40 residue in HIV-1 Gag p6 impacts local and distal budding determinants, revealing additional late domain activities. *Retrovirology* 10, 143 (2013).

Welsch, S. et al. Ultrastructural analysis of ESCRT proteins suggests a role for endosome-associated tubular-vesicular membranes in ESCRT function. *Traffic* 7, 1551-1566 (2006).

Williamson, M. P. Using chemical shift perturbation to characterise ligand binding. *Prog Nucl Magn Reson Spectrosc* 73, 1-16 (2013).

Zhadina, M. & Bieniasz, P. D. Functional interchangeability of late domains, late domain cofactors and ubiquitin in viral budding. *PLoS Pathog* 6, e1001153 (2010).

Zwahlen, C. et al. Methods for measurement of intermolecular NOEs by multinuclear NMR spectroscopy: Application to a bacteriophage lambda N-peptide/boxB RNA complex. *Journal of the American Chemical Society* 119, 6711-6721 (1997).

What is claimed is:

1. A method of inhibiting release of a virus from a cell, comprising contacting the cell with a compound that binds an ubiquitin E2 variant (UEV) domain of Tsg 101 protein, or fragment thereof, with an affinity sufficient to inhibit or disrupt the binding of the Tsg 101 protein, or fragment thereof, to ubiquitin, wherein the compound disrupts at least 50% of the binding of the UEV domain of the cellular polypeptide, or fragment thereof, to ubiquitin, wherein the virus is at least one of Human Immunodeficiency virus type 1 (HIV-1), Hepatitis C virus, Human Papillomavirus, Herpes Simplex virus type 1, Dengue virus, Japanese Encephalitis virus, Human Parainfluenzavirus Type 1, Epstein Barr Virus, Mopeia virus, Tacaribe virus, Human Cytomegalovirus, Measles virus or Influenza virus;

wherein the compound is:

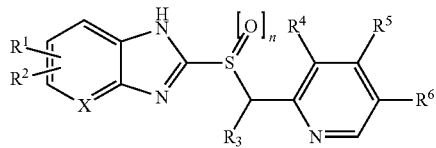

wherein:
- $R^1$ is H, halogen, $C_{1-6}$ alkyl unsubstituted or substituted with halogen, $C_{1-8}$ alkoxy unsubstituted or substituted with fluorine or a cycloalkyl group of 3-6 carbon atoms, chlorodifluoromethoxy, fluoroalkyloxy, $C_{1-6}$ alkoxycarbonyl or carboxyl group, or alkanoyl;
- $R^2$ is H, halogen, $C_{1-6}$ alkyl unsubstituted or substituted with halogen, $C_{1-6}$ alkoxy unsubstituted or substituted with fluorine, $C_{1-6}$ alkoxycarbonyl or carboxyl group, or alkanoyl;
- $R^3$ is H, methyl or ethyl;
- $R^4$ is H, $C_{1-6}$ alkyl, $C_{1-3}$ alkoxy, methoxyethoxy, or ethoxyethoxy;
- $R^5$ is H, methyl, $C_{1-5}$ alkoxy unsubstituted or substituted with fluorine, methoxyethoxy, ethoxyethoxy, or $-OC_{2-10}$ alkyl-$OC_{0-6}$ alkyl;
- $R^6$ is H, $C_{1-3}$ alkyl, $C_{1-3}$ alkoxy, methoxyethoxy, or ethoxyethoxy;
- n is 0-2; and
- X is C, C—$R^1$ or —$R^2$, or N.

2. The method of claim 1, wherein the compound binds the UEV domain of the cellular polypeptide, or fragment thereof, with an affinity sufficient to inhibit or disrupt formation of an associative complex comprising the cellular polypeptide, or fragment thereof, that includes the UEV domain Ub-binding pocket, and:
   a) an ubiquitin-modified polypeptide of the virus, or fragment thereof, that is capable of binding said UEV domain Ub-binding pocket; or
   b) an ubiquitin-modified cellular polypeptide for the virus' production other than the cellular polypeptide that includes the UEV domain Ub-binding pocket, or fragment thereof, that is capable of binding said UEV domain Ub-binding pocket.

3. The method of claim 2, wherein the associative complex comprises a) the cellular polypeptide, or fragment thereof, that includes the UEV domain Ub-binding pocket and b) an ubiquitin-modified cellular polypeptide for the virus' production other than the cellular polypeptide that includes the UEV domain Ub-binding pocket, or fragment thereof, that is capable of binding said UEV domain Ub-binding pocket, wherein the associative complex optionally further comprises a) an ubiquitin-modified polypeptide of the virus, or fragment thereof, that is capable of binding said UEV domain Ub-binding pocket.

4. A method of treating a patient infected with a virus, comprising administering to the patient a compound which binds to the UEV domain Ub-binding pocket of Tsg 101 protein in an amount effective to inhibit the binding of the Tsg 101 protein to ubiquitin, so as to thereby treat the patient, wherein the compound disrupts at least 50% of the binding of the UEV domain of the cellular polypeptide, or fragment thereof, to ubiquitin, wherein the virus is at least one of Human Immunodeficiency virus type 1 (HIV-1), Hepatitis C virus, Human Papillomavirus, Herpes Simplex virus type 1, Dengue virus, Japanese Encephalitis virus, Human Parainfluenzavirus Type 1, Epstein Barr Virus, Mopeia virus, Tacaribe virus, Human Cytomegalovirus, Measles virus or Influenza virus; wherein the compound is:

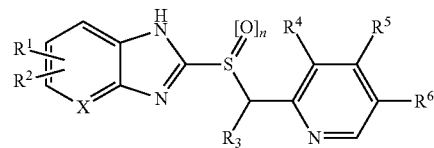

wherein:
- $R^1$ is H, halogen, $C_{1-6}$ alkyl unsubstituted or substituted with halogen, $C_{1-8}$ alkoxy unsubstituted or substituted with fluorine or a cycloalkyl group of 3-6 carbon atoms, chlorodifluoromethoxy, fluoroalkyloxy, $C_{1-6}$ alkoxycarbonyl or carboxyl group, or alkanoyl;
- $R^2$ is H, halogen, $C_{1-6}$ alkyl unsubstituted or substituted with halogen, $C_{1-6}$ alkoxy unsubstituted or substituted with fluorine, $C_{1-6}$ alkoxycarbonyl or carboxyl group, or alkanoyl;
- $R^3$ is H, methyl or ethyl;

R$^4$ is H, C$_{1-6}$ alkyl, C$_{1-3}$ alkoxy, methoxyethoxy, or ethoxyethoxy;

R$^5$ is H, methyl, C$_{1-5}$ alkoxy unsubstituted or substituted with fluorine, methoxyethoxy, ethoxyethoxy, or —OC$_{2-10}$ alkyl-OC$_{0-6}$ alkyl;

R$^6$ is H, C$_{1-3}$ alkyl, C$_{1-3}$ alkoxy, methoxyethoxy, or ethoxyethoxy;

n is 0-2; and

X is C, C—R$^1$ or —R$^2$, or N.

5. The method of claim 4 wherein the virus is an enveloped virus.

6. The method of claim 4, wherein the virus is not known to have an L-domain motif, wherein the L-domain motif is any one of PPX$_n$Y, PTAP or LYPX$_n$L.

7. The method of claim 4, wherein the virus is known to have an L-domain motif, wherein the L-domain motif is any one of PPX$_n$Y, PTAP or LYPX$_n$L.

8. The method of claim 7, wherein the virus is at least one of Human Immunodeficiency virus type 1 (HIV-1), Influenza virus or Human cytomegalovirus.

9. The method of claim 4, wherein the virus is at least one of Dengue virus, Epstein Barr virus, Influenza virus, Measles virus, Human Immunodeficiency virus type 1 (HIV-1), Human Papillomavirus, or Herpes Simplex virus type 1.

10. The method of claim 4, wherein the virus is not an enveloped virus.

11. The method of claim 10, wherein the virus is Human Papilloma virus.

12. The method of claim 1, wherein R$^1$ is halogen, C$_{1-6}$ alkyl substituted with halogen, chlorodifluoromethoxy, or C$_{3-6}$ alkoxycarbonyl or carboxyl group;

R$^2$ is halogen, C$_{1-6}$ alkyl substituted with halogen, C$_{1-6}$ alkoxy unsubstituted or substituted with fluorine, or C$_{3-6}$ alkoxycarbonyl or carboxyl group;

R$^3$ is H;

R$^4$ is C$_{2-6}$ alkyl or C$_3$ alkoxy;

R$^5$ is C$_{3-5}$ alkoxy unsubstituted, C$_{2-5}$ alkoxy substituted with fluorine, or —OC$_{2-10}$ alkyl-OC$_{0-6}$ alkyl;

R$^6$ is C$_{2-3}$ alkyl or C$_3$ alkoxy;

n is 0-2; and

X is C, or C—R$^1$ or —R$^2$.

13. The method of claim 12, wherein:

R$^1$ is C$_{1-8}$ alkoxy unsubstituted or substituted with a cycloalkyl group of 3-6 carbon atoms or fluoroalkyloxy;

R$^2$ is H;

R$^3$ is H;

R$^4$ is H or methyl;

R$^5$ is H, methyl or methoxy;

R$^6$ is H or methyl;

n is 1; and

X is N; or

R$^1$ and R$^2$ are independently H, C$_{1-6}$ alkyl, halogen, methoxycarbonyl, ethoxycarbonyl, alkoxy, or alkanoyl;

R$^3$ is H, methyl, or ethyl;

R$^4$-R$^6$ are independently H, methyl, methoxy, ethoxy, methoxyethoxy, or ethoxyethoxy, wherein R$^4$-R$^6$ are not all hydrogen, and wherein if two of R$^4$-R$^6$ are hydrogen, then the remaining group is not methyl;

n is 1; and

X is C, or C—R$^1$ or —R$^2$; or

R$^1$ is C$_{1-3}$ alkoxy substituted with fluorine, or chlorodifluoromethoxy;

R$^2$ is H, halogen, trifluoromethyl, C$_{1-3}$ alkyl, or C$_{1-3}$ alkoxy unsubstituted or substituted with fluorine;

R$^3$ is H;

R$^4$ and R$^6$ are independently H, C$_{1-3}$ alkyl, or C$_{1-3}$ alkoxy, wherein R$^4$ and R$^6$ are not the same and wherein one of R$^4$ and R$^6$ is C$_{1-3}$ alkoxy;

R$^5$ is C$_{1-3}$ alkoxy;

n is 0 or 1; and

X is C, or C—R$^1$ or —R$^2$; or

R$^1$ is H, methoxy, or trifluoromethyl;

R$^2$ is H;

R$^3$ is H;

R$^4$ and R$^6$ are independently H or methyl;

R$^5$ is C$_{2-5}$ alkoxy substituted with fluorine;

n is 0 or 1; and

X is C, or C—R$^1$ or —R$^2$; or

R$^1$ and R$^2$ are independently H, halogen, C$_{1-6}$ alkyl unsubstituted or substituted with halogen, C$_{1-6}$ alkoxy, or C$_{1-6}$ alkoxycarbonyl or carboxyl group;

R$^3$ is H;

R$^4$ is C$_{1-6}$ alkyl;

R$^5$ is —OC$_{2-10}$ alkyl-OC$_{0-6}$ alkyl;

R$^6$ is H;

n is 0-2; and

X is C, or C—R$^1$ or —R$^2$.

14. The method of claim 4, wherein the compound has the structure:

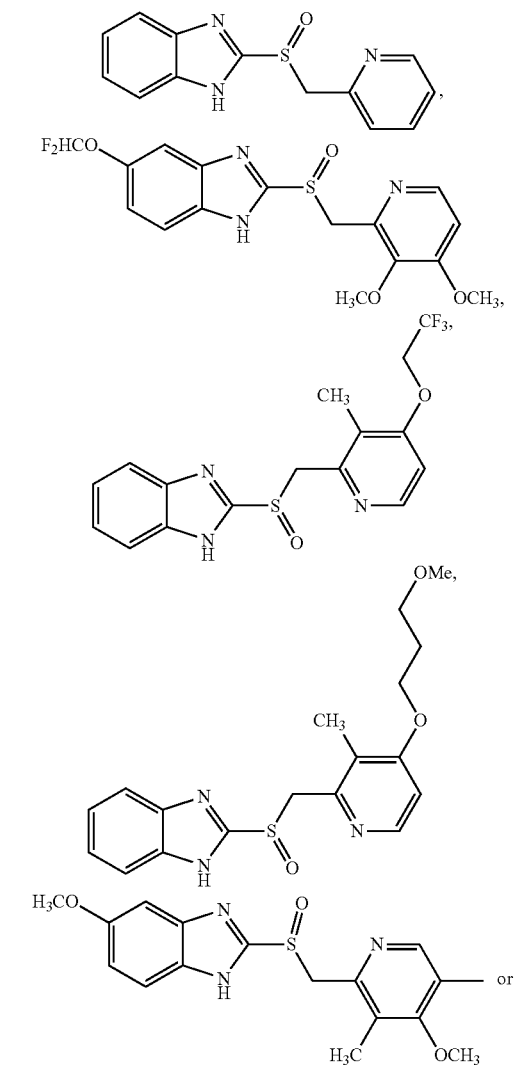

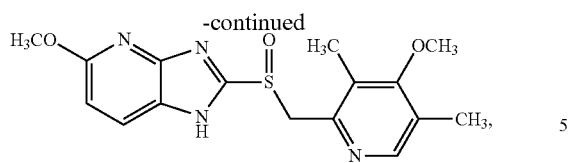

or a pharmaceutically acceptable salt thereof.

15. The method of claim 1, wherein the cell is a human cell or a plant cell.

16. The method of claim 15, wherein the virus in the plant cell is at least one of Tomato Bushy Stunt virus or Brome mosaic virus.

17. The method of claim 1, wherein the virus is at least one of Dengue virus, Epstein Barr virus, Influenza virus, Measles virus, Human Immunodeficiency virus type 1 (HIV-1).

18. The method of claim 1, wherein the virus is Human Immunodeficiency virus type 1 (HIV-1).

19. The method of claim 4, wherein the virus is Human Immunodeficiency virus type 1 (HIV-1).

20. The method of claim 1, wherein the compound is present at a concentration of 1-200 μm.

* * * * *